United States Patent
Applebaum

(10) Patent No.: US 10,335,372 B2
(45) Date of Patent: *Jul. 2, 2019

(54) COMPOSITIONS WITH MODIFIED NUCLEASES TARGETED TO VIRAL NUCLEIC ACIDS AND METHODS OF USE FOR PREVENTION AND TREATMENT OF VIRAL DISEASES

(71) Applicant: Avirid, Inc., Gainesville, FL (US)

(72) Inventor: Jacob G. Applebaum, Gainesville, FL (US)

(73) Assignee: Jacob G. Appelbaum, Gainesville, FL (US)

( * ) Notice: Subject to any disclaimer, the term of this patent is extended or adjusted under 35 U.S.C. 154(b) by 47 days.

This patent is subject to a terminal disclaimer.

(21) Appl. No.: 15/455,574

(22) Filed: Mar. 10, 2017

(65) Prior Publication Data
US 2017/0209376 A1    Jul. 27, 2017

Related U.S. Application Data

(63) Continuation of application No. 11/578,716, filed as application No. PCT/US2005/012532 on Apr. 14, 2005, now Pat. No. 9,592,277.

(60) Provisional application No. 60/561,934, filed on Apr. 14, 2004.

(51) Int. Cl.
*A61K 38/46* (2006.01)
*A61K 9/16* (2006.01)

(52) U.S. Cl.
CPC .......... *A61K 9/1676* (2013.01); *A61K 9/1641* (2013.01); *A61K 9/1652* (2013.01); *A61K 9/1658* (2013.01); *A61K 38/465* (2013.01); *C12Y 301/21001* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 5,115,096 A | 5/1992 | Shoyab et al. | |
| 5,484,589 A | 1/1996 | Salganik | |
| 5,690,942 A | 11/1997 | Hjorth | |

(Continued)

FOREIGN PATENT DOCUMENTS

| | | |
|---|---|---|
| JP | H08-502162 | 3/1996 |
| WO | 9010015 | 9/1990 |

(Continued)

OTHER PUBLICATIONS

Jackson et al., "A designed peptide ligase for total synthesis of ribonuclease A with unnatural catalytic residues", Science, vol. 266, pp. 243-247, 1994.

(Continued)

*Primary Examiner* — Richard C Ekstrom
(74) *Attorney, Agent, or Firm* — Peter J. Mikesell; Schmeiser, Olsen & Watts, LLP

(57) ABSTRACT

Antiviral compositions comprising a modified nuclease, or a plurality of such modified nucleases having at least one non-natural amino acid residue substituted for a naturally occurring amino acid in a parent nuclease are provided, as are methods of use and kits providing unit dosages of such compositions.

17 Claims, 3 Drawing Sheets
Specification includes a Sequence Listing.

(56) References Cited

U.S. PATENT DOCUMENTS

| | | |
|---|---|---|
| 5,698,515 A | 12/1997 | Plate et al. |
| 5,739,512 A | 4/1998 | Tognazzini |
| 5,792,640 A | 8/1998 | Chandrasegaran |
| 5,989,886 A | 11/1999 | Boeke et al. |
| 5,997,861 A | 12/1999 | Virtanen et al. |
| 6,017,537 A | 1/2000 | Alexander et al. |
| 6,280,991 B1 | 8/2001 | Raines |
| 6,312,956 B1 | 11/2001 | Lane |
| 6,342,244 B1 | 1/2002 | Zalipsky |
| 9,592,277 B2 * | 3/2017 | Appelbaum ......... A61K 38/465 |
| 2001/0021763 A1 | 9/2001 | Harris |
| 2001/0041360 A1 | 11/2001 | Lazarus et al. |
| 2001/0053521 A1 | 12/2001 | Kreimer et al. |
| 2002/0127198 A1 | 9/2002 | Rothbard et al. |
| 2002/0127695 A1 | 9/2002 | Davis et al. |
| 2002/0146788 A1 | 10/2002 | Franklin |
| 2002/0173025 A1 | 11/2002 | Lazarus et al. |
| 2002/0187198 A1 | 12/2002 | Lee |
| 2003/0044796 A1 | 3/2003 | Neri et al. |
| 2003/0059789 A1 | 3/2003 | Efimov et al. |
| 2003/0083256 A1 | 5/2003 | Rothbard et al. |
| 2003/0087808 A1 | 5/2003 | Soltero et al. |
| 2003/0096400 A1 | 5/2003 | Kinstler |
| 2003/0171267 A1 | 9/2003 | Rosen et al. |
| 2004/0147027 A1 | 7/2004 | Troy et al. |
| 2014/0017241 A1 | 1/2014 | Strong et al. |

FOREIGN PATENT DOCUMENTS

| | | |
|---|---|---|
| WO | 9324660 | 12/1993 |
| WO | 9500170 | 1/1995 |
| WO | 9747751 | 12/1997 |
| WO | 02094250 | 11/2002 |
| WO | 03038104 | 5/2003 |
| WO | 04024919 | 3/2004 |

OTHER PUBLICATIONS

Guo et al., "Protein tolerance to random amino acid change", Proceedings of the National Academy of Sciences USA, vol. 101, No. 25, pp. 9205-9210, 2004.

James et al., "Kinetic characterization of ribonuclease S mutants containing photoisomerizable phenylazophenylalanine residues", Protein Engineering, vol. 14, No. 12, pp. 983-991, 2001.

Melekhovets et al., "Fusion with an RNA binding domain to confer target RNA specificity to an RNase: design and engineering of Tat-RNase H that specifically recognizes and cleaves HIV-1 RNA in vitro," Nucleic Acids Research (1996) 24(10):1908-1912.

European Supplemental Search Report for Application No. 05780021.1, dated Sep. 26, 2012. (3 pages).

Hendrickson et al., Incorporation of nonnatural amino acids into proteins. Ann Rev Biochem. Mar. 26, 2004:73; 147-76.

Weston et al., X-ray structure of the 1-39 DNase I-d(GGTATACC)2 complex at 2.3 A resolution. J Mal Biol. May 20, 1992:226;1237-56.

Australian Office Action for Application No. 2011200602 dated Apr. 3, 2012. (2 pages).

Beintema et al., The amino acid sequence of human pancreatic ribonuclease; Analytical Biochem., vol. 135, pp. 48-64 (1984) Appendix A.

Leland et al., Endowing human pancreatic ribonuclease with toxicity for cancer cells; J Biol Chem., vol. 276, pp. 43095-43102 (2001) Appendix B.

Australian Office Action AU Appl. No. 2005247298 dated Mar. 5, 2010.

Australian Office Action for AU Appl. No. 2011200602 dated Sep. 5, 2011.

Noren et al.; A general Method for site-specific incorporation of unnatural amino acids into proteins, Science, vol. 244, pp. 182-188 (1989).

Oh et al.; Synthesis of Novel Unnatural Amino Acid as a Building Block and its Incorporation into an Antimicrobial Peptide, Bioorg Med Chem, vol. 7, pp. 2985-2990 (1999).

White, et al.; Sequential site-directed mutagenesis and chemical modification to convert the active site arginine 292 of aspartate aminotransferase to homoarginine, J Am Chem Soc, vol. 114, pp. 3567-3568 (1992).

Wang, et al.; Addition of the keto functional group to the genetic code of *Escherichia coli*; PNAS, vol. 100, pp. 56-61 Jan. 7, 2003.

Trukhackev et al; The effect of deoxyribonuclease on the synthesis of DNA of vaccinia virus ;Virology, vol. 33, pp. 552-555 (Nov. 1967).

Datta, D. et al.; A Designed Phenylalanyl-tRNA Synthetase Variant Allows Efficient in Vivo Incorporation of Aryl Ketone Functionality into Proteins; J Am Chem Soc, vol. 124, pp. 5652-5653; May 1, 2002.

Welch, J. et al.; De novo nucleases based on HTH and EF-hand chimeras, Inorg Chem, 2001; vol. 40, pp. 1982-1984.

Fitzsimons, M. et al.; Design of a Synthetic Nuclease: DNA Hydrolysis by a Zinc-Binding Peptide tethered to a Rhodium Intercalator; J Am Chem Soc, vol. 119, pp. 3379-3380 (1997).

Beerens, A. et al.; Protein Transduction Domains and their Utility in Gene Therapy, Curr Gene Ther, vol. 3, pp. 18-34 (2003).

Futaki, S. et al.; Arginine-rich Peptides, J Biol Chem, vol. 276, pp. 5836-5840 (2001).

Esfand, R. et al.; Poly(amidoamine) (PAMAM) dendrimers: from biomimicry to drug delivery and biomedical applications, Drug Disc Today, vol. 6, pp. 427-436 (Apr. 8, 2001).

Sandor, Z. et al.; Repair of triple helix directed psoralen adducts in human cells, Nucleic Acids Res, vol. 22, No. 11 pp. 2051-2056 (1994).

Lee, Y. et al.; Glycobiology in Medicine; J Biomed Sci, vol. 3, pp. 221-237 (1996).

International Search Report for PCT Application PCT/US05/012532 dated Sep. 18, 2006.

Knight, D.A. et al.; Artificial Nucleases as Antiviral, Antibacterial Agents, Storming Media Pentagon Reports, Report No. A860354, Nov. 19, 2003, Abstract.

Judice et al.; "Probing the Mechaism of Staphylococcal Nuclease with Unnatural Amino Acids: Kinetic and Structural Studies" Science Sep. 17, 1993; 261, 5128, p. 1578-1581.

UniProtKB/Swiss-Prot P07998 (RNAS1_HUMAN), 11 pages, accessed Aug. 3, 2010 http://www.uniprot.org/uniproUP07998.html.

Barnard, D. L. et al., "Potent Inhibition of Respiratory Syncytial Virus by Polyoxometalates of Several Structural Classes", Antiviral Research, vol. 34, pp. 27-37, 1997.

Bourne, N. et al., "Dendrimers, A New Class of Candidate Topical Microbicides With Activity Against Herpes Simplex Virus Infection", Antimicrobial Agents and Chemotherapy, vol. 44, pp. 2471-2474, 2000.

Bousarghin, L. et al., "Positively Charged Sequences of Human Papillomavirus Type 16 Capsid Proteins Are Sufficient to Mediate Gene Transfer Into Target Cells via the Heparan Sulfate Receptor", Journal of General Virology, vol. 84, pp. 157-164, 2003.

Brunetti, C. R. et al., "Role of Mannose-6-Phosphate Receptors in Herpes Simplex Virus Entry Into Cells and Cell-To-Cell Transmission", Journal of Virology, vol. 69, pp. 3517-3528, 1995

Diebold, S. S. et al., "Mannose Polyethylenimine Conjugates for Targeted DNA Delivery Into Dendritic Cells", The Journal of Biological Chemistry, vol. 274, pp. 19087-19094, 1999.

Dingwall, C. et al., "Nuclear Targeting Sequences—A Consensus?", Trends Biochem. Sci., vol. 16, pp. 478-481, 1991.

Egholm, M. et al., "Efficient ph-Independent Sequence-Specific DNA Binding by Pseudoisocytosine-Containing Bis-PNA", Nucleic Acids Research, vol. 23, pp. 217-222, 1995.

Gong, Y. et al., "Evidence of Dual Sites of Action of Dendrimers: SPL-2999 Inhibits Both Virus Entry and Late Stages of Herpes Simplex Virus Replication", Antiviral Research, vol. 55, pp. 319-329, 2002.

Hruby, D.E. et al., "Fine Structure Analysis and Nucleotide Sequence of the Vaccinia Virus Thymidine Kinase Gene", Proc. Natl. Acad. Sci USA, vol. 80, pp. 3411-3415, 1983.

Kuwasaki, T. et al., "Inhibition of Human Immunodeficiency Virus 1 Replication In Vitro by a Self-Stabilized Oligonucleotide With 2'-0-Methyl-Guanosine-Uridine Quadruplex Motifs", Journal of Antimicrobial Chemotherapy, vol. 51, pp. 813-819, 2003.

(56) References Cited

OTHER PUBLICATIONS

Pan, C. Q. et al., "Improved Potency of Hyperactive and Actin-Resistant Human Dnase I Variants for Treatment of Cystic Fibrosis and Systemic Lupus Erythematosus", The Journal of Biological Chemistry, vol. 273, pp. 18374-18381, 1998.

Takenawa, T. et al., "Cyanocysteine-Mediated Molecular Dissection of Dihydrofolate Reductase: Occurrence of Intra- and Inter-Molecular Reactions Forming a Peptide Bond", J. Biochem., vol. 123, pp. 1137-1144, 1998.

Trollsas, M. et al., "Dendrimer-Like Star Polymers: Amplification of Dendrimer Properties, Structural Conformation and Hydrodynamic Volume", Polymer Preprints, vol. 41, pp. 258-259, 2000.

Lanford, R. E. et al., "Construction and Characterization of an SV40 Mutant Defective in Nuclear Transport of T Antigen", Cell, vol. 37, pp. 801-813, 1984.

Monsigny, M. et al., "Colormetric Determination of Neutral Sugars by a Resorcinol Sulfuric Acid Micromethod", Analytical Biochemistry, vol. 175, pp. 525-530, 1988.

Tkachenko, A. G. et al., "Multifunctional Gold Nanoparticle—Peptide Complexes for Nuclear Targeting", J. Am. Chem. Soc., vol. 125, pp. 4700-4701, 2003.

Japanese Office Action for JP Appl. No. 2007-508498 dated Feb. 7, 2011.

\* cited by examiner

SEQUENCE LISTING

```
<160> NUMBER OF SEQ ID NOS: 60

<210> SEQ ID NO 1
<211> LENGTH: 7
<212> TYPE: PRT
<213> ORGANISM: Artificial
<220> FEATURE:
<223> OTHER INFORMATION: Synethetic Construct

<400> SEQUENCE: 1

Ala Ser Thr Thr Asn Tyr Thr
1               5

<210> SEQ ID NO 2
<211> LENGTH: 11
<212> TYPE: PRT
<213> ORGANISM: Artificial
<220> FEATURE:
```

<223> OTHER INFORMATION: Synthetic Construct

<400> SEQUENCE: 2

His Asn Glu Arg Leu Glu Phe Leu Gly Asp Ser
1               5                   10

<210> SEQ ID NO 3
<211> LENGTH: 15
<212> TYPE: PRT
<213> ORGANISM: Artificial
<220> FEATURE:
<223> OTHER INFORMATION: Synthetic Construct

<400> SEQUENCE: 3

Lys Glu Thr Ala Ala Ala Lys Phe Glu Arg Gln His Met Asp Ser
1               5                   10                  15

<210> SEQ ID NO 4
<211> LENGTH: 33
<212> TYPE: PRT
<213> ORGANISM: Artificial
<220> FEATURE:
<223> OTHER INFORMATION: Synthetic Construct

<400> SEQUENCE: 4

Thr Glu Arg Arg Arg Gln Gln Leu Asp Lys Asp Gly Asp Gly Thr Ile
1               5                   10                  15

Asp Glu Arg Glu Ile Lys Ile His Phe Gln Asn Lys Arg Ala Lys Ile
                20                  25                  30

Lys

<210> SEQ ID NO 5
<211> LENGTH: 34
<212> TYPE: PRT
<213> ORGANISM: Artificial
<220> FEATURE:
<223> OTHER INFORMATION: Synthetic Construct

<400> SEQUENCE: 5

Thr Glu Arg Arg Arg Phe Asp Lys Asp Gln Asn Gly Tyr Ile Gly Ala
1               5                   10                  15

Ala Asp Leu Arg His Val Lys Ile Trp Phe Gln Asn Lys Arg Ala Lys
                20                  25                  30

Ile Lys

<210> SEQ ID NO 6
<211> LENGTH: 33
<212> TYPE: PRT
<213> ORGANISM: Artificial
<220> FEATURE:
<223> OTHER INFORMATION: Synthetic Construct

<400> SEQUENCE: 6

Thr Glu Arg Arg Arg Phe Arg Val Phe Asp Lys Asp Gly Asn Gly Tyr
1               5                   10                  15

Ile Ser Ala Ala Glu Lys Ile Trp Phe Gln Asn Lys Glu Ala Lys Ile
                20                  25                  30

Lys

<210> SEQ ID NO 7
<211> LENGTH: 33
<212> TYPE: PRT
<213> ORGANISM: Artificial

<220> FEATURE:
<223> OTHER INFORMATION: Synthetic Construct

<400> SEQUENCE: 7

Thr Arg Arg Arg Arg Phe Ser Leu Phe Asp Lys Asp Gly Asp Gly Thr
1               5                   10                  15

Ile Thr Thr Lys Glu Glu Val Trp Phe Gln Asn Arg Arg Met Lys Trp
                20                  25                  30

Lys

<210> SEQ ID NO 8
<211> LENGTH: 63
<212> TYPE: PRT
<213> ORGANISM: Artificial
<220> FEATURE:
<223> OTHER INFORMATION: Synthetic Construct

<400> SEQUENCE: 8

Asp Glu Lys Arg Pro Arg Thr Ala Phe Ser Gly Glu Gln Leu Ala Arg
1               5                   10                  15

Leu Lys Arg Glu Phe Asn Glu Asn Arg Tyr Leu Thr Glu Arg Arg Arg
                20                  25                  30

Leu Arg Val Phe Asp Lys Asp Gly Asn Gly Phe Ile Ser Ala Ala Glu
            35                  40                  45

Lys Ile Trp Phe Gln Asn Lys Arg Ala Lys Ile Lys Lys Ser Thr
        50                  55                  60

<210> SEQ ID NO 9
<211> LENGTH: 16
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (16)..(16)
<223> OTHER INFORMATION: AMIDATION

<400> SEQUENCE: 9

Asp Pro Asp Glu Leu Glu His Ala Ala Lys His Glu Ala Ala Ala Lys
1               5                   10                  15

<210> SEQ ID NO 10
<211> LENGTH: 6
<212> TYPE: PRT
<213> ORGANISM: Artificial
<220> FEATURE:
<223> OTHER INFORMATION: Synthetic Construct

<400> SEQUENCE: 10

Gly Phe Ser Leu His Ala
1               5

<210> SEQ ID NO 11
<211> LENGTH: 6
<212> TYPE: PRT
<213> ORGANISM: Artificial
<220> FEATURE:
<223> OTHER INFORMATION: Synthetic Construct

<400> SEQUENCE: 11

Phe Ser Phe Leu His Ala
1               5

```
<210> SEQ ID NO 12
<211> LENGTH: 6
<212> TYPE: PRT
<213> ORGANISM: Artificial
<220> FEATURE:
<223> OTHER INFORMATION: Synthetic Construct

<400> SEQUENCE: 12

Ser Ser Phe Leu His Ala
1               5

<210> SEQ ID NO 13
<211> LENGTH: 8
<212> TYPE: PRT
<213> ORGANISM: Artificial
<220> FEATURE:
<223> OTHER INFORMATION: Synthetic Construct

<400> SEQUENCE: 13

Arg Arg Trp His Arg Leu Lys Glu
1               5

<210> SEQ ID NO 14
<211> LENGTH: 11
<212> TYPE: PRT
<213> ORGANISM: Artificial
<220> FEATURE:
<223> OTHER INFORMATION: Synthetic Construct

<400> SEQUENCE: 14

Ser Gly Gly His Gly Gly Arg Gly Gly His Phe
1               5                   10

<210> SEQ ID NO 15
<211> LENGTH: 11
<212> TYPE: PRT
<213> ORGANISM: Artificial
<220> FEATURE:
<223> OTHER INFORMATION: Synthetic Construct

<400> SEQUENCE: 15

Ser Gly Gly Ser Gly Gly Ser Gly Gly His Phe
1               5                   10

<210> SEQ ID NO 16
<211> LENGTH: 11
<212> TYPE: PRT
<213> ORGANISM: Artificial
<220> FEATURE:
<223> OTHER INFORMATION: Synthetic Construct

<400> SEQUENCE: 16

Ser Gly Gly Arg Gly Gly His Gly Gly His Phe
1               5                   10

<210> SEQ ID NO 17
<211> LENGTH: 11
<212> TYPE: PRT
<213> ORGANISM: Artificial
<220> FEATURE:
<223> OTHER INFORMATION: Synthetic Construct

<400> SEQUENCE: 17

Tyr Gly Arg Lys Lys Arg Pro Gln Arg Arg Arg
1               5                   10

<210> SEQ ID NO 18
```

```
<211> LENGTH: 16
<212> TYPE: PRT
<213> ORGANISM: Artificial
<220> FEATURE:
<223> OTHER INFORMATION: Synthetic Construct

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 16
<212> TYPE: PRT
<213> ORGANISM: Artificial
<220> FEATURE:
<223> OTHER INFORMATION: Synthetic Construct

<400> SEQUENCE: 19

Arg Arg Trp Arg Arg Trp Trp Arg Arg Trp Trp Arg Arg Trp Arg Arg
1               5                   10                  15

<210> SEQ ID NO 20
<211> LENGTH: 20
<212> TYPE: PRT
<213> ORGANISM: Artificial
<220> FEATURE:
<223> OTHER INFORMATION: Synthetic Construct

<400> SEQUENCE: 20

Cys Trp Lys Lys Lys Lys Lys Lys Lys Lys Lys Lys Lys Lys Lys Lys
1               5                   10                  15

Lys Lys Lys Lys
            20

<210> SEQ ID NO 21
<211> LENGTH: 40
<212> TYPE: PRT
<213> ORGANISM: Artificial
<220> FEATURE:
<223> OTHER INFORMATION: Synthetic Construct

<400> SEQUENCE: 21

Lys Lys Lys Lys Lys Lys Lys Lys Lys Lys Lys Lys Lys Lys Lys Lys
1               5                   10                  15

Lys Lys Trp Cys Cys Trp Lys Lys Lys Lys Lys Lys Lys Lys
                20                  25                  30

Lys Lys Lys Lys Lys Lys Lys Lys
        35                  40

<210> SEQ ID NO 22
<211> LENGTH: 26
<212> TYPE: PRT
<213> ORGANISM: Artificial
<220> FEATURE:
<223> OTHER INFORMATION: Synthetic Construct

<400> SEQUENCE: 22

Trp Thr Leu Asn Ser Ala Gly Tyr Leu Leu Gly Lys Ile Asn Leu Lys
1               5                   10                  15

Ala Leu Ala Ala Leu Ala Lys Lys Ile Leu
            20                  25

<210> SEQ ID NO 23
<211> LENGTH: 13
<212> TYPE: PRT
```

```
<213> ORGANISM: Artificial
<220> FEATURE:
<223> OTHER INFORMATION: Synthetic Construct

<400> SEQUENCE: 23

Gly Leu Phe Glu Ala Leu Glu Glu Leu Trp Glu Ala Lys
1               5                   10

<210> SEQ ID NO 24
<211> LENGTH: 46
<212> TYPE: PRT
<213> ORGANISM: Artificial
<220> FEATURE:
<223> OTHER INFORMATION: Synthetic Construct

<400> SEQUENCE: 24

Lys Lys Lys Lys Lys Lys Lys Lys Lys Lys Lys Lys Lys Lys Lys Lys
1               5                   10                  15

Gly Gly Cys Arg Gly Asp Met Phe Gly Cys Ala Lys Lys Lys Lys
            20                  25                  30

Lys Lys Lys Lys Lys Lys Lys Lys Lys Lys Arg Gly Asp
        35                  40                  45

<210> SEQ ID NO 25
<211> LENGTH: 25
<212> TYPE: PRT
<213> ORGANISM: Artificial
<220> FEATURE:
<223> OTHER INFORMATION: Synthetic Construct

<400> SEQUENCE: 25

Lys Lys Lys Lys Lys Lys Lys Lys Lys Lys Lys Lys Lys Lys Lys Lys
1               5                   10                  15

Gly Gly Cys Met Phe Gly Cys Gly Gly
            20                  25

<210> SEQ ID NO 26
<211> LENGTH: 31
<212> TYPE: PRT
<213> ORGANISM: Artificial
<220> FEATURE:
<223> OTHER INFORMATION: Synthetic Construct

<400> SEQUENCE: 26

Lys Lys Lys Lys Lys Lys Lys Lys Lys Lys Lys Lys Lys Lys Lys Lys
1               5                   10                  15

Ile Cys Arg Arg Ala Arg Gly Asp Asn Pro Asp Asp Arg Cys Thr
            20                  25                  30

<210> SEQ ID NO 27
<211> LENGTH: 22
<212> TYPE: PRT
<213> ORGANISM: Artificial
<220> FEATURE:
<223> OTHER INFORMATION: Synthetic Construct

<400> SEQUENCE: 27

Lys Lys Trp Lys Met Arg Arg Asn Gln Phe Trp Val Lys Val Gln Arg
1               5                   10                  15

Asx Ala Lys Asx Asx Ala
            20

<210> SEQ ID NO 28
<211> LENGTH: 30
```

```
<212> TYPE: PRT
<213> ORGANISM: Artificial
<220> FEATURE:
<223> OTHER INFORMATION: Synthetic Construct

<400> SEQUENCE: 28

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 29
<211> LENGTH: 32
<212> TYPE: PRT
<213> ORGANISM: Artificial
<220> FEATURE:
<223> OTHER INFORMATION: Synthetic Construct

<400> SEQUENCE: 29

Ile Gly Arg Ile Asp Pro Ala Asn Gly Lys Thr Lys Tyr Ala Pro Lys
1               5                   10                  15

Phe Gln Asp Lys Ala Thr Arg Ser Asn Tyr Tyr Gly Asn Ser Pro Ser
            20                  25                  30

<210> SEQ ID NO 30
<211> LENGTH: 21
<212> TYPE: PRT
<213> ORGANISM: Artificial
<220> FEATURE:
<223> OTHER INFORMATION: Synthetic Construct

<400> SEQUENCE: 30

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 31
<211> LENGTH: 12
<212> TYPE: PRT
<213> ORGANISM: Artificial
<220> FEATURE:
<223> OTHER INFORMATION: Synthetic Construct

<400> SEQUENCE: 31

Pro Leu Ala Glu Ile Asp Gly Ile Glu Leu Thr Tyr
1               5                   10

<210> SEQ ID NO 32
<211> LENGTH: 30
<212> TYPE: PRT
<213> ORGANISM: Artificial
<220> FEATURE:
<223> OTHER INFORMATION: Synthetic Construct

<400> SEQUENCE: 32

Lys Lys Lys Lys Lys Lys Lys Lys Lys Lys Lys Lys Lys Lys Lys Lys
1               5                   10                  15

Gly Gly Pro Leu Ala Glu Ile Asp Gly Ile Glu Leu Gly Ala
            20                  25                  30

<210> SEQ ID NO 33
<211> LENGTH: 30
<212> TYPE: PRT
<213> ORGANISM: Artificial
```

<220> FEATURE:
<223> OTHER INFORMATION: Synthetic Construct

<400> SEQUENCE: 33

```
Lys Lys Lys Lys Lys Lys Lys Lys Lys Lys Lys Lys Lys Lys Lys
1               5                   10                  15

Gly Gly Pro Leu Ala Glu Ile Asp Gly Ile Glu Leu Cys Ala
            20                  25                  30
```

<210> SEQ ID NO 34
<211> LENGTH: 28
<212> TYPE: PRT
<213> ORGANISM: Artificial
<220> FEATURE:
<223> OTHER INFORMATION: Synthetic Construct

<400> SEQUENCE: 34

```
Gly Ala Leu Phe Leu Gly Phe Leu Gly Gly Ala Ala Gly Ser Thr Met
1               5                   10                  15

Gly Ala Trp Ser Gln Pro Lys Ser Lys Arg Lys Val
            20                  25
```

<210> SEQ ID NO 35
<211> LENGTH: 28
<212> TYPE: PRT
<213> ORGANISM: Artificial
<220> FEATURE:
<223> OTHER INFORMATION: Synthetic Construct

<400> SEQUENCE: 35

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys
            20                  25
```

<210> SEQ ID NO 36
<211> LENGTH: 30
<212> TYPE: PRT
<213> ORGANISM: Artificial
<220> FEATURE:
<223> OTHER INFORMATION: Synthetic Construct

<400> SEQUENCE: 36

```
Leu Ala Arg Leu Leu Ala Arg Leu Leu Ala Arg Leu Leu Ala Arg Leu
1               5                   10                  15

Leu Ala Arg Leu Leu Ala Arg Leu Asn His Cys His His His
            20                  25                  30
```

<210> SEQ ID NO 37
<211> LENGTH: 16
<212> TYPE: PRT
<213> ORGANISM: Artificial
<220> FEATURE:
<223> OTHER INFORMATION: Synthetic Construct

<400> SEQUENCE: 37

```
Lys Leu Leu Lys Leu Leu Leu Lys Leu Trp Leu Leu Lys Leu Leu Leu
1               5                   10                  15
```

<210> SEQ ID NO 38
<211> LENGTH: 11
<212> TYPE: PRT
<213> ORGANISM: Artificial
<220> FEATURE:
<223> OTHER INFORMATION: Synthetic Construct

```
<400> SEQUENCE: 38

Lys Lys Lys Lys Lys Lys Lys Gly Gly Cys
1               5                   10

<210> SEQ ID NO 39
<211> LENGTH: 11
<212> TYPE: PRT
<213> ORGANISM: Artificial
<220> FEATURE:
<223> OTHER INFORMATION: Synthetic Construct

<400> SEQUENCE: 39

Lys Trp Lys Lys Lys Trp Lys Lys Gly Cys Cys
1               5                   10

<210> SEQ ID NO 40
<211> LENGTH: 11
<212> TYPE: PRT
<213> ORGANISM: Artificial
<220> FEATURE:
<223> OTHER INFORMATION: Synthetic Construct

<400> SEQUENCE: 40

Arg Trp Arg Arg Arg Trp Arg Arg Gly Gly Cys
1               5                   10

<210> SEQ ID NO 41
<211> LENGTH: 7
<212> TYPE: PRT
<213> ORGANISM: Artificial
<220> FEATURE:
<223> OTHER INFORMATION: Synthetic Construct

<400> SEQUENCE: 41

Pro Lys Lys Lys Arg Lys Val
1               5

<210> SEQ ID NO 42
<211> LENGTH: 12
<212> TYPE: PRT
<213> ORGANISM: Artificial
<220> FEATURE:
<223> OTHER INFORMATION: Synthetic Construct

<400> SEQUENCE: 42

Pro Glu Val Lys Lys Lys Arg Lys Pro Glu Tyr Pro
1               5                   10

<210> SEQ ID NO 43
<211> LENGTH: 12
<212> TYPE: PRT
<213> ORGANISM: Artificial
<220> FEATURE:
<223> OTHER INFORMATION: Synthetic Construct

<400> SEQUENCE: 43

Thr Pro Pro Lys Lys Lys Arg Lys Val Glu Asp Pro
1               5                   10

<210> SEQ ID NO 44
<211> LENGTH: 13
<212> TYPE: PRT
<213> ORGANISM: Artificial
<220> FEATURE:
<223> OTHER INFORMATION: Synthetic Construct
```

```
<400> SEQUENCE: 44

Gly Gly Gly Gly Pro Lys Lys Lys Arg Lys Val Gly Gly
1               5                   10

<210> SEQ ID NO 45
<211> LENGTH: 13
<212> TYPE: PRT
<213> ORGANISM: Artificial
<220> FEATURE:
<223> OTHER INFORMATION: Synthetic Construct

<400> SEQUENCE: 45

Gly Gly Gly Phe Ser Thr Ser Leu Arg Ala Arg Lys Ala
1               5                   10

<210> SEQ ID NO 46
<211> LENGTH: 17
<212> TYPE: PRT
<213> ORGANISM: Artificial
<220> FEATURE:
<223> OTHER INFORMATION: Synthetic Construct

<400> SEQUENCE: 46

Cys Lys Lys Lys Lys Lys Ser Glu Asp Glu Tyr Pro Tyr Val Pro
1               5                   10                  15

Asn

<210> SEQ ID NO 47
<211> LENGTH: 28
<212> TYPE: PRT
<213> ORGANISM: Artificial
<220> FEATURE:
<223> OTHER INFORMATION: Synthetic Construct

<400> SEQUENCE: 47

Cys Lys Lys Lys Lys Lys Lys Ser Glu Asp Glu Tyr Pro Tyr Val
1               5                   10                  15

Pro Asn Phe Ser Thr Ser Leu Arg Ala Arg Lys Ala
            20                  25

<210> SEQ ID NO 48
<211> LENGTH: 25
<212> TYPE: PRT
<213> ORGANISM: Artificial
<220> FEATURE:
<223> OTHER INFORMATION: Synthetic Construct

<400> SEQUENCE: 48

Leu Val Arg Lys Lys Arg Lys Thr Glu Glu Glu Ser Pro Leu Lys Asp
1               5                   10                  15

Lys Asp Ala Lys Lys Ser Lys Gln Glu
            20                  25

<210> SEQ ID NO 49
<211> LENGTH: 30
<212> TYPE: PRT
<213> ORGANISM: Artificial
<220> FEATURE:
<223> OTHER INFORMATION: Synthetic Construct

<400> SEQUENCE: 49

Lys Lys Lys Lys Lys Lys Lys Lys Lys Lys Lys Lys Lys Lys Lys
1               5                   10                  15

Lys Lys Lys Lys Lys Lys Lys Gly Gly Lys Lys Lys Lys Lys
```

<210> SEQ ID NO 50
<211> LENGTH: 22
<212> TYPE: DNA
<213> ORGANISM: Artificial
<220> FEATURE:
<223> OTHER INFORMATION: Synthetic Construct Positions 1,2,5,6 are
      pseudocytosine; amino acid linker between positions 11-12;
      formylated Cysteine at 5' end

<400> SEQUENCE: 50
ccttcctttt tttttttcctt ck                                              22

<210> SEQ ID NO 51
<211> LENGTH: 10
<212> TYPE: PRT
<213> ORGANISM: Artificial
<220> FEATURE:
<223> OTHER INFORMATION: Synthetic Construct

<400> SEQUENCE: 51

Gly Ala Ala Gly Gly Ala Ala Ala Ala Ala
1               5                   10

<210> SEQ ID NO 52
<211> LENGTH: 15
<212> TYPE: DNA
<213> ORGANISM: Artificial
<220> FEATURE:
<223> OTHER INFORMATION: Cysteine at 5' end

<400> SEQUENCE: 52
ctagactcgg accct                                                       15

<210> SEQ ID NO 53
<211> LENGTH: 13
<212> TYPE: PRT
<213> ORGANISM: Artificial
<220> FEATURE:
<223> OTHER INFORMATION: Synthetic Construct

<400> SEQUENCE: 53

Gly Tyr Arg Ala Arg Pro Lys Phe Lys Ala Gly Lys Arg
1               5                   10

<210> SEQ ID NO 54
<211> LENGTH: 12
<212> TYPE: PRT
<213> ORGANISM: Artificial
<220> FEATURE:
<223> OTHER INFORMATION: Synthetic Construct

<400> SEQUENCE: 54

Arg Pro Ala Lys Arg Val Arg Ile Arg Ser Lys Lys
1               5                   10

<210> SEQ ID NO 55
<211> LENGTH: 14
<212> TYPE: PRT
<213> ORGANISM: Artificial
<220> FEATURE:
<223> OTHER INFORMATION: Synthetic Construct

<400> SEQUENCE: 55

Ser Ser Thr Ser Thr Thr Ala Lys Arg Lys Lys Arg Lys Leu
1               5                   10

<210> SEQ ID NO 56
<211> LENGTH: 9
<212> TYPE: PRT
<213> ORGANISM: Artificial
<220> FEATURE:
<223> OTHER INFORMATION: Synthetic Construct

<400> SEQUENCE: 56

Met Leu Arg Lys Arg Arg Lys Arg Leu
1               5

<210> SEQ ID NO 57
<211> LENGTH: 13
<212> TYPE: PRT
<213> ORGANISM: Artificial
<220> FEATURE:
<223> OTHER INFORMATION: Synthetic Construct

<400> SEQUENCE: 57

Met Arg His Lys Arg Ser Ala Lys Arg Thr Lys Arg Ala
1               5                   10

<210> SEQ ID NO 58
<211> LENGTH: 12
<212> TYPE: DNA
<213> ORGANISM: Artificial
<220> FEATURE:
<223> OTHER INFORMATION: Synthetic Construct

<400> SEQUENCE: 58
taatacgact ca                                                         12

<210> SEQ ID NO 59
<211> LENGTH: 12
<212> TYPE: DNA
<213> ORGANISM: Artificial
<220> FEATURE:
<223> OTHER INFORMATION: Synthetic Construct Cysteine at 5' end

<400> SEQUENCE: 59
tgagtcgtat ta                                                         12

<210> SEQ ID NO 60
<211> LENGTH: 15
<212> TYPE: PRT
<213> ORGANISM: Artificial
<220> FEATURE:
<223> OTHER INFORMATION: Synthetic Construct Cysteine at 5' end

<400> SEQUENCE: 60

Lys Glu Ser Arg Ala Lys Lys Phe Gln Arg Gln His Met Asp Ser
1               5                   10                  15

COMPOSITIONS WITH MODIFIED NUCLEASES TARGETED TO VIRAL NUCLEIC ACIDS AND METHODS OF USE FOR PREVENTION AND TREATMENT OF VIRAL DISEASES

CROSS-REFERENCE TO RELATED APPLICATIONS

This application claims priority to, and is a continuation of, U.S. patent application Ser. No. 11/578,716 (filed Oct. 13, 2006) which is a national stage entry of International Patent application PCT/US05/12532 (filed Apr. 14, 2005) which claims priority to U.S. provisional patent application 60/561,934 (filed Apr. 14, 2004). The entirety of each of these applications are hereby incorporated herein by reference.

REFERENCE TO A SEQUENCE LISTING

This application refers to a "Sequence Listing" listed below, which is provided as an electronic document filed herewith. This document is incorporated herein by reference in its entirety.

BACKGROUND OF THE INVENTION

This disclosure relates to new compositions comprising chemically and genetically modified nucleases targeted to cleave viral nucleic acids present during a viral replication cycle, and to methods of using hydrolytic properties of nucleases for prevention and treatment of diseases caused by human, animal, and plant viruses.

There is an increasing need for safe and effective antiviral agents for prevention and treatment of existing and emerging life threatening viral diseases.

DNase I inhibits synthesis and replication of viral double-stranded (ds) DNA in cells infected with vaccinia virus, human herpes virus, cytomegalovirus and adenovirus without affecting synthesis of cellular genomic DNA and integrity of the treated cells (Trukhachev and Salganik, Virology 33, 552, 1967; Salganik et al., Dokl. Akad. Nauk SSSR (Proc. USSR Acad. Sci.) 180: 1473-1476, 1968; Lapik, et al., Pharmac. Toxicol. 2: 210, 1970; Salganik, Current Trends in Life Sciences, 12: 115-119, 1984). Bovine pancreatic RNase A has been shown to inhibit viral replication in cells infected with influenza, tick-born encephalitis and poliomyelitis and viruses (LeClerc, Nature 177:578-579 (1956); Salganik, Current Trends in Life Sciences, 12: 115-123, 1984). Therapeutic activity of native bovine pancreatic DNase I against human herpes and adenoviruses and bovine pancreatic RNase A against tick-borne encephalitis and influenza viruses have been demonstrated in clinical trials (Salganik et al., Nature 214, 100, 1967; Gutarov et al., Zhurn. Nevropath. Psychiatry. 11, 75-78, 1976; Glukhov et al., Arch. Neurol. 33: 598-603, 1976). Bovine pancreatic DNase I directed against dsDNA-parvovirus combined with the bovine pancreatic RNase A directed against ssRNA-paramixovirus have been shown effective in treatment of dogs infected by both viruses (U.S. Pat. No. 5,484,589 to Salganik).

Certain RNases such as cytotoxic Onconase™ isolated from oocytes and embryos of Northern Leopard Frog (*Rana pipiens*) and bovine seminal RNase A (BS-RNase) have been shown also to moderately inhibit replication of HIV-I in cell culture (Youle, et al., Proc. Natl. Acad. Sci. USA 91, No. 13: 6012-6016, 1994; Saxena, et al. J. Biol. Chem. 271: 20783-20788, 1996; Huang, et al., Proc. Natl. Acad. Sci. USA 96: 2678-2681, 1999).

These studies of antiviral properties of native bovine pancreatic DNase I and RNase A do not address the shortcomings of native nucleases such as high susceptibility to endogenous proteolytic degradation, low cellular uptake, short half-life and others. Further, those studies, do not address major issues for antiviral therapeutics such as a likelihood development of viral resistance during treatment by nucleases.

The earlier approach to utilizing hydrolytic properties of DNase I and RNase A against viral nucleic acids was limited to targeting double-stranded viral genomic DNA or single-stranded viral genomic RNA within infected cells, however multiple forms of intermediate viral nucleic acids such as linear, circular or super-coiled dsDNA, ssDNA, dsRNA or ssRNA as well as hybrid RNA-DNA, which appear in the course of the replication cycle of targeted viruses were not considered.

The discussion above is merely provided for general background information and is not intended to be used as an aid in determining the scope of the claimed subject matter.

BRIEF DESCRIPTION OF THE INVENTION

Antiviral compositions comprising a modified nuclease, or a plurality of such modified nucleases having at least one non-natural amino acid residue substituted for a naturally occurring amino acid in a parent nuclease are provided, as are methods of use and kits providing unit dosages of such compositions.

In a first embodiment, a method for treating a viral disease in a subject is provided. The method comprising: administering to the subject a composition for destruction of targeted nucleic acids inside biological cells, the composition comprising: a core carrier comprising a plurality of first multivalent molecular scaffolds and a plurality of second multivalent molecular scaffolds, each of the first and second multivalent molecular scaffolds being covalently bound to the core carrier, each first and second multivalent molecular scaffold comprising a polymer, at least one of the first multivalent molecular scaffolds further comprising a plurality of cell membrane permeating peptides covalently bound to the first multivalent molecular scaffold for effective internalization of the composition into cytoplasm of the biological cells, wherein the first multivalent molecular scaffolds are nuclease-free, at least one of the second multivalent molecular scaffolds comprising a plurality of nucleic acid targeting ligands covalently bound to the second multivalent molecular scaffold that is capable of binding specific sequences on targeted nucleic acids inside the biological cells, at least one nuclease covalently bound to the second multivalent molecular scaffold that is capable of destruction of the targeted nucleic acids that are bound to the nucleic acid targeting ligands inside the biological cells.

In a second embodiment, a composition for destruction of targeted nucleic acids inside biological cells is provided. The composition comprising: a core carrier comprising a plurality of multivalent molecular scaffolds, at least one such multivalent molecular scaffold further comprising: a plurality of membrane permeating peptides for effective internalization of the composition into cytoplasm of the biological cells, a plurality of nucleic acid targeting ligands capable of binding specific sequences on targeted nucleic acids inside the biological cells, at least one nuclease capable of destruction of the targeted nucleic acids that are bound to the nucleic acid targeting ligands inside the biological cells, the at least one nuclease being modified to comprise at least one non-natural amino acid residue that has greater affinity and hydrolytic activity toward the targeted nucleic acids than a corresponding unmodified parent nuclease.

In a third embodiment, a method of destroying targeted nucleic acids inside of a cell is provided. The method comprising steps of: administering to a biological organism a composition for destruction of nucleic acids inside a targeted cell, the composition comprising: a core carrier comprising a plurality of multivalent molecular scaffolds, at least one such multivalent molecular scaffold further comprising: a plurality of membrane permeating peptides for effective internalization of the composition into cytoplasm of the biological cells, a plurality of nucleic acid targeting ligands capable of binding specific sequences on targeted nucleic acids inside the biological cells, at least one nuclease capable of destruction of the targeted nucleic acids that are bound to the nucleic acid targeting ligands inside the biological cells; permitting the composition to penetrate a membrane of the targeted cell; permitting the nuclease of the composition to interact with polynucleic acids within the targeted cell to destroy the polynucleic acids.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
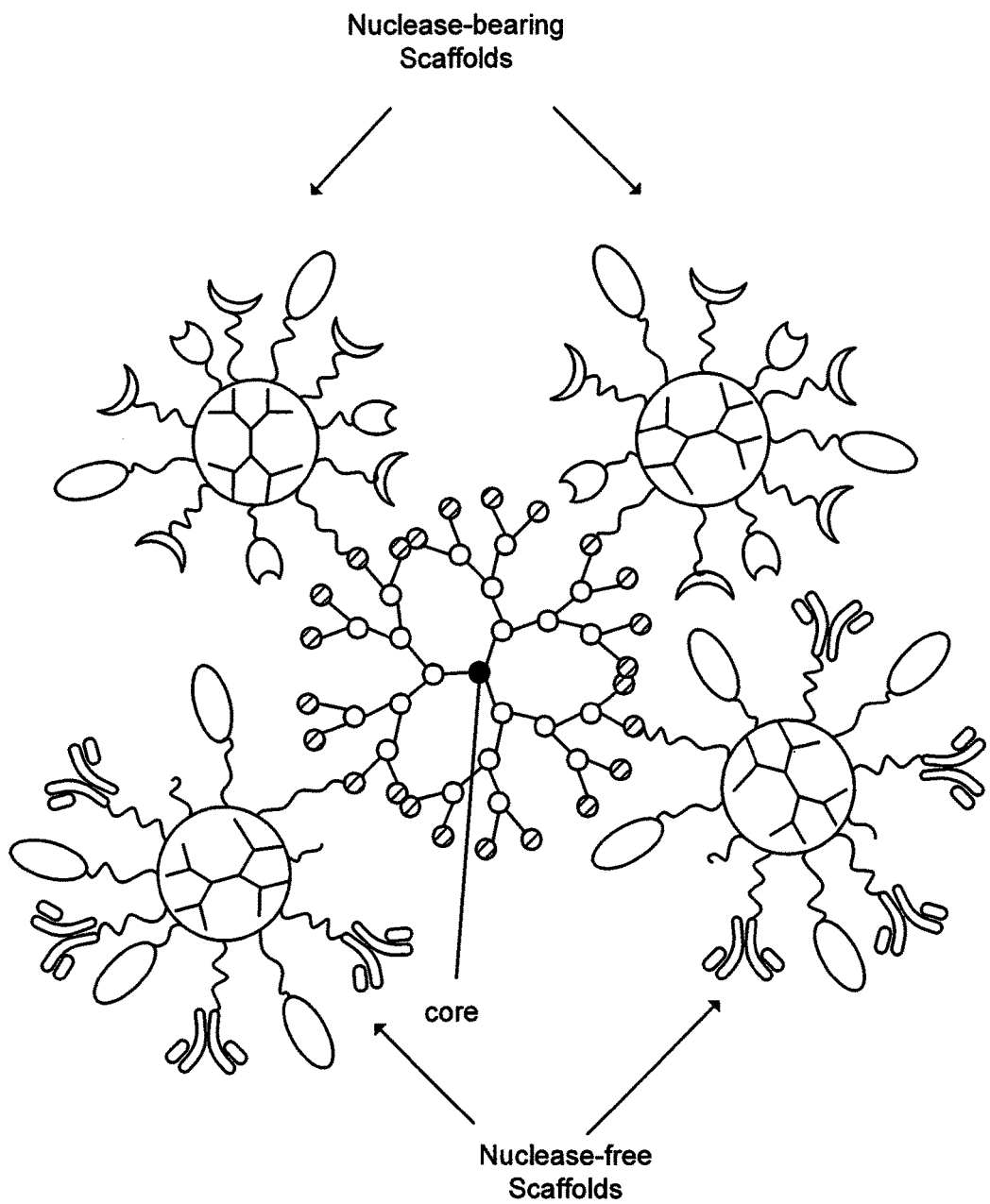
FIG. 1 depicts a multivalent shell-core with a plurality of multivalent molecular scaffolds.

An embodiment of the invention provided herein is an antiviral composition comprising a modified nuclease, wherein at least one amino acid in the amino acid sequence of the modified nuclease is a non-natural amino acid residue that is substituted for a naturally-occurring amino acid in the amino acid sequence of a parent nuclease, wherein the modified nuclease has greater hydrolytic activity than the parent nuclease. The substituted non-natural amino acid in alternative embodiments is a keto or a thiol side chain group. In general, the non-natural amino acid is located at the N- or C-terminus of the amino acid sequence of the nuclease.

In an alternative embodiment, the non-natural amino acid is located in position of the sequence comprising a substrate nucleic acid binding domain of the nuclease. In general, the substituted non-natural amino-acid residue comprises a multiply-charged side chain group. The modified nuclease has increased affinity for the substrate nucleic acid compared to the parent nuclease.

In an alternative embodiment, the non-natural amino acid residue is in a position of the amino acid sequence of the parent nuclease comprising a binding domain for a modulator of activity of the nuclease. The modulator in a related embodiment is an inhibitor of the nuclease activity, for example, the modulator is a protease. The substituted non-natural amino acid residue comprises a bulky neutral or charged side chain group. The keto or thiol side chain group is covalently attached to a neutral steric hindrance or multiply-charged moiety. The neutral steric hindrance moiety is a bulky organic moiety or a polymer, and the moiety is selected from the group of dendrimers, charged gold nanoparticles, non-natural amino acid residues with multiply-charged side chains, oligomers of natural and non-natural amino acid residues with single-charged side chains, mannose 6-phosphate residues and oligomers of mannose 6-phosphate residues.

The antiviral composition has greater hydrolytic activity towards a substrate nucleic acid in the presence of the modulator compared to the parent nuclease. In certain embodiments, the parent nuclease is of biological origin, selected from for example an origin in a mammal, an amphibian, a bacterium, an insect and a plant. In alternative embodiments, an exemplary parent nuclease is selected from human DNase I (ref. SWISS PROT P24855) and bovine DNase I (ref. SWISS PROT P00639). The amino acid residue and its position in the amino acid sequence of the non-natural amino acid within DNA binding domains of human or bovine DNase I are: Arg(R)9 or Gln(Q).sub.9, Glu(E)13, Thr(T)14, Ser(S)43, His(H)44, Asn(N)74, Arg(R) 111, Asn(N)170, Ser(S)206, Thr(T)207, and Tyr(Y)211. The modified DNase I has at least about 3-fold greater hydrolytic activity than the parent nuclease wherein the substrate is double-stranded viral DNA.

The modulator in certain embodiments is an inhibitor of the DNase I activity, for example, the modulator is G-actin. The non-natural amino acid comprises a bulky neutral or charged side chain group, and is a residue and location in a position within the G-actin binding domain of a human or a bovine DNase I, selected from at least one of the group consisting of: His(H)44, Leu(L)45, Val(V)48, Gly(G)49, Leu(L)52, Asp(D)53, Asn(N)56, His(H)64 or Tyr(Y)65, Val(V)66, Val(V)67, Ser(S)68, Glu(E)69, Ser(S)94, Tyr(Y) 96, and Ala(A)114. The modified DNase I has at least about 10-fold greater hydrolytic activity towards double-stranded DNA in the presence of a physiological concentration of G-actin than the parent nuclease. In a related embodiment, the modified DNase I has substitutions in the residues at positions in the amino acid sequence of the parent human DNase I: Q11RU/E13KU$^{(2+)}$/N74KU$^{(2+)}$/A114FU$^{(keto)}$, wherein RU is non-natural homoarginine, KU$^{(2+)}$ is nonnatural lysine with two positively charged side-chain amino groups and $FU^{(keto)}$ is non-natural p-acetyl-L-phenylalanine residue carrying a keto group.

In alternative embodiments, the parent nuclease is selected from the group of RNase A-like nucleases comprising human RNase I (ref. SWISS PROT P07998), bovine RNase A (ref. SWISS PROT P00656), RNase S derivative of human RNase I, and RNase S derivative of bovine RNase A. The parent nuclease comprises a binding domain for a modulator which is an inhibitor which is endogenous RNase inhibitor (RI). The modified RNase comprises at least 3-times greater hydrolytic activity towards single-stranded RNA in the presence of a physiological concentration of the RI compared to the parent nuclease. The non-natural amino acid is a bulky neutral or charged side chain group, and is a residue and location in a position within the RI binding domains of RNase consisting of at least one selected from the group of: Lys(K)1, Lys(K)7, Gln(Q)11, Asn(N)71, Asp (E)111, and from Arg(R)85 to Asn(N)94 of the parent nuclease.

The modified human RNase I comprises substitutions in positions selected from parent human RNase I: $K1FU^{(keto)}$/ Q11A/N71A/E111A, wherein $FU^{(keto)}$ is non-natural p-acetyl-L-phenylalanine residue carrying a keto group. The modified human RNase S comprises substitutions selected from positions of a peptide fragment having positions 1-15 in the amino acid sequence of the parent human RNase I: $K1FU^{(keto)}$/Q11A; and truncated S-protein positions 21-124 amino acid: N71A/G89$FU^{(keto)}$/E111A, wherein $FU^{(keto)}$ is non-natural p-acetyl-L-phenylalanine residue carrying a keto group.

In an alternative embodiment, the parent nuclease is an artificial nuclease. The artificial nuclease is a molecular scaffold comprising at least one recognition domain for a substrate nucleic acid and at least one catalytic domain for hydrolysis of the phosphodiester bonds of a substrate nucleic acid. In alternative related embodiments, the molecular scaffold is a synthetic peptide, peptide oligomer or peptide dendrimer. The synthetic peptide is a hydrolytic oligopeptide comprising hydrolytically-functional amino acids: Arg, Asp, Cys, His, Lys, Ser, Tyr and Trp, and further comprising amino acids: Ala, Gly, Leu, Phe. Accordingly, the hydrolytic oligopeptide is a dipeptide or tripeptide selected from the group consisting of: Ser-His, His-Asp, Cys-His, Ser-His-Asp, Ser-His-Gly, Ser-His-His, and His-Phe-Asp. For example, the hydrolytic oligopeptide is a hexapeptide having an amino acid sequence selected from the group consisting of: Gly-Phe-Ser-Leu-His-Ala (SEQ ID NO: 10), Phe-Ser-Phe-Leu-His-Ala (SEQ ID NO:11), and Ser-Ser-Phe-Leu-His-Ala (SEQ ID NO:12). Alternatively, the hydrolytic oligopeptide is an undecapeptide selected from the group consisting of: Ser-Gly-Gly-His-Gly-Gly-Arg-Gly-Gly-His-Phe (SEQ ID NO: 14), Ser-Gly-Gly-Ser-Gly-Gly-Ser-Gly-Gly-His-Phe (SEQ ID NO:15), Ser-Gly-Gly-Arg-Gly-Gly-His-Gly-Gly-His-Phe (SEQ ID NO: 16).

In these embodiments, the molecular scaffold is a polypeptide, and the nucleic acid recognition domain and the catalytic domain are embedded within a structural unit of the polypeptide. Further, the catalytic domain specifically binds a hydrolytic metal, wherein the metal is a lanthanide.

In alternative embodiments, the polypeptide is a hydrolytic polypeptide selected from the group comprising: TERRRQQLDKDGDGTIDEREIKIHFQNKRAKIK (SEQ ID NO: 4), TERRRFDKDQNGYIGAADLRHVKIWFQNK-RAKIK (SEQ ID NO: 5), TERRRFRVFDKDGNGY-ISAAEKIWFQNKRAKIK (SEQ ID NO: 6), TRRRRF-SLFDKDGDGTITTKEEVWFQNRRMKWK (SEQ ID NO: 7), and DEKRPRTAFSGEQLARLKREFNENRYL-TERRRLRVFDKDGNGFISAAEKIWFQN KR AKIKKST (SEQ ID NO: 8).

In general, the molecular scaffold is a polymeric carrier with multiple attachment sites comprising the nucleic acid recognition domain and the catalytic domain attached to separate sites of the polymeric carrier. The nucleic acid recognition domain is selected from the group comprising sequence-specific modified oligonucleotides, zinc fingers, and hairpin polyamides. The catalytic domain is a metal-binding peptide or a synthetic metal complex. Further, the metal binding peptide is Zn(II)-binding peptide: Asp-Pro-Asp-Glu-Leu-Glu-His-Ala-Ala-Lys-His-Glu-Ala-Ala-Ala-Lys-$CONH_2$ (SEQ ID NO: 9). The synthetic metal complexes are selected from the group of: dicerium complex $Ce_2$(HXTA=5-methyl-2-hydroxy-1.3-xylene-a,a-diamine-N,N,N',N'-tetrace-tic acid), lanthanide complexes of polyalcohol and macrocyclic ligands, Co(III) complexes of polyamine ligands, Fe(II)-bleomycin complex, Cu(II) complexes of kanamycin and neamine.

Also provided herein is an antiviral composition represented by formula Nuc-$(T^b)_r$, wherein Nuc comprises a nuclease covalently associated with at least one targeting ligand $(T^b)_r$, wherein b is an integer from 1 to 8 that relates to the type of the ligand, and r is integer from 1 to 4 that relates to the quantity of each type of the ligand. Accordingly, formula $(T^b)_r$-$P_m$-H further comprises at least one targeting ligand $(T^b)_r$ wherein the ligand is covalently associated with a polymer $P_m$ of m units of monomer P, wherein m is an integer from 1 to 2000, wherein $P_m$ is covalently linked to a non-polar moiety H.

Also provided herein is an antiviral composition represented by a formula Nuc-H, wherein Nuc comprises a nuclease covalently associated with a non-polar moiety H, and H is selected from the group of hydrocarbons consisting of alkyl, aryl, substituted alkyl and substituted aryl chains. Accordingly, in the formula Nuc-H-$(T^b)_r$, the composition is further covalently linked with at least one targeting ligand $(T^b)_r$, wherein b is an integer from 1 to 8 that relates to the type of the ligand, and r is integer from 1 to 4 that relates to the quantity of each type of the ligand.

Also provided herein is an antiviral composition represented by formula $(Nuc^a)_q$-$P_n$-H comprising at least one nuclease moiety $(Nuc^a)_q$, wherein a is an integer from 1 to 3 that relates to the type of the nuclease and q is an integer from 1 to 50 that relates to the quantity of each nuclease, and Nuc being covalently associated with a polymer $P_n$ of n units of monomer P, wherein n is an integer from 1 to 2000, and $P_n$ is covalently linked to a non-polar moiety H.

Figure 2:
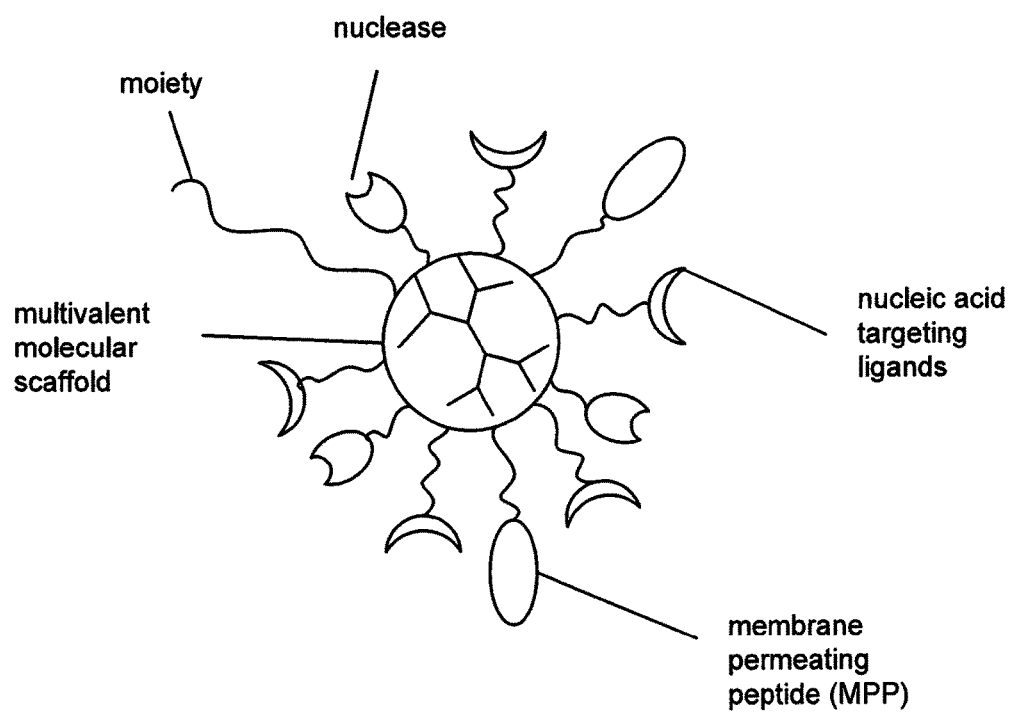
FIG. 2 is schematic depiction of an example of a nuclease-bearing scaffold.

Also provided herein is an antiviral composition represented by formula $(Nuc^a)_q$-$P_n$-H-$P_m$-$(T^b)_r$ comprising two of the compositions above that are covalently linked to each other. Thus in the formula [$(Nuc^a)_q$-$P_n$-H]$_i$-D-[H-$P_m$-$(T^b)_r$]$_k$ there is a composition in which i and k relate to the quantity of each type of the composition and are integers from 1 to 8, and each composition is further non-covalently linked to a hydrophobic core platform D (see FIG. 1) via non-polar moiety H (see FIG. 2), wherein D is a dendrimer modified to include an extended hydrophobic core.

Also provided is an antiviral composition represented by formula $(Nuc^a)_q$-$P_n$-H-$L^a_{(+)}$ as above, further covalently linked to a modified oligonucleotide $L^a_{(+)}$ having a nucleotide sequence capable of base pairings, wherein $L^a_{(+)}$ hybridizes to an oligonucleotide $L^a_{(-)}$ having a respective complementary nucleotide sequence. Also provided is an antiviral composition represented by formula $(T^b)_r$-$P_m$-H-$L^b_{(+)}$, covalently linked to a modified oligonucleotide $L^b_{(+)}$ having a unique nucleotide sequence capable of base pairings, wherein the nucleotide sequence of $L^b_{(+)}$ hybridizes to a respective complementary oligonucleotide $L^b_{(-)}$.

Also provided is an antiviral composition represented by formula $[(Nuc^a)_q-P_n-H-L^a_{(+)}]_k-[(L^a_{(-)})_k-D_c-(L^b_{(-)})_i]-[L^b_{(+)}-H-P_m-(T^b)_r]_i$ according to the compositions above, wherein i and k relate to the quantity of each type of the composition and are integers from 1 to 8, wherein $L^a_{(+)}$ or $L^b_{(+)}$ hybridize to their respective complementary oligonucleotides $L^a_{(-)}$ or $L^b_{(-)}$ covalently linked to a multivalent molecular scaffold $D_c$ having a finite number of attachment sites, wherein c is a number of attachment sites and is an integer from 4 to 64.

The formula $[(Nuc^a)_q-P_n-H-]_k-D_s-L^a_{(+)}$ can further have a plurality of compositions covalently linked to a multivalent molecular scaffold $D_s$ having a finite number of attachment sites, wherein s is a number of attachment sites and is an integer from 4 to 64, wherein $D_s$ is further covalently linked to a modified oligonucleotide $L^a_{(+)}$ having a unique nucleotide sequence capable of base pairings. In any of the above, the nuclease Nuc is selected from the group consisting of a wild-type native nuclease, a genetically modified nuclease, a chemically and genetically modified nuclease of biological origin, and an artificial nuclease.

The formula $[(T^b)_r-P_m-H]_i-D_s-L^b_{(+)}$ can further have a plurality of the compositions covalently linked to a multi-valent molecular scaffold $D_s$ having a finite number of attachment sites, wherein s is a number of attachment sites and is an integer from 4 to 64, and wherein $D_s$ is further covalently linked to a modified oligonucleotide $L^a_{(+)}$ having a unique nucleotide sequence capable of base pairings.

An embodiment of the invention provides an antiviral composition with the formula $\{[(Nuc^a)_q-P_n-H]_k-D_s-L^a_{(+)}\}_j-[L^a_{(-)}]_j-D_c-[(L^b_{(-)})_f\{[L^b_{(+)}-D_s-[H-P_n-(T^b)_q]\}_f$ wherein j and f relate to the quantity of each moiety and are integers from 1 to 8, wherein each composition is linked to a modified oligonucleotide $L^a_{(-)}$ or $L^b_{(-)}$ having a unique nucleotide sequence capable of base pairings and undergoing hybridization with their respective complementary oligonucleotides $L^a_{(+)}$ or $L^b_{(+)}$, and wherein $L^a_{(-)}$ and $L^b_{(-)}$ are further covalently linked to a multivalent molecular scaffold $D_c$ with a finite number of attachment sites, wherein c is the number of attachment sites of $D_c$ and is an integer from 4 to 64.

In any of the above, the polymer is selected from the group consisting of PEG [poly(ethylene glycol)], PEG-PLA (poly-lactic acid), PEG-PLGA (poly-lactic-glycolic acid), and PEG-PLLA (poly-L-lactic acid), HPMA[N-(2-hydroxypropyl)methacrylamide]copolymer, and PEI [poly(ethyleneimine)]. The polymer has a configuration selected from linear, branched, forked or star-like.

The antiviral compositions herein can further have at least one hydrolysable linker.

The multivalent molecular scaffold $D_c$ or $D_s$ of the antiviral compositions herein is, in related embodiments, a dendrimer. For example, the dendrimer is selected from the group consisting of poly(aminoamine)PAMAM, PAMAM (ethylenediamine-EDA), and poly(lysine) dendrimers.

Further, the complementary oligonucleotides are, in various embodiments, $L^{a,b}_{(+)}$ and $L^{a,b}_{(-)}$ are Locked Nucleic Acids (LNA), Bridged Nucleic Acids (BNA), Peptide Nucleic Acids (PNA), bis-PNA, hydroxyproline PNA (HypNA), serine PNA (SerNA), hairpin polyamides, morpholino oligos, phosphorothioate (PS) oligos, or pyrrolidine-amide oligonucleotide mimic (POM). In general as used herein, each oligonucleotide $L^a_{(-)}$ and $L^b_{(-)}$, or a respective complementary oligonucleotides $L^a_{(+)}$ or $L^b_{(+)}$, has a unique nucleotide sequence, i.e., the sequence is not found in the genome of the subject to be treated, and the nucleotide sequence is further linked to a bi-functional chemical reagent forming a covalent bond formation between the hybridized oligonucleotides. The bi-functional chemical reagent has a dormant chemical group that is activated for covalent bond formation between the hybridized oligonucleotides. The dormant chemical group comprises an aromatic β-chloroethyl alkylating group inhibited by a neighboring formyl residue, and the aromatic β-chloroethyl alkylating group is chemically activated through reduction of the formyl residue using sodium borohydride to form the covalent bond between the hybridized oligonucleotides. In certain embodiments, the dormant chemical group is a photoactive cross-linker is selected from the group consisting of azides, psoralens or porphyrins. In a related embodiment, the dormant azide, psoralen or porphyrin cross-linker further is photoactivated to form a covalent bond between the hybridized oligonucleotides.

The targeting ligand $T^b$ in certain embodiments is selected from the group of oligomers having nucleotide sequence-specific binding affinity to a viral nucleic acid and further consisting of: peptide nucleic acid (PNA), bis-PNA, hydroxyproline PNA (HypNA), serine PNA (SerNA), Locked Nucleic Acid (LNA), Bridged Nucleic Acids (BNA), hairpin polyamides, morpholino oligos, phosphorothioate (PS) oligos, pyrrolidine-amide oligonucleotide mimic (POM), and an oligopeptide having a sequence of a zinc finger. The targeting ligand $T^b$ is selected from the group of sequence-specific nucleic acid binding proteins comprising designed zinc finger proteins (ZFP) and arginine-rich peptides. Alternatively, the targeting ligand $T^b$ is a membrane permeating peptide or polypeptide. The membrane permeating peptide is selected from the group consisting of: basic poly(Arg) and poly(Lys) peptides; basic poly(Arg) and poly(Lys) peptides containing non-natural analogs of arginine and lysine residues; and Arg(R)/Lys(K)-rich peptides derived from genes. The basic poly(Arg) peptide in certain related embodiments contains 6-10 Arg-residues. In a set of alternative embodiments, the Arg/Lys-rich peptide is selected from the group of peptides consisting of: YGRKKRPQRRR (HIV $TAT_{47-57}$; SEQ ID NO: 17); RQIKIWFQNRRMKWKK (Drosophila Antennapedia (ANTp16); SEQ ID NO: 18); RRWRRWWRRWWRRWRR (W/R; SEQ ID NO 19); $CWK_{18}$ ($AlkCWK_{18}$; SEQ ID NO: 20); $K_{18}WCCWK_{18}$ (Di-$CWK_{18}$; SEQ ID NO: 21); WTLNSAGYLLGKINLKALAALAKKIL (Transportan; SEQ ID NO 22); GLFEALEELWEAK (DipaLytic; SEQ ID NO: 23); $K_{16}$GGCRGDMFGCAK$_{16}$RGD ($K_{16}$RGD; SEQ ID NO: 24); K16GGCMFGCGG (P1; SEQ ID NO: 25); $K_{16}$ICRRARGDNPDDRCT (P2; SEQ ID NO: 26); KKWKMRRNQFWVKVQRbAK (B) bA (P3; SEQ ID NO 27); VAYISRGGVSTYYSDTVKGRFTRQKYNKRA (P3a; SEQ ID NO: 28); IGRIDPANGKTKYAPKFQDKATRSNYYGNSPS (P9.3; SEQ ID NO: 29); KETWWETWWTEWSQPKKKRKV (Pep-1; SEQ ID NO: 30); PLAEIDGIELTY (Plae; SEQ ID NO: 31); $K_{16}$GGPLAEIDGIELGA (Kplae; SEQ ID NO: 32); $K_{16}$GGPLAEIDGIELCA (cKplae; SEQ ID NO: 33); GALFLGFLGAAGSTMGAWSQPKSKRKV (MGP; SEQ ID NO 34); WEAK(LAKA)$_2$-LAKH(LAKA)$_2$LKAC(HA2; SEQ ID NO: 35); (LARL)$_6$NHCH$_3$(LARL4$_6$; SEQ ID NO 36); KLLKLLLKLWLLKLLL (Hel-11-7; SEQ ID NO 37); (KKKK)$_2$GGC (KK; SEQ ID NO: 38); (KWKK)$_2$GCC (KWK; SEQ ID NO: 39); (RWRR)$_2$GGC(RWR; SEQ ID NO: 40); PKKKRKV (SV40 NLS7; SEQ ID NO: 41); PEVKKKRKPEYP (NLS12; SEQ ID NO: 42); TPPKKKRKVEDP (NLS12a; SEQ ID NO: 43); GGGGPKKKRKVGG (SV40 NLS13; SEQ ID NO 44); GGGFSTSLRARKA (AV NLS13; SEQ ID NO: 45); CKKKKKKSEDEYPYVPN (AV RME NLS17; SEQ ID NO: 46); CKKKKKKKSEDEY-PYVPNFSTSLRARKA (AV FP NLS28; SEQ ID NO 47); LVRKKRKTEEESPLKDKDAKKSKQE (SV40 N1 NLS24; SEQ ID NO: 48); and K$_9$K$_2$K$_4$K8GGK$_5$ (Loligomer; SEQ ID NO: 49). Alternatively, the membrane permeating polypeptide is selected from the group of polypeptides comprising: HSV-1 tegument protein VP22; HSV-1 tegument protein VP22r fused with nuclear export signal (NES); mutant B-subunit of E. coli enterotoxin EtxB (H57S); detoxified exotoxin A (ETA), and analogs thereof. In related embodiments, to decrease or to avoid proteolytic digestion of the oligopeptides the amino acid sequence comprises D-amino acids; in other embodiments, the sequences herein are envisioned to comprise all or substantially all D-amino acids.

Figure 3:
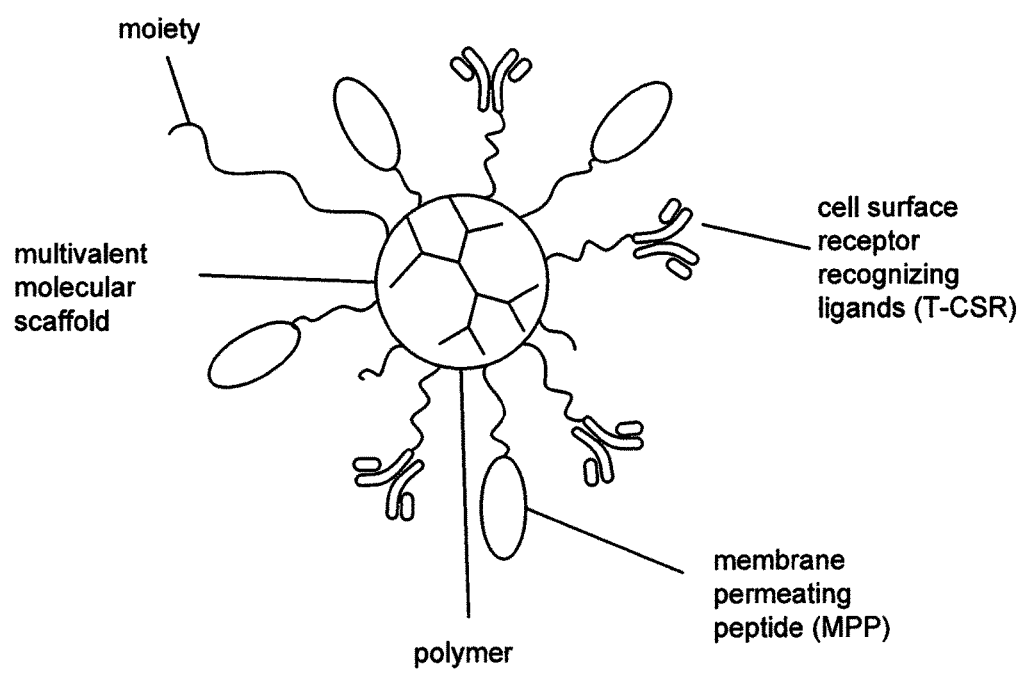
FIG. 3 is a schematic depiction of an example of a nuclease-free scaffold.

The targeting ligand T$^b$ (see FIG. 3) is selected from the group consisting of ligands of host cell surface receptors (CSR) expressed by a T cell in the host cell (T-CSR), i.e., the virus host cells (T-CSR). For example, the T-CSR is a selected from the group of receptors for steroids and mimetic or derivatives, the receptors comprising those for steroids such as cortisol, corticosterone, glucocorticoid dexametasone and others. The T-CSR is a peptide derived from a viral nuclear capsid protein selected from the group of: heparan sulfate receptor binding peptides: HPV 31 L1 Cta: GYRARPKFKAGKR SEQ ID NO: 53; HPV 45 L1 Ctb: RPAKRVRIRSKK: (SEQ ID NO: 54); hpv-16 11 Cta: SSTSTTAKRKKRKL (SEQ ID NO: 55); HPV-16 L2 Ct: MLRKRRKRL (SEQ ID NO: 56) HPV-16 L2 Nt: MRH-KRSAKRTKRA (SEQ ID NO: 57). Alternatively, the T-CSR is selected from the group of synthetic peptides derived from viral envelope proteins comprising: T-peptide: ASTTTNYT (SEQ ID NO: 1), and D-Ala-T-peptide-Amide (DAPTA). In related embodiments, the T-CSR is a folate derivative. In related embodiments, the T-CSR further comprises a ligand host cell receptor selected of the group of monosaccharides: D-mannose, D-Glucose, L-galactose, L-fucose (6-deoxygalactose), N-acetylglucosamine, N-acetylgalactosamine, N-acetylneuraminic acid (sialic acid), and N-acetylmuramic acid, derivatives of L-fucose and D-mannose occupying the carbon-6 position such as D-mannose-6-phosphate, L-fucosyl-lactose, D-mannitol, mannan and their analogs.

The targeting ligand $T^b$ in certain embodiments is a CSR-derivative having binding affinity to a viral glycoprotein expressed on the membrane of virus-infected cell. For example, the CSR-derivative is a T-cell receptor such as a CD4 or a CD8 or other. Further in certain embodiments, the CSR-derivative is a chemokine receptor such as a CXCR4 or a CCR5. In certain embodiments, targeting ligand $T^b$ is an inhibitor of prenylation targeting cysteine containing $CX_1X_2X_3$ sequences near the C-terminus of viral proteins, i.e., is a prenylation inhibitor. The prenylation inhibitor can further comprise a peptidomimetic.

Any of these compositions in related embodiments further comprises a pharmaceutically acceptable buffer. Kits comprising a unit dosage of any or of a plurality of these compositions, optionally having instructions for use, are provided.

Another embodiment of the invention provided herein is a method for preventing and treating a viral disease in a subject caused by infection with at least one viral agent, the method involving administering a combination of nucleases, such that the nucleases are targeted to the genomic and intermediate forms of replicating viral nucleic acids. The replication of ssDNA viruses is accompanied by appearance of ssDNA, dsDNA, ssRNA (mRNA), therefore without being limited by any particular mechanism or theory, a combination of different nucleases targeted to digest specifically the appropriate forms of viral nucleic acids increases the antiviral effect of this method. Similarly, the replication of dsDNA viruses is accompanied by the appearance of dsDNA, ssDNA, ssRNA. An appropriate combination of nucleases increases the antiviral effect. Replication of ssRNA viruses is accompanied by synthesis of dsRNA and ssRNA and the combination of the appropriate nucleases results in synergistic antiviral effect. RNA RT viruses generate intermediate forms of hybrid RNA-DNA molecules, ssRNA and dsRNA. Combination of RNase H, DNase digesting ssDNA and RNases digesting ssRNA and dsRNA will increases the antiviral effects of nucleases.

Another embodiment of the invention provided herein is a method for preventing and treating a viral disease in a subject caused by infection with at least one viral agent selected from the group consisting of emerging wild-type viruses, naturally occurring mutant viruses and mutant viruses occurring in the course of an antiviral therapy, the method comprising: administering a nuclease, wherein the nuclease is selected from a group of nucleases with preferential hydrolytic activity towards the genomic form of viral nucleic acid as found in virions of the viral agent, providing that the nuclease is not wild-type bovine pancreatic DNase I or wild-type bovine pancreatic RNase A.

Another embodiment of the invention provided herein is a method for preventing and treating a viral disease in a subject caused by infection with at least one viral agent selected from the group consisting of emerging wild-type viruses, naturally occurring mutant viruses and mutant viruses occurring in the course of an antiviral therapy, the method comprising: administering a plurality of nucleases or nuclease-derived antiviral compositions, wherein at least two nucleases or nuclease-derived antiviral compositions are enzymes with preferential hydrolytic activity towards the viral genomic form of nucleic acid as found in virions of the viral agent and toward intermediate forms of nucleic acids appearing during the replication of viral genomic nucleic acids.

Another embodiment of the invention provided herein is a method for preventing and treating a viral disease in a subject caused by infection with at least one viral agent selected from the group consisting of emerging wild-type viruses, naturally occurring mutant viruses and mutant viruses occurring in the course of an antiviral therapy, the method comprising: administering at least one antiviral nuclease or nuclease-derived antiviral composition, wherein nuclease is an enzyme with preferential hydrolytic activity towards at least one replicating intermediate form of viral nucleic acid as found in the life cycle of the viral agent.

Another embodiment of the invention provided herein is a method for preventing development of viral resistance to nucleases administered for treating a viral disease, the method comprising administering a plurality of nucleases or nuclease-derived antiviral compositions, wherein at least one nuclease or nuclease-derived antiviral composition is an enzyme with preferential hydrolytic activity towards a viral genomic form of nucleic acid as found in virions of the viral agent, and at least one nuclease or nuclease-derived antiviral compositions is an enzyme with preferential hydrolytic activity towards at least one replicating intermediate form of viral nucleic acid as found in the life cycle of the viral agent.

Another embodiment of the invention provided herein is a method for treating a viral disease in a subject having an infection by a virus that has developed resistance to antiviral therapeutic agents, the agents generally being chemotherapeutic drugs of low molecular weight, rather than nucleases administered as administered by the methods herein for treatment. Drug-resistant viruses are susceptible to the antiviral activity of nucleases because they digest viral nucleic acids without regard for present or potential alterations in the sequence of nucleotides in the drug-resistant viral mutant. For this reason, development of resistance to nucleases is extremely unlikely or even hardly possible, and a drug-resistant mutant of a virus is susceptible to the antiviral activity of nucleases provided herein.

Another embodiment of the invention provided herein is a method for treating a viral disease in a subject and preventing the development of viral resistance to antiviral therapeutics other than nucleases administered for treatment, the method comprising administering the antiviral drugs in combination with at least one nuclease or nuclease-derived composition. Accordingly in a related embodiment, the antiviral therapeutic is at least one compound selected from the group of antiviral compounds consisting of viral entry inhibitors, viral assembly inhibitors, viral DNA and RNA polymerase inhibitors, viral reverse transcriptase inhibitors, viral protease inhibitors, viral integrase inhibitors, and inhibitors of viral shedding.

Another embodiment of the invention provided herein is a method for preventing and treating a non-viral disease in a subject, wherein a viral infection has been implicated as a contributing factor, the method comprising administering therapeutics directed against the non-viral disease in combination with at least one antiviral nuclease or an antiviral nuclease-derived composition.

Related embodiments for any of the above methods relate include that the diseases is caused by a plurality of viral agents. The antiviral nuclease in various embodiments is selected from the group of wild-type nucleases of human, animal, bacterial, plant and artificial origin; genetically-engineered common and uncommon mutants of wild-type nucleases of human, animal, bacterial, plant and artificial origin; and chemically and genetically modified common and uncommon mutants of wild-type nucleases of human, animal, bacterial, plant and artificial origin. Further, the viral agent in various embodiments is a dsDNA virus or an ssDNA virus of Groups I and II, respectively, and the antiviral nuclease is selected from the group consisting of Group I dsDNA-specific nucleases, Group II ssDNA-specific nucleases, Group IV ssRNA-specific nucleases, Group VI non-specific nucleases and Group VII artificial nucleases. Further, the viral agent in various embodiments is a dsRNA, an ss(+)RNA, or an ss(−)RNA virus of Groups III, IV and V, respectively, and the nuclease is selected from the group consisting of Group I dsDNA-specific nucleases, Group II ssDNA-specific nucleases, Group III dsRNA-specific nucleases, Group IV ssRNA-specific nucleases, Group VI non-specific nucleases and Group VII artificial nucleases. Further, the viral agent in various embodiments is an s/s(+)RNA Reverse Transcriptase (RT) virus of Group VI, and the nuclease is selected from the group consisting of Group I dsDNA-specific nucleases, Group II ssDNA-specific nucleases, Group IV ssRNA-specific nucleases, Group VI non-specific nucleases and Group VII artificial nucleases. Further, the viral agent in various embodiments is a dsDNA Reverse Transcriptase (RT) virus of Group VII, and the nuclease is selected from the group consisting of Group I dsDNA-specific nucleases, Group II ssDNA-specific nucleases, Group IV dsRNA-specific nucleases, Group IV ssRNA-specific nucleases, Group V hybrid-specific nucleases, Group VI non-specific nucleases and Group VII artificial nucleases. Further, the viral agent in various embodiments is a plurality of viruses selected from Group I dsDNA viruses, Group II ssDNA viruses, Group VI ss(+)RNA RT and Group VII of dsDNA RT viruses, and the nucleases are selected from the group consisting of Group I dsDNA-specific nucleases, Group II ssDNA-specific nucleases, Group IV ssRNA-specific nucleases, Group V hybrid-specific nucleases, Group VI non-specific nucleases and Group VII artificial nucleases. Further, the viral agent in various embodiments is a plurality of viruses selected from Group III dsRNA, Group IV ss(+)RNA, Group V ss(−)RNA viruses, Group VI ss(+)RNA RT and Group VII dsDNA RT viruses, and the nucleases are selected from the group consisting of Group I dsDNA-specific nucleases, Group II ssDNA-specific nucleases, Group III dsRNA-specific nucleases, Group IV ssRNA-specific nucleases, Group V hybrid-specific nucleases, Group VI non-specific nucleases and Group VII artificial nucleases.

Kits are provided for any of the above compositions, which in related embodiments in addition to the composition include a container and instructions for use. The compositions may be provided with a pharmaceutically acceptable buffer, carrier, or salt, and may be provided in a unit dose.

These and other related issues are subjects of various embodiments of the present invention. The present invention is directed in part to a novel combinatorial method for prevention and treatment of viral diseases, which takes into account multiple intermediate forms of viral nucleic acids appearing in the course of viral replication cycle, by administering selected combinations of nuclease-based antiviral compositions directed against this plurality of viral nucleic acids. The present invention is also directed to antiviral compositions derived from a variety of chemically and genetically modified nucleases targeted to different forms of viral nucleic acids and characterized by enhanced hydrolytic activity under physiological conditions, extended half-life, high-cellular uptake, low immunogenicity, resistance to intracellular inhibitors and degradation by endogenous proteases.

An embodiment of invention provides antiviral compositions derived from wide variety of nucleases of mammalian, bacterial, plant and artificial origin, including semi-synthetic and synthetic nucleases that exhibit hydrolytic activity towards a form of viral DNA and/or RNA. Antiviral nucleases provided herein comprise compositions of wild-type native and recombinant, chemically/genetically enhanced, semi-synthetic and synthetic nucleases exhibiting hydrolytic activity towards certain forms of viral nucleic acids appearing in the course of viral replication cycle.

Within the scope of this invention the antiviral nucleases are divided into seven different groups in compliance with the structure of their preferred substrates-viral nucleic acids. The viruses are divided according to the Baltimore classification into seven fundamentally different groups in accordance with the structure of viral nucleic acids and different patterns of their replication.

The seven nuclease groups herein are classified as follows: (1) nucleases with preferential hydrolytic activity towards double-stranded viral DNA (dsDNA), which belong to the DNase-I family including human DNase I and bovine DNase A, DNase α, β, γ and others, and their chemically/genetically enhanced variants; (2) nucleases with preferential hydrolytic activity towards single-stranded viral DNA (ssDNA) such as mammalian endonuclease G (endoG), extra-cellular fungal nuclease Bh1 from *Basidiobolus haptosporus*, Mung Bean nuclease and their chemically/genetically enhanced variants; (3) nucleases with preferred hydrolytic activity towards single-stranded viral RNA (ssRNA)

such as wild-type RNase A-like nucleases and their chemically/genetically enhanced variants; (4) nucleases with preferential hydrolytic activity towards double-stranded viral RNA (dsRNA) such as wild-type RNase III-like nucleases and their chemically/genetically enhanced variants; (5) nucleases with preferential hydrolytic activity towards RNA-DNA hybrids such as wild-type RNase H-like nucleases and their chemically/genetically enhanced variants; (6) nucleases with hydrolytic activity towards all forms of nucleic acids such as Benzonase® from *Serratia marcescens*, nuclease CI from *Cunninghamella echinulata* and their chemically/genetically enhanced variants, and the artificial nucleases with pre-designed preferential hydrolytic activity towards one or more forms of viral nucleic acids, which by definition, may belong to any of the above six groups of antiviral nucleases. The artificial nucleases may be further classified as biological nucleases including peptides and peptidomimetics exhibiting nucleolytic activity exemplified by nucleolytic di/tri peptides such as Ser-His, Ser-His-Asp or chemical nucleases based on catalytic activity of metal-ion complexes exemplified by tetravalent ion of cerium Ce(IV), which has been found to be among the most effective metal ions for double-stranded DNA hydrolysis.

The invention is directed in part to chemically/genetically enhanced variants of native nucleases containing non-natural amino acid residues substituting natural amino acids in selected positions. Such chemically/genetically enhanced variants of native nucleases are characterized by increased nucleolytic activity and/or resistance against endogenous proteases and/or nuclease inhibitors, wherein the enhanced variants of native nucleases are selected on the basis of their maximal hydrolytic activity at minimal cytotoxicity in physiological conditions.

In separate embodiments, the chemically/genetically modified variants with enhanced hydrolytic activity towards the particular form of viral nucleic acid are obtained by substitution of one or more neutral or negatively charged naturally occurring or "natural" amino acids located within the nuclease binding domain of its substrate or of its inhibitor, the substitution being with one or more non-naturally occurring or "non-natural" amino acids or the substituted amino acid carrying positive multiple-charged or bulky neutral side chains or keto groups. A keto group is introduced for subsequent attachment of small molecular weight multiply-charged chemical moieties or steric hindrance moieties such as a large molecular weight polymeric carrier to provide nuclease with enhanced resistance against proteolytic digestion, increased half-life and cellular uptake.

In related embodiments the invention provides antiviral compositions which are chemically/genetically enhanced nucleases within the following groups: Group I-dsDNA-specific nucleases exemplified by highly-hydrolytically active and actin-resistant uncommon mutant variants of human DNase I obtained by the following substitutions: Q11RU/E13KU$^{(2+)}$/N74KU$^{(2+)}$/A114FU$^{(keto)}$ with five additional positive charges (+5), wherein RU is non-natural homoarginine, KU$^{(2+)}$ is non-natural lysine with two positively charged side-chain amino groups and FU$^{(keto)}$ is non-natural p-acetyl-L-phenylalanine residue carrying a keto group; Group III-ssRNA-specific nucleases exemplified by ribonuclease inhibitor (RI)-resistant and non-toxic uncommon mutants of human RNase I obtained by the following substitutions: K1FU$^{(keto)}$/Q11A/N71A/E111A and human RNase S consisting of truncated S-peptide (a fragment having positions 1-15 in the amino acid sequence) obtained by the following substitutions K1FU$^{(keto)}$/Q11A and truncated S-protein (residues 21-124 amino acid residues fragment) obtained by the following substitutions N71A/G89FU$^{(keto)}$/E111A, wherein FU$^{(keto)}$ is non-natural p-acetyl-L-phenylalanine residue carrying a keto group.

In yet another embodiment the antiviral compositions disclosed in this invention comprise multivalent "shell-core" dendrimer complexes, wherein "shell" dendrimer carries multiple nonfunctional antiviral nuclease-polymer conjugates or multiple targeting ligands, wherein one or more "shell" dendrimers are associated with a "core" dendrimer through Watson-Crick bonding between the pairs of complementary oligonucleotides covalently associated with the dendrimers and chemically modified to enable a subsequent covalent bond formation between the complementary pairs.

In further embodiments, the antiviral compositions comprise native and chemically/genetically enhanced antiviral nucleases covalently associated with hetero-bi-functional polymers, wherein said hetero-bi-functional polymers are associated directly or through multivalent molecular scaffolds such as dendrimers or star polymers with multiple targeting ligands of various functions. The targeting ligands carried by polymeric carriers may comprise: a) oligomers with sequence-specific affinity to the selected sites of viral nucleic cell such as peptide nucleic acids (PNA), morpholino and pyrrolidine-amide oligonucleotide mimic (POM) oligo nucleotides, hairpin polyamides, zinc fingers, etc.; b) membrane permeating peptides (MPP) including poly-Arg/Lys peptides, Arg-rich peptides derived from HIV-TAT, Antennapedia, detoxified exotoxin A (ETA), etc. as well as nuclear localization/export signals (NLS/NES); c) cell surface receptor-recognizing ligands (T-CSR) exhibiting high-binding affinity to the cell surface receptors (CSR) of the virus primary host cells including but not limited to 8-amino acid T-peptide (ASTTNYT using the one letter amino acid code; SEQ ID NO: 1) and other short synthetic peptides derived from envelope protein gp120 of HIV-I and from other viral proteins, possessing partial amino acid sequence homology with the HIV gp120 fragment (residues 414-434), targeting primary host T-cells containing CD4 receptor; and d) cell surface receptors such as CD4 and others that can be used as ligands targeting glycoproteins such as gp120 expressed on the membranes of virus-infected cells.

In a further embodiment, the invention provides antiviral compositions comprising modified RNase S, in the form of a non-covalent nucleolytic complex formed between two conjugates of about equal molecular weight, wherein the first conjugate is the 11.5 kDa human S-protein (21-124) covalently attached to a 20 kDa targeted polymeric carrier, and the second conjugate is the 2 kDa human S-peptide (1-15) covalently attached to a 30 kDa targeted polymeric carrier, wherein each polymeric carrier is covalently associated with membrane permeating peptide Arg(R)8 and bis-PNA complementary to a conserved domain of the targeted viral nucleic acid.

In yet another embodiment the invention provides an antiviral composition comprising PEG-DNase-RNase S, in the form of a non-covalent nucleolytic complex formed between two conjugates of about equal molecular weight, wherein the first conjugate is the 11.5 kDa human S-protein (21-124) covalently attached to 31 kDa human DNase I and to a 20 kDa targeted polymeric carrier, and the second conjugate is the 2 kDa human S-peptide (1-15) covalently attached to a 60 kDa targeted polymeric carrier, wherein each polymeric carrier is covalently associated with membrane permeating peptide Arg(R)8 and bis-PNA complementary to the selected nucleotide sequence of the targeted viral DNA or RNA.

In separate embodiments, the invention provides multifunctional antiviral compositions comprising nucleases and targeting ligands covalently associated with polymeric carriers comprising multivalent dendrimers and "shell" dendrimer-"core" dendrimer complexes, wherein the terminal groups of the dendrimers are chemically modified to include sequence-specific oligonucleotides undergoing hybridization and subsequent covalent bond formation with complementary oligonucleotides associated with nucleases and targeting ligands and/or other multiarmed dendrimers. The covalent binding of two complementary base-paired oligo- or poly-deoxynucleotides can be carried out by the use of bifunctional reagents exemplified but not limited to a heterofunctional polyalkylating agent N,N,N'-tri-(β-chloroethyl)-N'-(p-formylphenyl)propylene diamine-1,3. The reagent is attached to one of oligo- or polydeoxynucleotides through a highly reactive aliphatic β-chloroethylamino group. The reactivity of the potentially active aromatic alkylating group is strongly inhibited by the neighboring formyl residue. This group might be activated, when needed, after base-pairing of oligo- and polynucleotides by its activation through reduction of the formyl residue using sodium borohydride.

The invention in other embodiments also provides methods for prevention and treatment of viral diseases in human and nonhuman animals, insects and plants, comprising an application of the virus-group-specific "cocktails" containing a mix of nuclease-derived antiviral compositions, including but not limited to the antiviral compositions of this invention, wherein each antiviral "cocktail" includes nucleases with hydrolytic activity towards certain intermediate replicating forms of viral nucleic acids appearing during the replication cycle of the targeted virus.

In one embodiment, the invention provides a method for prevention and treatment of viral diseases caused by DNA viruses including Group I of dsDNA and Group II of ssDNA viruses by application of antiviral nucleases selected from the group of nucleases comprising Group I of dsDNA-specific nucleases, Group II of ssDNA-specific nucleases, Group IV of ssRNA-specific nucleases, Group VI of non-specific nucleases and Group VII of artificial nucleases according to the "Classification of Nucleases" of the present invention.

In another embodiment the invention provides a method for prevention and treatment of viral diseases caused by RNA viruses including Group III of dsRNA viruses, Group IV of ss(+)RNA viruses and Group V of ss(−)RNA viruses by application of antiviral nucleases selected from the group of nucleases comprising Group III-dsRNA-specific nucleases, Group IV of ssRNA-specific nucleases with addition of nucleases selected from the Group I of dsDNA-specific nucleases, Group II of ssDNA-specific nucleases, Group VI of non-specific nucleases, and Group VII of artificial nucleases according to the "Classification of Nucleases" of the present invention.

In yet another embodiment the invention provides a method for prevention and treatment of viral diseases caused by Group VI of ss(+)RNA RT viruses by application of antiviral nucleases selected from the group of nucleases comprising Group I of dsDNA-specific nucleases, Group II of ssDNA-specific nucleases, Group IV of ssRNA-specific nucleases, Group V of RNA-DNA-hybrid-specific nucleases, Group VI of non-specific nucleases, and Group VII of artificial nucleases according to the "Classification of Nucleases" of the present invention.

In yet another embodiment the invention provides a method for prevention and treatment of viral diseases caused by Group VII of dsDNA RT viruses by application of antiviral nucleases selected from the group of nucleases comprising Group I of dsDNA-specific nucleases, Group II of ssDNA-specific nucleases, Group III of dsRNA-specific nucleases, Group IV of ssRNA-specific nucleases, Group V of RNA-DNA-hybrid-specific nucleases, Group VI of non-specific nucleases and Group VII of artificial nucleases according to the "Classification of Nucleases" of the present invention.

In a separate embodiment the invention also provides methods for preventing the development of viral resistance to antiviral therapeutics other than nucleases, the method comprising administering the antiviral drugs in combination with at least one nuclease or nuclease-derived composition, wherein the antiviral therapeutic administered for treatment is at least one compound selected from the group of antiviral compounds consisting of viral entry inhibitors, viral assembly inhibitors, viral DNA and RNA polymerase inhibitors, viral reverse transcriptase inhibitors, viral protease inhibitors, viral integrase inhibitors, and inhibitors of viral shedding.

The present invention provides antiviral therapeutic compositions and virus-specific methods for prevention and treatment of viral diseases. The antiviral compositions in certain embodiments are derived from antiviral nucleases covalently associated with various polymeric carriers. The antiviral nucleases comprise wild-type and chemically and/or genetically modified nucleases of mammalian, amphibian, bacterial and plant origin as well as nucleases of artificial origin with enhanced hydrolytic-activity against one or more structural forms of nucleic acids. The nucleases are chemically and genetically modified to increase bioavailability, hydrolytic-activity towards small concentrations of viral nucleic acids, and resistance against potent nuclease inhibitors. The targeted multivalent polymeric carriers-nuclease complexes exhibit antiviral action by selective targeting and ultimate hydrolytic-digestion of specific form of viral nucleic acids, which appears in the course of viral replication cycle inside infected cells, thereby blocking synthesis of viral proteins and viral replication. The targeted polymeric carriers comprise high-molecular weight molecular scaffolds including but not limited to hydrophilic polymers, star polymers, block-copolymers or dendrimers covalently associated with targeting ligands of various functions. The targeting ligands include ligands directing antiviral nuclease-polymer complexes to host cells, ligands enhancing cellular and nuclear uptake, and ligands with sequence specific binding affinity to viral nucleic acids. The multivalent antiviral nuclease-polymeric complexes can target viral nucleic acids inside infected cells for ultimate hydrolytic-digestion, while providing the nuclease with protection from endogenous proteases which are found both in blood plasma and inside the cells; and result in high cellular uptake, prolonged half-life, decreased immunogenicity and cytotoxicity.

The present invention also provides a method of use of antiviral compositions derived from wild-type and chemically/genetically enhanced nucleases as well as nucleases covalently associated with polymeric carriers for prevention and treatment of viral diseases caused by viruses divided into seven groups according the Baltimore classification. More specifically the method comprises targeting one or more viral nucleic acids appearing in the course of viral replication cycle inside virus infected cells for ultimate hydrolytic-digestion by the specially selected combination of both naked nucleases and various nuclease-polymer complexes with established high-hydrolytic-activity against one or more particular forms of viral nucleic acids, including single-stranded, double-stranded, hybrid and other forms of viral DNA and RNA appearing in the course of replication of the particular virus.

In view of the present invention comprising a multi-target approach to inhibition of replication of viruses, characteristics of different types of viruses and relevant nucleases are outlined below.

DEFINITIONS

The terms "nuclease" and "antiviral nuclease" as used herein refer to an enzyme with hydrolytic activity towards at least one specific form of a viral nucleic acid, such as DNA or RNA. The antiviral nucleases within the scope of the present invention include wild type nucleases, homologues of wild-type nucleases, chemically and genetically modified nucleases of human, animal, bacterial, and plant origin, and di/tri peptides, peptidomimetics exhibiting hydrolytic activity towards nucleic acids and other artificial nucleases. The nucleases within the scope of the present invention include dimers, trimers and higher oligomers of wild-type and modified nucleases.

The term "nuclease-derived composition" refers to any chemical composition which includes a wild type or a chemically/genetically modified nuclease or a nuclease in complex with a polymeric carrier as one of its components.

The term "subject" refers to a human, and to any animal, plant or microorganism of practical importance which can be infected by a viral agent.

The term "viral agent" refers to a virus, a provirus, a phage and to any other virus-like microorganism.

The term "specific form" of a nucleic acid refers to any linear, circular or super-coiled, single-stranded or double-stranded, DNA or RNA, which appears during the course of a viral replication cycle.

The term "nuclease targeted to a viral nucleic acid" defines one or more nucleases, which possesses greater hydrolytic activity towards a specific form of a viral nucleic acid and is covalently associated directly or indirectly through a polymeric carrier with a ligands having specific ability to bind to a nucleotide sequence of a targeted viral nucleic acid.

The term "common mutant nuclease" refers to a nuclease variant having at least one common or natural amino acid residue replaced by another common or natural amino acid residue. A "common mutant nuclease" is typically produced by random or site-directed mutagenesis and substitutes one or more of the naturally occurring amino acid building blocks.

The term "uncommon mutant nuclease" refers to a nuclease variant having at least one naturally occurring amino acid residue is replaced by an "uncommon" or non-naturally occurring amino acid residue. The identity of the 20 naturally-occurring L-amino acid residues is well established. The term "uncommon amino acid residue" includes, without limitation, any non-naturally occurring amino acid such as a β-, δ- etc. amino acid, and any D-amino acid such as D-serine, D-aspartate, N-methyl-D-aspartate and others, which may occur naturally at rare amounts in various living organisms from bacteria to mammals (Yang, et al., FEBS Letters 552 (2-3): 95-98, 2003), as well as to rarely occurring formyl-methionine (RajBhandary, *J. Bacteriol.* 176, 547, 1994) and selenocysteine (A. Bock, et al., *Mol. Microbiol.* 5, 515, 1991), which are incorporated in response to punctuation signals during translation in certain organisms.

The term "non-natural amino acid" refers to natural amino acids analogs that do not occur naturally in living organisms. The analogs are chemically modified to acquire single and multiply charged, branched and otherwise modified side chains. Common mutagenesis methods are generally limited to the common 20 amino acids although in a number of cases it has been possible to competitively incorporate close structural analogs of common amino acids throughout the proteome (Kirshenbaum et al., Chem. Bio. Chem. 3:235 (2002); Doring et al. Science 292:501, 2001). The nucleases containing non-natural amino acids can be produced by biosynthetic and semisynthetic techniques, for example, utilizing amber codon suppression method. The term includes but is not limited to natural amino acid derivatives with chemically modified side chain groups, including multiply-charged, steric hindrance, caged and other chemical modifications.

The term "keto-modified" nuclease refers to an uncommon mutant nuclease obtained by site-specific incorporation of a non-natural amino acid such as p-phenyl-alanine and m-phenyl-alanine carrying a keto group. The unique reactivity of the keto group allows it to be selectively modified by a wide variety of agents including hydrazide, hydroxylamine or semi-carbamide derivatives.

The term "thiol-modified" nuclease refers to common and uncommon mutant nucleases obtained by site-specific incorporation of either a natural or an uncommon amino acid carrying a thiol group such cysteine, selenocysteine and other non-natural cysteine-derivatives.

The term "keto-thiol-modified" nuclease refers to an uncommon mutant nuclease obtained by site-specific substitution of at least two reactive moieties: non-natural amino acid such as p-phenyl-alanine and m-phenyl-alanine carrying the keto group, and a natural or non-natural amino acid carrying the thiol group such cysteine, selenocysteine and other non-natural cysteine-derivatives.

The term "alkyl", "aryl", "substituted alkyl" and "substituted aryl" chains refer to the hydrocarbons and phospholipids, including but not limited to 1,2-dipalmitoyl-sn-glycero-3-phosphatidyl ethanolamine (DSPE), lauryl, myristoyl, palmitoyl, stearoyl, oleoyl, and lineoyl analogs of DSPE, fatty acids, etc.

The term "singly-charged" refers to a net charge of +1 or −1 at physiological pH. Singly-charged non-natural amino acids include, but are not limited to, Homoarginine, Homolysine, Diaminobutanoic acid (Dab) (Shakkottai, et al. J. Biol. Chem., Vol. 276, Issue 46, 43145-43151, Nov. 16, 2001) and others.

The term "multiply-charged" refers to a net charge greater than +1 and less than −1 at physiological pH. Multiply-charged non-natural amino acids include, but are not limited to, lysine carrying from +1 to +3 positive charges, di-aspartate carrying −2 negative charges, etc.

The term "antiviral complex containing enzyme" (ACE) refers to an enzyme that is covalently associated with at least one targeting or delivery enhancing ligand, or is covalently associated with at least one polymeric carrier, or any combination thereof including but not limited to one or more multivalent polymeric carriers carrying one or more targeted or delivery enhancing ligands.

The term "artificial nuclease" refers to a nuclease comprising a semi-synthetic or synthetic molecular scaffold containing at least one recognition domain for a substrate nucleic acid and at least one catalytic domain for hydrolysis of the phosphodiester bonds of a nucleic acid. The molecular scaffold may comprise peptide or peptide dendrimer or peptide-mimetic or polypeptide or any other biological or synthetic polymers or combinations thereof. The catalytic domains of artificial nucleases may be of biological or inorganic chemical nature. Synthetic polymers used as backbones of artificial nucleases may contain multiple organic or inorganic functional groups as catalytic elements (Suh, Acc. Chem. Res. 36: 562-570, 2003). Inorganic catalytic domains may be represented by hydrolytic metals such as lanthanide ions or their complexes covalently or non-covalently associated with the nucleic acid recognition domain of an artificial nuclease (Yamamoto et al., Nuc. Ac. Res., 31 (15): 4497-4502, 2003; Welch et al., PNAS, 100(7):3725-3730, 2003). The side chain imidazole group of histidine is exemplary for nucleolytic acid-base catalysis. At physiological pH, histidine can act as a donor or an acceptor of protons (Gray, Enzye Catalyzed Reactions, Van Nostrand Reinhold, London, pp. 264-271, 1971; Galburt, et al., Nat. Struct. Biolo, 6:1096-1099, 1999; Van der Woerd, et al., Structure 9:133-144, 2001). However some non-natural histidine derivatives may have steric factors that are the same or similar to that of histidine but have different properties relating to acidity and nucleophilicity. Known histidine derivatives include β-(1,2,3-triazol-4-yl)-DL-alanine (2), β-(1,2,4-triazol-3-yl)-DL-alanine (3), β-1,2,3,4-Tetrazol-5-yl)-DL-alanine (4), some of which are efficiently incorporated into a protein in vivo (Ikeda, et al., Protein Engineering 16: 699-706, 2003).

The term "chemically/genetically" modified or engineered nuclease refers generally to genetically modified common and uncommon mutant nucleases, and to such derivatives which are further chemically modified to enhance the hydrolytic activity, the resistance to nuclease inhibitors and proteases, and the oral bioavailability of the nuclease. The antiviral compositions herein include, those that are (isolated from nature) native or recombinant, wild-type, and also include chemically/genetically engineered, semi-synthetic and synthetic nucleases, and such nucleases having various targeting ligands covalently associated, for example, with multivalent polymeric carriers. Polymeric carriers provide the nuclease-based antiviral compositions with an extended half-life, resistance to degradation by proteases, decreased immunogenicity and toxicity, and targeting moieties provide an address to target the nuclease-based antiviral compositions to infected cells, high cellular and nucleus uptake, and direct nucleases to virus-specific nucleic acids and their replicating intermediates inside the cytoplasm or nucleus of the infected cells.

Classification of Viruses.

Viruses can be broadly classified according to the form of nucleic acid found in the virion. Recent classification emphasizes the effect of genomic content on viral replication strategies. According to the "Virus Taxonomy," viruses are divided into seven groups based upon the structure of the virion nucleic acids and different basic patterns of their replication. The viruses are grouped according to a method devised by David Baltimore referred to herein as the "Baltimore classification" ('Virus Taxonomy', H. V. van Regenmortel, et al. (Eds.), Seventh Report of the International Committee on Taxonomy of Viruses, Academic Press, 1024 pp., 2000, San Diego, N.Y.; Cann, Principles of Molecular Virology, Academic Press, 3$^{rs}$ Ed. 2001, App. 2).

DNA Viruses.

Most DNA viruses replicate in the nucleus and rely on the cellular machinery for transcription and proteosynthesis, with exception of poxviruses, which replicate in the cytoplasm using host cell enzymes for viral DNA replication. DNA viruses include dsDNA and ssDNA viruses.

Group I dsDNA viruses comprise non-enveloped viruses of Adenoviridae (Human adenovirus C) and Papovaviridae (Polyomavrius, Papillomavirus), enveloped viruses of Herpesviridae (Simplexvirus, Varicellovirus, Cytomegalovirus, Roseolavirus, Lymphocriptovirus/Epstein-Barr virus) and Poxyiridae (Variola virus causing smallpox and Vaccinia virus, infecting mammals and birds). The group includes also insect Baculoviridae, Iridoviridae, Polydnaviridae, algae Phycodnaviridae and others.

The dsDNA viruses have single-component linear or circular genomes ranging in size from 5 kilobase pairs (kbp) for Polydnaviruses through 30-38 kbp for Adenoviruses, to about 200 kbp for Baculoviruses and Herpesviruses to over 300 kbp for Poxviruses and Phycodnaviruses. Replication of the dsDNA viruses is carried out by semi-conservative replication as for cellular genomes. Among the viruses of Eukaryotes, replication occurs mainly in the nucleus, using cellular enzymes such as DNA polymerases, topoisomerases, ligases, DNA-dependent RNA polymerase's etc., and others. The replication of the dsDNA viruses depends entirely on host DNA replication machinery.

Viral dsDNA is produced in the S and G2 phases of cell division. However, the replication of Poxviruses, some Baculoviruses (granulosis group), and Iridoviruses takes place also in other cell cycle periods within virus-specified "inclusion bodies" in the cytoplasm, using viral genome encoded enzyme such as DNA polymerase. The following replication steps of these viruses are identified: primary transcription of dsDNA by host enzymes; translation of early mRNA and synthesis of regulatory proteins; replication of viral dsDNA with the help of host enzymes; late transcription controlled by viral regulatory proteins; translation of late mRNA and synthesis of late viral structural proteins; and assembly of structural proteins and viral dsDNA into mature virions.

In one embodiment this invention provides a method of inhibiting replication of dsDNA viruses by treating with one or more nucleases with preferred hydrolytic activity towards viral genomic dsDNA, ssDNA areas of replicating viral dsDNA and intermediately transcribed viral ssRNA.

Group II ssDNA viruses comprise non-enveloped Parvoviruses and Circoviruses. In addition to these mammalian viruses, the group includes Circo-like viruses infecting birds and Gemini viruses and Banana Bunchy Top-Related Viruses (BBTRV) infecting plants. The ssDNA viruses may have single linear, or single, double or multi-component circular DNA genomes, all relatively small in size: 3 kb for Circoviruses, 4-5 kb for Parvoviruses, 2.7-5.4 kb for Geminiviruses and 5-6 kb for BBTRV. The following replication steps of ssDNA viruses which occur in the nucleus are identified: formation of (−) sense DNA strand, soon after infection; formation of a "replicative form" intermediate dsDNA; primary transcription of dsDNA template by host enzymes; early translation of mRNA encoding regulatory proteins; "rolling circle" replication of viral ssDNA; late transcription controlled by viral regulatory proteins; synthesis of late viral structural proteins; and assembly of viral ssDNA and structural proteins into mature virions. Some members of parvoviridae such as adeno-associated virus (AAV) have evolved a biphasic life cycle to ensure persistence in its primate host, needing an unrelated ssDNA helper virus, adenovirus or herpes virus, for productive infection (Muzyczka et al., In *Fields Virology,* 4th Edn, pp. 2327-2359, 2001, D. M. Knipe et al., Eds., Philadelphia: Lippincott Williams & Wilkins). In the absence of a helper virus, AAV type 2 (AAV-2) establishes latency by preferential integration into a specific site on human chromosome 19

(Huser & Heilbronn J Gen Virol 84: 133-137, 2003, Kotin et al., *Proc Natl Acad Sci USA* 87: 2211-2215, 1990.

In another embodiment this invention provides a method of inhibiting replication of ssDNA viruses by treating with one or more nucleases with preferred hydrolytic activity towards viral genomic ssDNA, intermediate dsDNA and ssRNA.

RNA Viruses.

Most RNA viruses replicate in the cytoplasm with exception of Orthomyxoviruses (e.g. Influenza A, B, C), which replicate in the nucleus. The mechanism of viral gene expression is fundamentally different for RNA viruses from those of host cells containing DNA genomes. The RNA virus genome can be composed of double-stranded RNA, or dsRNA, negative-sense i.e., antisense or ss(−)RNA, and positive-sense RNA encoding viral proteins or ss(+)RNA. The RNA replication process is catalyzed by RNA-dependent RNA polymerases (RdRps), which are formed by virus encoded proteins (e.g., polymerase, helicase) and some host factors.

Group III dsRNA viruses comprise non-enveloped Reoviruses, Birnaviruses, Partitiviruses, Totiviruses and Cryptoviruses. Reoviruses infect animals, plants and insects; Birnaviruses infect vertebrates and invertebrates. Partitiviruses infect mainly fungi, which in turn may infect plants; Totiviruses infect fungi, protozoa and insects. Cryptoviruses occur in plants and are apparently transmissible via seed or pollen.

The single or multi-component viral dsRNA genomes range in size from 4-7 kbp for Partitiviruses, Birnaviruses and Totiviruses, to 20-27 kbp for Reoviruses. Reoviruses have 10-12 segments of dsRNA inside a single capsid. Early in infection, transcription of dsRNA genome by virus specific transcriptase occurs inside partially uncoated subvirus particles. The primary transcription results in synthesis of multiple ss(+)RNAs. The latter while released in the cytoplasm, serve both as late mRNA to encoding synthesis of structural proteins, and as templates for dsRNA synthesis, which occurs inside newly formed capsids.

The following replication steps of dsRNA viruses are identified: primary transcription of dsRNA forming ss(+)RNA by viral RNA-dependent RNA polymerase (RdRp) inside partially-open capsid; export of ss(+)RNA into cytoplasm; translation of ss(+)RNA in cytoplasm and accumulation of regulatory and early structural viral proteins; assembly of ss(+)RNA and viral proteins into immature virions; replication of ss(+)RNA via complementary ss(−)RNA into dsRNA by viral RdRp inside immature virions; secondary transcription of dsRNA, translation of ss(+)RNA and accumulation of late structural viral proteins; and assembly of genomic dsRNA and structural proteins into mature virions.

Group-IV ss(+)RNA viruses comprise non-enveloped viruses (Picornavrisues; Caliciviruses; Rhinoviruses, and common cold viruses), and enveloped viruses (Nidoviruses, Coronaviruses/SARS, Flaviviridae, Hepatitis C virus/HCV; Togaviridae, etc.), viruses of plants (Bromovirus, Comovirus, Potyvirus, Tobacco Mosaic Virus/TMV, etc.), viruses of insects (Nodavirus, Tetravirus) and fungi (Barnavirus). The single and multi-component genomes of ss(+)RNA viruses range in size from less than 5 kb for Bamavirus to 7-12 kb for Picornaviruses and Flaviviridae to non-segmented 27-31 kb Coronavirus, which causes Severe Acute Respiratory Syndrome (SARS) in humans.

These viral genomes act as mRNA and are translated after infection of the host cell. However, dsRNA forms of viral genomes and subgenomic RNAs were isolated from cells infected by many of ss(+)RNA viruses, including most plant viruses including TMV, some picorna-like insect viruses, and coronaviruses. The ss(+)RNA viruses replicate in cytoplasm of infected cells.

Replication steps include: translation of ss(+)RNA as mRNA with early production of RdRp; synthesis of ss(−)RNA on ss(+)RNA template by RdRp with formation of membrane associated replicative complex (RC), with ss(−)RNA being in the form of genomic-length dsRNA produced by membrane bound RNA polymerase, (e.g. Sindbis virus (SIN) the type alphavirus of togaviridae, has three intermediate replicative forms of dsRNA with one being full-length genome and the other two corresponding to the first two-thirds (the non-structural region) and the remaining one-third (the structural region) of the genome, respectively); synthesis of multiple ss(+)RNA, mRNA and ss(−)RNA; translation of ss(+)RNA and mRNA and synthesis of structural protein; and assembly of structural protein and ss(+)RNA into mature virions.

Group V ss(−)RNA viruses comprise enveloped, single (−)RNA strand viruses (Mononegavirales: Filoviridae, Paramyxoviridae, Rhabdoviridae), multiple (−)RNA strand viruses (Orthomyxoviridae, Bunyaviridae, Arenaviridae). The size of viral genomes for Mononegavirales is 11-19 kb, 10-14 kb for 6-8-component Orthomyxoviruses (e.g Influenza viruses), and 11-20 kb for 3-component Bunyaviruses. Although the ss(−)RNA viruses directly infect only higher Eukarya (antropods and vertebrates), they may also infect plants as a result of close association of some insects and host plants. The ss(−)RNA viruses replicate in the host cell cytoplasm with exception of Orthomyxoviruses which replicate in the nucleus of the host cells.

The following replication steps are identified: primary transcription of ss(−)RNA by viral RdRp with production of mainly mRNA, ss(+)RNA and formation of replicative complex (RC) with ss(+)RNA being partially in dsRNA form within RC; production of full length ss(+)RNA and progeny ss(−)RNA; secondary transcription from progeny ss(−)RNA; translation and accumulation of structural proteins; nucleocapsid assembly and maturation; and budding of nucleocapsid through host membrane containing viral envelope proteins.

According the above-described steps of replication, no intermediate viral DNA is synthesized during replication of RNA viruses. However, some experimental evidence exists both in vivo and in vitro of complementary viral ssDNA production, possibly involving endogenous reverse transcriptase (RT) in cells infected by RNA viruses such as lymphocytic choriomeningitis virus (LCMV) (Klenerman, et al., Letters to Nature, 390: 298-301, 1997, polio, and measles viruses (Zhdanov, Nature 256: 471-473, 1975). It has been suggested that endogenous RT may reverse-transcribe RNA derived from other infectious viruses (Zhdanov, Nature 256: 471-473, 1975). The source of the endogenous RT could be endogenous retroviruses or a variety of other interspersed elements (Wiener et al., A. Rev. Biochem. 55, 631-661, 1986), wherein reverse transcripts from such endogenous sources may account for 10-20% of the mammalian genome (Coffin, in Reverse Transcriptase, pp. 445-479, 1993, Eds. Skalka and Gough, Cold Spring Harbor Lab Press, NY). Low levels of RT activity due to the presence of endogenous avian leukosis viruses (ALV-E) and endogenous avian viruses (EAV) was also detected in chicken embryonic fibroblast substrates used in production of measles, mumps and yellow fever vaccines (Hussain et al., Journal of Virology, January 77(2): 1105-1111, 2003; Johnson and Heneine, J. Virol. 75(8): 3605-3612, 200.1).

Antiviral effects of RNase I against RNA viruses is enhanced herein by combining RNase I with DNase I. Surprisingly, a strong synergistic inhibitory effect is produced by combining DNase I and RNase I on the replication of equine encephalitis virus (see example 40). The occurrence of intermediate viral DNA during the replication of other RNA viruses is envisioned as equivalent to this observation. The phrase "intermediate viral DNA" as used herein shall mean viral-specific DNA that is synthesized during the replication cycle of any virus including a DNA or an RNA virus. While intermediate viral DNA is generally thought by one of ordinary skill in the art of virology to be the product of RT activity in an RNA virus life cycle, the phrase "intermediate viral DNA" as used herein is not limited by any specific mechanism of synthesis, rather refers to any or all species of viral DNA found in replication of a virus, regardless of mode of production.

Because of the possibility for the occurrence of intermediate viral DNA due to endogenous RT activity or other unknown factors in cells infected by other RNA viruses, an embodiment of the compositions herein is a combination of the nucleases having nucleolytic activity for Group I dsDNA and for Group II ssDNA viruses, which is a resulting antiviral "cocktail" against all RNA viruses. Thus in a separate embodiment the invention relates to a method of inhibiting replication of dsRNA, ss(+)RNA and ss(−)RNA viruses by one or more nucleases with preferred hydrolytic activity towards viral dsRNA, ssRNA and intermediate viral ssDNA and dsDNA.

DNA and RNA Reverse Transcribed (RT) Viruses.

Group VI ss(+)RNA RT viruses comprise enveloped Retroviridae family members, which include Lentiviruses such as human immunodeficiency virus (HIV) infecting humans, simian immunodeficiency virus (SIV) infecting monkeys, Visna-maedi virus (VISNA) infecting sheeps, and equine infectious anemia virus (EIAV) infecting horses; Alpharetroviruses, which include avian leucosis virus (ALV) and Roues sarcoma virus (RSV); Gamma retroviruses, which include feline leukemia virus (FLU) and Maloney marine leukemia virus (MOVE); Betaretroviruses, which include mammalian mouse mammary tumor virus, MMTV) and Mason-Pfizer monkey virus (MPMV), Deltaretroviruses represented by human T-lymphotropic virus (HTLV), Spumavirus (human spumaretrovirus), and others.

Retrovirus virions fuse with a targeted cell membrane, releasing viral genomes each containing two ss(+)RNA molecules into the cytoplasm. Reverse transcriptase (RT) is associated with the retroviral viral genome, and viral RNAs serve as templates for reverse transcription. All retroviruses encode four genes called gag, pro, pol and env. The sizes of the retroviral ss(+)RNA genomes range from 7,000-11,000 b; the size of HIV genome is 9,749 b.

The following replication steps are identified: reverse transcription of virion ss(+)RNA in cytoplasm by virion-associated RT to produce a resulting intermediate RNA-DNA hybrid complex; digestion of RNA within the RNA-DNA complex by RNase H; replication of the remaining dsDNA by RT into linear and circular dsDNA forms with long terminal repeats (LTR); import of dsDNA into the nucleus; integration of linear proviral DNA into host cell DNA by integrase; replication and transcription of integrated dsDNA by host enzymes with production of progeny ss(+) RNA; translation and accumulation of late structural protein; assembly of proteins with progeny ss(+)RNA into viral nucleoprotein; budding through cell membrane; and incorporation of viral envelope glycoproteins into the virion during budding.

In yet another embodiment, this invention provides a method of inhibiting replication of ss(+)RNA RT viruses by one or more nucleases with preferred hydrolytic activity towards viral genomic ssRNA, and intermediate hybrid RNA-DNA, ssDNA, dsDNA and ssRNA.

Group VII dsDNA RT viruses comprise enveloped Hepadnaviridae family, which includes hepatitis B virus (HBV), and as described herein, Group VII also includes unique non-enveloped Hepatitis Delta Virus (HDV), replication and spread of which require presence of HBV. HDV has a genome of 1,678 bases consisting of a covalently closed circular ss(−)RNA molecule that folds in a rigid dsRNA rod-like structure by extensive intramolecular base pairing. Using a mechanism known in many plant viruses as the double rolling circle model, both RNAs are transcribed from a single initiation. Similar to other ss(−)RNA viruses, HDV produces intermediate dsRNA in the course of replication.

The following viral replication steps are identified for dsDNA RT viruses: entrance of viral nucleocapsid into the cytoplasm to reach the cell nucleus, and synthesis of circular dsDNA and repair of gaps in (+) DNA strand to yield a covalently closed circular (CCC) super-coiled DNA; transcription of the CCC template to obtain four viral ss(+) RNAs, which are then transported to the cytoplasm; reverse transcription inside the new viral nucleocapsid; production of replicative intermediates in CCC-DNA, relaxed circular RC-DNA, linear ssDNA and dsDNA in addition to ss(+) RNA; transcription of DNA to synthesize mRNA(s) and ss(+)RNA by host DNA-dependent RNA polymerase; translation of mRNA and ss(+)RNA in cytoplasm; accumulation of viral RNA and proteins; interaction of viral proteins with ss(+)RNA and assembly of provisions; reverse transcription of ss(+)RNA inside virions by viral RT to RNA/DNA complex with intermediate ssDNA; removal of RNA from DNA-RNA hybrid by RNase H; conversion by virion RT of RNA/DNA complex to circular, gapped dsDNA with intermediary ssDNA; and maturation of virions.

In yet another embodiment this invention provides a method of inhibiting replication of dsDNA RT viruses by one or more nucleases having hydrolytic activity towards viral genomic dsDNA, and/or intermediate viral hybrid RNA-DNA, circular ssDNA, linear ssDNA, dsDNA and ssRNA. To inhibit HDV associated with its "helper" HBV, additional nucleases having hydrolytic activity towards viral dsRNA are required.

In summary, viruses comprise seven groups according to form of their DNA or RNA genomes, and compositions and methods for treatment of virus diseases caused by each group require different strategies that depend on the nature of intermediary forms of DNA and RNA that are different and possibly multiple.

TABLE 1

Examples of DNA and RNA viruses

| Group | Nucleic Acid | Examples of Viruses | Envelope | Genome Size (kb) |
|---|---|---|---|---|
| I | dsDNA | Small Pox | Yes | 130-375 |
| | | Herpes | Yes | 120-225 |
| | | Adeno | No | 30-38 |
| | | Papilloma | No | 8.0 |
| | | Polyoma | No | 5.3 |
| II | ssDNA | Parvo, Circo | No | 5.0 |
| III | dsRNA | Reo | No | 18-31* |
| | | Birna | No | 5.8-6.0 |

TABLE 1-continued

Examples of DNA and RNA viruses

| Group | Nucleic Acid | Examples of Viruses | Envelope | Genome Size (kb) |
|---|---|---|---|---|
| IV | ss(+)RNA | Corona/SARS | Yes | 27-31 |
| | | Hepatitis C | Yes | 10.5 |
| | | Hepatitis A | Yes | 7.5 |
| | | Toga | No | 9.7-11.8 |
| | | Foot & Mouth | No | 8.5 |
| | | Polio | No | 7.4 |
| | | TMV | No | 6.4 |
| V | ss(−) RNA | Influenza | Yes | 12-15* |
| | | Measles | Yes | 17-20 |
| VI | ssRNA RT | HIV | Yes | 9.75 |
| VII | dsDNA RT | HBV | Yes | 3.1 |

*Segmented genomes, total size shown.

Various embodiments of the present invention envision a multi-target approach to inhibition of replication of viruses, based on characteristics of nucleases that are targeted to different intermediate forms of replicating viral nucleic acids. Classification of relevant antiviral nucleases and descriptions of their characteristic properties are outlined below.

Classification of Nucleases.

Nucleases can be broadly classified based on specificity of their hydrolytic attack toward the phosphodiester bonds between sugar moieties, riboses or deoxyriboses within two different nucleic acids: DNA and RNA. Accordingly, these enzymes were initially classified as DNases and RNases (Kunitz, J. Gen. Physiol 24: 15, 1940). Even though some bacterial endonucleases and venom phosphodiesterases hydrolyze both RNA and DNA (Schmidt, in Chargaff and Davidson (eds.), The Nucleic Acids, Vol. 1, Academic Press, 1955), the classification of nucleases into DNase and RNase suggested by Kunitz was considered sufficient at that time. As nucleases may differ significantly in their hydrolytic-activity towards various forms of DNA and RNA, new classification schemes were suggested, which take into consideration the structural specificity of substrates such as double- or single-strandedness of DNA and RNA, existence of hybrid DNA-RNA forms and A-, B- and Z-conformations of DNA, and cleavage specificity such as DNA cleavage by DNase I in minor grove domain, etc. (Mishra, Nucleases: Molecular Biology and Applications, John Willey & Sons, Hoboken, N.J., 2002, Ch. 1).

Classification herein of nucleases as antiviral agents as used herein for therapeutic purposes is based on characteristics of the nucleases such as biological source, and structure and specificity of nucleic acid substrates, i.e., viral genomes and nucleic acid intermediates that appear during a viral replication cycle. The nucleases are further subdivided into endonucleases and exonucleases according to the mode of action. The endonucleases split DNA or RNA at internal sites, while exonucleases progressively split off single nucleotides from 3' or 5' ends of DNA or RNA. Also relevant to classification is that viral dsDNA appears in its unprotected form inside the cell in the course of a viral replication cycle in a right-handed and extended B-DNA form, except when forming DNA-RNA hybrids, which are A-type helices. B-DNA must usually transform into A-DNA type prior to hybrid formation. A-type helices are also right-handed but are shorter and wider that B-type helices. The third form, Z-DNA is a left-handed helix longer than B-DNA helix and with reverse twist (Calladine and Drew, Understanding DNA, Academic, London, 1997). Most natural and artificial nucleases have preferred nucleolytic activity towards B-dsDNA, except RNase H, which specifically targets RNA in RNA-DNA type A helixes.

The antiviral nucleases described herein comprise wild-type native and recombinant natural nucleases, i.e., chemically/genetically modified natural nucleases to enhance their binding affinity and hydrolytic activity towards their particular targeted substrate, to increase nuclease resistance to inhibitors and endogenous proteases. The antiviral nucleases provided herein also comprise artificial nucleases, including semi-synthetic biological and chemical nucleases specially designed to possess hydrolytic activity towards specific forms of viral nucleic acids. The antiviral nucleases are classified into seven groups according to the nature and the form of their preferred substrates, which constitute various forms of viral nucleic acids appearing in the course of a viral replication cycle.

Group I dsDNA-specific nucleases are enzymes with preferential hydrolytic activity towards double-stranded DNA. This group includes wild-type native and recombinant, chemically/genetically modified DNase-like nucleases of mammalian, bacterial or plant origin which digest linear, nicked-circular or super-coiled double-stranded DNA. Nucleases in this group include the DNase I family, DNase α, DNase β, DNase γ, DNase II family, DNase II-like Acid DNase (DLAD), Exonuclease III, and the like, as well as artificial nucleases that harbor a sequence-specific recognition domain for a double-stranded viral DNA. The main properties of two Group I representative nucleases, human DNase I and DNase II, are described below.

Human pancreatic DNase I has optimal activity at slightly alkaline conditions, such as pH about 6-9.5. Optimal activity of DNase I requires presence of divalent captions such as $Mg^{2+}$, $Mn^{2+}$ and $Ca^{2+}$, and activity is significantly decreased under physiological concentrations of sodium, potassium and phosphate salts. For example human DNase I retains about 50% of its activity at 50 mM NaCl, and less than 10% of its maximum activity at physiological concentrations (about 150-200 mM NaCl).

Another factor contributing to limited hydrolytic potency of native wild-type DNase I in vivo is the presence of DNA binding proteins in human serum. Endogenous human DNase I present in serum in typical concentrations of (about 3.2+/−1.4 ng/ml) has a very low or undetectable level of nucleolytic activity on endogenous serum DNA, primarily due to the presence of actin, a potent inhibitor of DNase I. Pharmacodynamics studies showed that a minimum wild-type recombinant human DNase I serum concentration as high as 50-100 ng/ml is required to achieve detectable catalytic activity against 25-250 ng/ml endogenous DNA in human serum (Prince, et al., Clin. Exp. Immunol. 113(2): 289-96, 1998). Total actin levels including monomeric G-actin and polymerized F-actin were reported at 125 µg/ml in normal human serum (Pan, et al., J. Biol. Chem., 273:18374-18381, 1998), and somewhat lower levels (30-50 µg/ml) were reported for human plasma (Mejean, et al., J. Immunol. Methods 99:129-135, 1987). G-actin, a 42 kDa structural protein, and 31 kDa DNase I form a complex with a $K_i$ $10^{-9}$ M (Lazarides, et al., Proc. Natl. Acad. Sci. USA 71: 4742-4746, 1994; Ulmer, et al. Proc. Natl. Acad. Sci. U.S.A. 93: 9225-8229, 1996).

Variants of recombinant human rh-DNase I are disclosed in US patent applications (2001/0041360 of Nov. 15, 2001 to Lazarus et al., and 2002/0173025 of Nov. 21, 2002 to Lazarus and Pan) which have increased activity that is less susceptible to inhibition by actin and at physiological concentrations of salts. These variants have mutations at or near amino acid residues involved in binding of substrate DNA and G-actin. Although G-actin is a potent inhibitor of human, bovine, mouse and rabbit DNase I, amphibian DNase I is unaffected by G-actin. Residues Y65, V67 and A114, which are responsible for actin-binding in human and bovine DNase I, are not conserved in amphibian DNase I (Paudel and Liao, J. Biol. Chem. 261: 16012-16017, 1986; Yasuda T. et al. J. Biochem. (Tokyo) 108: 393-398, 1990).

Human pancreatic DNase I is a 282-amino acid glycoprotein with two Asn-linked glycosylation sites at positions N18 and N106. The enzyme consists of 22 signal amino acids (MW 2197.7 Da) and 260 chain amino acids (MW 29253.9 Da), including a positive arginine residue and a positive lysine residue in signal, 13 positive arginine residues in the chain (R31, R41, R73, R79, R85, R111, R117, R121, R126, R177, R185, R213, R222), 6 positive lysine residues in the chain (K2, K15, K50, K77, K157, K260), 12 negative glutamate residues (E) in the chain and 22 negative aspartate (D) residues in chain, which results in a total negative charge (2+13+6−12−22) of −13 for 282 amino acid (MW 31,451.6 Da) native human pancreatic DNase I (ref. SWISS PROT P24855).

Human pancreatic DNase I also contains mannose-6-phopshate (M-6-P) residues assigned to two sites of glycolsylation-two asparagine residues Asn-106 and Asn-18, and the nuclease exhibits very strong binding affinity to cation-independent mannose-6-phosphate receptor (CI-MPR) (Cacia et al., Biochemistry 37:15154-15161, 1998).

Recently exogenous human pancreatic DNase I have been shown to enter living human cells through engagement of CI-MPR present on cytoplasmic membrane (Oliveri, et al., Eur. J. Immun. 34:273-279, 2004). In contrast bovine pancreatic DNase I is glycosylated at a single site Asn-18 (Liao, et al., J. Biol. Chem. 248: 1489-1493, 1973). The bovine DNase I contains high-mannose and hybrid oligosaccharides with the latter containing sialic acid (Salnikow, et al., J. Biol. Chem. 245:5685-5690, 1970), but no M-6-P residues are present on the bovine DNase I (Cacia et al., Biochemistry 37:15154-15161, 1998).

In one embodiment this invention describes polymeric complex containing nuclease such as DNase I, RNase I and others wherein the polymer is modified to contain multiple mannose-6-phopshate (M-6-P) residues targeting CI-MPR cell surface receptors (see Example 3).

Human DNase II is a 344 amino acid (MW38 kDa) endonuclease that functions optimally within about pH 4.5-5.0 without an apparent requirement for divalent captions. Human DNase II cuts DNA similarly to DNase I, producing single-strand nicks rather than double-strand cuts (Baker et al., Gene 215:281-289 (1998). Although DNase II may enhance or induce cell apoptosis, possibly by direct damage of cellular DNA, recent data demonstrated that over-expression of DNase II is not sufficient to induce cell death in vivo (Evans et al., Gene 295:61-70, 2002). DNase II enzymes are involved in engulfment-mediated clearance of DNA (Evans et al., Gene 295:61-70, 2002, Mvllroy et al., Genes Dev. 14:549-558, 2000). DNase II has a leader peptide, which promotes enzyme insertion into the endoplasmic reticulum (Lyon et al., Gene 252:147-154, 2000; Shiokawa and Tanuma, Biochem. Biophys. Res. Commun. 247:864-869, 1998; Baker, et al., Gene 215:281-289, 1998).

Unlike DNase I that has tissue specific expression patterns, DNase II has a ubiquitous tissue distribution (Krieser et al., Gene 269: 205-216 (2001), consistent with its proposed roles in DNA degradation subsequent to phagocytosis and DNA cannibalism. The DNase II family includes acidic nucleases such as mammalian DNase II-like acid DNase (DLAD), a 40.7 kDa basic cytoplasmic protein sharing 37% amino acid identity with DNase II, which is expressed in mammalian liver (Shiokawa and Tanuma, Nucl. Acid Res. 27(20):4083-4089, 1999). High nucleolytic activity of DNase II at acidic conditions is a feature of DNase II-derived antiviral compositions provided herein. Simultaneous endosomal Engulfment of virus and exogenous DNase II as provided herein promotes hydrolytic digestion of viral DNA by the nuclease within acidic secondary lysosomes.

Group II ssDNA-specific nucleases comprise enzymes with preferred hydrolytic activity towards single-stranded DNA including wild-type native and recombinant, chemically/genetically modified Bh1 nuclease from *Basidiobolus haptosporus*, Mung Bean nuclease, and the like, as well as artificial nucleases, which harbor a special sequence-specific recognition domain for a single-stranded viral DNA. The properties of two Group II representatives: human endonuclease G and fungal Bh1 nuclease are described.

The human Endonuclease G (endoG), a sugar-nonspecific 29 kDa enzyme displays strong hydrolytic activity towards ssDNA and ssRNA. The enzyme is responsible for major nuclease activity in mitochondria, and it is released from intermembrane spaces of mitochondria during apoptosis in a caspase independent fashion (Parrish, et al. Nature 412: 90-94, 2001; Liu, et al., Nature 412:95-99, 2001). EndoG has greater hydrolytic activity on single-stranded nucleic acid substrates ssDNA and ssRNA than on dsDNA (Cote and Ruiz-Carrillo, Science 261:765-769, 1993; Ikeda, et al., Biochem Biophys. Res Comm. 235:291-294, 1997). EndoG requires either $Mg^{2+}$ or $Mn^{2+}$ and not $Ca^{2+}$ as its divalent caption (Ruiz-Carrillo and Renaud, EMBO J. 6:401-407, 1987; Gershenson, et al. Nucleic Acid Res 23:88-97, 1995). EndoG has biphasic pH optima for attacking dsDNA (at pH 9.0 and pH 7.0), and is inhibited about 15-fold at physiological monovalent caption strength.

First-hit kinetics indicates that supercoiled plasmids are relaxed by a single-stranded nick produced by the action of endoG (Widlak, et al. J. Biol. Chem. 276(51):48404-48409, 2001). The endoG provides an important nicking function for mitochondrial DNA (mtDNA) in vivo, while mitochondrial factors such as specific membrane phospholipids, polyamines and single-stranded DNA-binding protein (SSB) have been shown to modulate the enzyme's activity and prevent cleavage at single-stranded moieties of mtDNA. Phosphatidylcholine and phosphatidylethanolamine, major constituents of the mitochondrial inner membrane, have been shown to stimulate purified Endo G activity in vitro by 5- to 10-fold. Spermine also stimulates the enzyme activity for about 4-fold at lower concentrations of 5-100 μM, and largely inhibits the degradation of ssDNA and dsDNA at concentrations over 500 μM (Ikeda, et al. J. Biochem. Mol. Biol. Biophys. 6(1):17-21, 2002).

Another representative of this group is Bh1 nuclease, an extracellular nuclease isolated from *Basidiobolus haptosporus (Basidiobolus ranarum)*, a fungus which belongs to the order Entomophthorales of the Zygomycetes. This saprophytic fungus has a world-wide distribution and can be found in intestinal contents of reptiles, amphibians, and some mammals. Single-strand-specific nucleases with high-selectivity towards single-stranded nucleic acids and single-stranded regions in double-stranded nucleic acids are widely distributed in microorganisms, plants and animals. However, only a few other single-strand-specific enzymes including Mung Bean nuclease, S1 nuclease from *Aspergillus oryzae*, P1 nuclease from *Penicillium citrinum*, Bal 31 nuclease from *Alteromonas espejiana, Neurospora crassa, Ustilago maydis* have been sufficiently characterized (Shishido et al., Single-strand-specific nucleases. In Nucleases, Linn, S. M., Lloyd, R. S. & Roberts, R. J., Eds), 2nd Ed, pp. 155-185, 1985). Cold Spring Harbor Laboratory Press, Cold Spring Harbor, N.Y.).

Most single-strand-specific nucleases have an acid optimum pH and require metal ions to be active, which makes it problematic for use in physiological conditions. The Bh1 nuclease is a 30 kDa metalloprotein which has no obligate requirement for metal ions to be active, and it has highly preferred hydrolytic activity towards single-stranded DNA versus single-stranded RNA, although as some other single-stranded-specific the enzyme at high concentrations may slowly digest double-stranded DNA. Influence of salt concentration on the ssDNase activity of nuclease Bh1 showed that the activity reaches its maximum around 25-50 mM of NaCl or KCl. However, at physiological level of salt concentrations 150-200 mM of NaCl the enzyme exhibited approximately 35% of its maximum activity (Desai and Shankar, Eur. J. Biochem. 267, 5123-5135, 2000).

Group III dsRNA-specific nucleases comprise enzymes with preferred hydrolytic activity towards double-stranded RNA. This group includes wild-type native and recombinant, chemically/genetically modified RNase III-like nucleases, as well as artificial nucleases, which harbor a special sequence-specific recognition domain for a double-stranded viral RNA. Properties Group representative nucleases mammalian RNase III and human RNase I are described.

Mammalian RNase III nucleases belong to a super-family of double-stranded RNA-specific endoribonucleases that participate in diverse maturation and decay pathways in both eukaryotic and prokaryotic cells (Aravind et al., Methods Enzymol 341: 3-28, 2001). The RNase III super-family also includes human Dicer, a multi-domain 218 kDa endonuclease responsible for processing double-stranded RNA to small interfering RNAs (siRNAs), silencing certain genes during a process of RNA interference (RNAi). It also catalyzes excision of regulatory microRNA from precursors (Provost, et al., EMBO J. 21(21): 5864-5874, 2002; Zhang, et al., EMBO J. 21(21): 5875-5885, 2002). RNase III proteins contain a signature sequence (HNERLEFLGDS; SEQ ID NO:2) and range in size between 25-55 kDa. In some species like Drosophila and Caenorhabditis elegans, the enzyme contains 2 copies of the sequence (Filippov, et al., Gene (Amst.) 245, 213-221, 2000), which may suggest that some-RNase III proteins can form an active catalytic center as a monomer. Deletion and mutation of the signature sequence abolishes or reduces catalytic activity of the enzyme (Nicholson, Prog. Nucleic Acids Res. Mol. Biol. 52, 1-65, 1996). In Escherichia coli RNase III forms a 52 kDa homodimer (Dunn, J. Biol. Chem. 251, 3807-3814, 1976), and requires a divalent metal ion, preferably $Mg^{2+}$ (Dunn and Boye, Eds., Ribonuclease III, The Enzymes (New York, Academic Press):485-499, 1982).

A cDNA encoding human RNase III (US patent application 2003/0044941 to Crooke) encodes a 160 kDa (1374 amino acid) protein containing multiple domains involved in pre-ribosomal RNA processing (Wu, et al., J Biol Chem 275:36957-36965 (2000). The human RNase III domain (425 amino acids: residues 949-1374) is located at the carboxy terminus of the protein and is homologues to C. elegans, yeast and bacterial RNase III. Human RNase III contains proline rich (1-220 amino acids) and serine-arginine-rich (amino acids 221-470) domains near the amino terminus.

RNase III cleavage of double-stranded RNA regions artificially formed with the help of exogenous "RNA-like" oligonucleotides has been described (Wu et al., J. Biol. Chem. 273:2532-2542, 1998; U.S. Pat. Nos. 5,898,031 and 6,107,094 to Crooke). Multiple homologs of human RNase III polynucleotides have been disclosed along with the homologs of polypeptides encoded by the human RNase III DNA (US patent application 2003/0044941 to Crooke).

Group IV ssRNA-specific nucleases comprise enzymes with preferred hydrolytic activity towards single-stranded RNA. This group includes wild-type native and recombinant, chemically/genetically modified RNase A-like nucleases, as well as artificial, which harbor a special sequence-specific recognition domain for viral single-stranded RNAs. Relevant properties of Group IV representative bovine pancreatic RNase A and human pancreatic RNase I are described herein.

Bovine pancreatic RNase A consists of 26 signal amino acids (MW=2788.6) and 124 chain amino acids (MW=13,690.2 Da), including one positive arginine residue and one positive lysine residue in signal, 4 positive arginine residues in chain (R10, R33, R39, R85), 10 positive lysine residues in chain (K1, K7, K31, K37, K41, K61, K66, K91, K98, K104) and 5 negative glutamate residues in chain (E) and 5 negative aspartate residues in chain (D) which results in (2+4+10−5−5) a gain of +6 positive charge for 150 amino acid (MW 16,478.8 Da) native bovine pancreatic RNase A (ref. SWISS PROT P00656). RNase A hydrolyzes single-stranded RNA phosphodiester bonds, particularly those linked to pyrimidine bases such as uracil via a two-step reaction which involves two histidine residues H12 and H119. The side chains of the following residues form the active domain of the enzyme: His12, Lys41, Val43, Asn44, Thr45, His19, Phe120, Asp121, Ser123 (Raines, Chem. Rev. 98:1045-1065, 1998).

A potent inhibitor of RNase A, called "ribonuclease inhibitor" (RI) is a 50 kDa protein that constitutes of about 0.01% of the protein in the cytosol of mammalian cells (Blackburn and Moore, Enzymes XV: 317-433, 1982). A group of 24 amino acid residues are involved in contact of RNase A with RI. RNase A is cleaved by subtilisin or protease K between Ala20 and Ser21 residues, producing enzymatically active RNase S comprising a tightly bound non-covalent complex of S-peptide (residues 1-20) and S-protein (residues 21-124) that possesses full activity of RNase A (Richards and Vithayathil, J. Biol. Chem. 234: 1459-1465, 1959). N-terminal residues 1-15 of bovine S-peptide Lys(K)-Glu(E)-Thr(T)-Ala(A)$_3$-Lys(K)-Phe(F)-Glu(E)-Arg(R)-Gln(Q)-His(H)-Met(M)-Asp(D)-Ser(S) (SEQ. ID NO:3) are sufficient to reconstitute fully active RNase S with very high affinities $K_d<10^{-9}$ (Kim and Raines, Protein Sci. 2:348-356, 1993).

Another representative of this group is human pancreatic RNase I, which is considered to be a homolog of bovine pancreatic RNase A (Seno, et al. Biochem. Biophys. Acta 1218:466-468, 1994; Beintema, et al. Anal. Biochem. 136: 48-64, 1984). Human RNase I shares about 70% homology with bovine RNase A and possesses similar key structural and catalytic residues (Weickmann, et al., Biochemistry 20:1272-1278 (1981). Human RNase I has six basic amino acids at positions where RNase A has instead neutral residues, in particular Arg(R)4 and Lys(K)102 are located near the binding sites for RNA. Furthermore negative aspartate Asp(D)38 in RNase A is replaced by neutral glycine Gly (G)38 in human RNase I, near Arg(K)39 common for both enzymes (Libonatti and Sorrentino, Methods Enzymol. 341: 234-248, 2001).

RNase I hydrolytic activity is differentially influenced by ionic strength and divalent ions, and compared to RNase A it has a four amino acid carboxyl-terminal extension, Sorrentino and Libonatti, Arch. Biochem. Biophys. 312:340-

348, 1992; Sorrentino, et al., J. Biol. Chem. 267:14859-14865, 1992). Under physiological salt conditions RNase I is about 500 times more enzymatically active with double-stranded RNA substrate than RNase A. It has been postulated that strong local positive electrostatic potential could destabilize the double strand (Sorrentino and Libonatti, FEBBS Lett, 404, 1-5, 1997). Fully enzymatically active human RNase S can be reconstituted combining synthetic or cloned human S-peptide (residues 1-15 (SEQ ID NO: 60): Lys(K)-Glu(E)-Ser(S)-Arg(R)-Ala(A)-Lys(K)$_2$-Phe(F)-QRQ-His(H)-Met(M)-Asp(D)-Ser(S) and cloned truncated human S-protein (21-124). The gene fragment coding for human S-peptide and human S-protein was obtained from human placental cDNA (Dubel, Tumor Targeting 4:37-46, 1999).

Antiviral compositions derived from non-immunogenic human RNase I and human RNase S are provided herein for treatment and prevention of viral diseases caused by RNA viruses. For example, potential host cells can be preventively loaded with a fairly high concentration of human S-peptide that is conjugated with a high molecular weight hydrophilic polymer such as PEG, and is targeted to receptors of the virus host cells by a special ligand e.g. folate in the case of Ebola virus, and carrying a membrane penetrating peptide such as Poly(Arg) peptide, HIV-TAT$_{43-49}$, etc. Such S-peptide-PEG conjugates are characterized by prolonged half-life, strong proteolytic resistance and high cellular uptake. Without being bound by any particular theory or mechanism, even high cellular uptake of non-immunogenic and hydrolytically inactive S-peptide-PEG conjugate should not provoke significant side effects in uninfected cells. A next step is administering the human S-protein-PEG conjugate of the same molecular weight and half-life as S-peptide-PEG conjugate, and targeted by the same folate ligand and poly(Arg) peptide. The double-targeting technique can decrease reconstitution of fully active RNase S inside non-targeted cells, and therefore decrease side effects.

This group further includes common and uncommon mutants of each of human RNase I, bovine RNase A and their RNases S, such mutants exhibiting lower binding affinity to RI while maintaining high enzymatic activity and low cytotoxicity comparable to those of the native RNase I, RNase A and RNase S. The mutants include substitutions in which at least one wild-type or natural amino acid, located in, for example, the conserved nuclease RI-binding domain, is replaced by a non-natural amino acid, for example, an amino acid carrying a bulky neutral or a charged side chain or a keto group.

The RI-binding domain, conserved in human RNase I and bovine RNase A, includes three amino acids, Lys(K)1, Lys(K)7 and Gln(Q)11 localized within truncated S-peptide region (Lys(K)1-Ser(S)15), two amino acids that are localized in S-protein region Asn(N)71 and Asp(E)111, and ten amino acids that are within the second loop region of S-protein between two di-sulfide bonds Arg(R)$_{85}$-Asn(N)$_{94}$. Group IV ssRNA-specific uncommon mutants are exemplified by ribonuclease inhibitor (RI)-resistant and non-toxic uncommon mutants of human RNase I obtained by genetic engineering to produce the following substitutions: K1FU$^{(keto)}$/Q11A/N71A/E111A; and human RNase S consisting of truncated S-peptide (1-15 amino acid residues fragment) obtained by the following substitutions K1FU$^{(keto)}$/Q11A; and truncated S-protein (residues 21-124 amino acid residues fragment) obtained by the following substitutions N71A/G89FU$^{(keto)}$/E111A, wherein FU$^{(keto)}$ is non-natural p-acetyl-L-phenylalanine residue carrying a keto group.

Group V hybrid-specific nucleases comprise enzymes with preferential enzymatic activity for RNA-DNA hybrids as a substrate. The family includes wild-type, native, and recombinant, chemically/genetically modified RNase H family of nucleases, as well as artificial nucleases, each member having a sequence-specific recognition domain for single-stranded RNA in a viral RNA-DNA hybrid.

The Group V antiviral nucleases are represented by two classes of mammalian RNase H, type 1 and type 2 that hydrolyze the RNA strand in RNA-DNA heteroduplexes. RNase H enzymes have been identified in all organisms (Stein & Hausen, Science 166, 393-395, 1969; and Cathala et al. J. Biol. Chem. 254, 7353-7361, 1979; Frank, et al., J. Biol. Chem. 379, 1407-1412, 1998; Frank, et al. FEBS Letters, 450, 251-256, 1999; and Ohtani et al., Biochemistry, 38: 605-618, 1999) including retroviruses (Moelling, et. al., *Nat. New Biol.* 234, 240-243, 1971). In procaryotes, three classes of RNase, H1, H2, and H3, have been identified. RNase H1 and H2 share significant sequence homology, whereas RNase H1 and H3 share similar divalent caption and substrate preferences (Wu, et al., J. Bio. Chem., 274 (40):28270-28278, 1999).

Prior to availability of cloned genes and sequence comparisons, eukaryotic RNase H enzymes were classified by their purification characteristics into RNase H type 1 and type 2 (Busen and Hausen, Eur. J. Biochem. 52:179-190, 1975). RNase H type 1 requires $Mg^{2+}$ or $Mn^{2+}$ ions for activity, and remains active in the presence of sulfhydryl reagents such as n-ethyl-maleimide. In contrast RNase H type 2 is active only with $Mg^{2+}$ ions, and is inhibited by $Mn^{2+}$ ions and sulfhydryl reagents. Mammalian RNase H type 1 and type 2 enzymes have been isolated and biochemically characterized in various mammalian tissues including calf thymus (Bilsen, *J. Biol. Chem.* 255: 9434-9443, 1980; Vonwirth, et al., Experientia, 46(3):319-321, 1990), mouse cells (Masutani, et al., *J. Biol. Chem.* 265: 10210-10216, 1990), HeLa cells (Kane, *Biochemistry* 27: 3187-3190, 1988), human erythroleukemia cells (Eder and Walder, *J. Biol. Chem.* 266, 6472-6479, 1991), and human placenta (Frank, et al., *Nucleic Acids Res.* 22: 5247-5254, 1994). RNase H type 2 purified to near homogeneity from human placenta has molecular weight about 33 kDa, is active in a pH range of 6.5-10 with optimum at reduced conditions pH 8.5-9, requires presence of $Mg^{2+}$ ions, and is inhibited by $Mn^{2+}$ ions and sulfhydryls such as n-ethyl-maleimide (Frank, et al., *Nucleic Acids Res.* 22: 5247-5254, 1994).

For reference, *E. coli* RNase H1 belongs to RNase H type 1 (Itaya, *Proc. Natl. Acad. Sci. USA* 87: 8587-8591, 1990), while *E. coli* RNase H2 belongs to RNase H type 2 (Davis, et al., *Science* 252: 88-95, 1991). Although human RNase H1 is homologues to *E. coli* RNase H1, its biochemical properties are similar to those for RNase H type 2, whereas human RNase H2 which is homologues to *E coli* RNase H2, has biochemical properties similar to those of RNase H type 1.

Two human RNase H genes have been cloned and expressed: RNase H1 (Wu, et al., *Antisense Nucleic Acid Drug Dev.* 8, 53-61, 1998; US patent application 2003/0144496, Jul. 31, 2003 to Crooke et al.), and RNase H2 (Frank, et al., *Proc. Natl. Acad. Sci. U.S.A.* 95, 12872-12877, 1998; Cerritelli and Crouch, *Genomics* 53: 307-311, 1998). Human RNase H1 is a 286 amino acid protein expressed ubiquitously in human cells and tissues. The amino acid sequence of human RNase H1 displays strong homology with RNase H1 from yeast, *Escherichia coli*, chicken, and mouse. The human RNase H2 enzyme is a 299-amino acid protein with a calculated mass of 33.4 kDa and is ubiquitously expressed in human cells and tissues (Frank, et al., *Proc. Natl. Acad. Sci. U.S.A.* 95, 12872-12877, 1998). Human RNase H2 shares strong amino acid sequence homology with RNase H2 from *Caenorhabditis elegans*, yeast, *B. subtilis* and *E. coli* (Wu, et al., Antisense Nucleic Acid Drug Dev., 8, 53-61, 1998; Ohtani, et al. Biochemistry 38:605-618, 1999).

Group VI non-specific nucleases comprise enzymes with non-preferential hydrolytic activity towards all nucleic acids. These include including Benzonaze®, an endonuclease isolated from *Serratia marcescens* (Eaves and Jeffries J. Bact. 85: 273-278, 1963; Nestle and Roberts, J. Biol. Chem. 244: 5219-52225, 1969), nuclease CI isolated from *Cunninghamella echinulata* (Ho, et al., Eur. J. Biochem. 256:112-118, 1998) and the like.

Benzonaze® digests nucleic acids to 5'-monophosphate terminated oligonucleotides of about 2-5 bases in length (Nestle and Roberts, J. Biol. Chem. 244: 5219-52225 1969; Janning, et al., Rapid Commun. Mass. Spectrom. 8:1035-1040, 1994). Although the nuclease is capable of cleavage at nearly all positions along a nucleic acid chain, some sequence preferences have been demonstrated (Meiss, et al., Biochemistry 34:11979-11988, 1995). The enzyme prefers GC-rich regions in dsDNA while avoiding d(A)/d(T)-tracts. Structurally the enzyme consists of two identical 245-amino acid subunits of 30 kDa. It is functional between pH 6-10, with optimum pH of 8-9, and from temperatures of 0° C. to 42° C., with optimum at 37° C. The enzyme requires $Mg^{2+}$ for activation in the concentration range of 1-10 mM, with optimum at 1-2 mM. However, the activity is inhibited (approximately 75% reduction in relative activity) in the presence of high concentrations (>150 mM) of monovalent captions (Na+, K+, etc.), which is typical of physiological conditions. Benzonase® is commercially available from Novagen, Epicentre and other suppliers.

Nuclease CI from *Cunninghamella echinulata* var. *echinulata* degrades single-stranded and double-stranded DNA and RNA with about equal cleavage rates. When digesting nucleic acid duplexes, this enzyme recognizes one strand where cleavage takes place, and does not digest the second complementary strand. The nuclease requires $Mg^{2+}$ or $Mn^{2+}$ divalent captions, and is inhibited by metal ion chelators such as EDTA. The optimum activity is at pH=7.0-8.5, in the presence of either 10 mM $Mg^{2+}$ or 5 mM $Mn^{2+}$, exhibiting 100-fold lower activity in the presence of $Ca^{2+}$ ions alone. Enzyme activity significantly decreases below pH about 6.0. The enzyme shows a higher activity at higher temperatures, with optimum temperature of 55 C with $Mn^{2+}$ or 50 C with $Mg^{2+}$ (Ho, et al., Eur. J. Biochem. 256:112-118, 1998).

Group VII artificial nucleases include enzymatic compounds with pre-designed preferential activity towards one or more forms of viral nucleic acids. Artificial biological or chemical nucleic acid cleaving agents that mimic the hydrolytic function of natural enzymes have been developed (Sigman et al., Chem. Rev. 93:2295-2316, 1993; Komiyama and Sumaoka, Curr. Opin. Chem. Biol 2:751-757, 1998; Kramer, Coord. Chem. Rev. 182:243-261, 1999; Ott and Kramer, Appl. Microbiol. Biotechnol., 52:761-767, 1999; Franklin, Curr. Opin. Chem. Biol. 5:201-208, 2001). Artificial nucleic acid cleaving agents include peptides and peptidomimetics that exhibit nucleolytic activity, and chemical nucleases having hydrolytic activity such as lanthanide-ion complexes (Wan, et al. Chin. Sci. Bull. 45(22): 2017-2028, 2000; Sigman et al., Chem. Rev. 93:2295-2316, 1993). Synthetic polymers have been used as backbones of artificial nucleases. The artificial metallonuclease was obtained by random attachment of Cu(II) complex of Cys to cross-linked polystyrenes (Jung, et al. J. Am. Chem. Soc. 120:12008-12016, 1998; Suh, Acc. Chem. Res. 36:562-570, 2003). Fully-synthetic molecules have been also designed as nuclease mimics by either using peptidic or non-peptidic backbones.

A short peptide capable of hydrolytic cleavage activity with multiple categories of natural substrates including nucleic acids and proteins is Ser-His (L1, et al., Bioorganic & Medicinal Chemistry 8(12): 2675-2680, 2000). Seryl-histidine (S-H) di-peptide and seryl-histidine-aspartate (S-H-D) tri-peptide can non-specifically cleave molecules of single-stranded or double-stranded DNA and RNA that are linear, circular or super-coiled, and therefore can be applied to prevention and treatment of viral diseases.

In design of protein-based nucleases, a catalytic group from a natural enzyme active site or from another peptide-based entity with similar catalytic properties may be chosen as the active group of the artificial nuclease. For example, mimics of RNase A that digest ssRNA can be obtained by coupling two or four imidazole groups (Breslow and Labelle, J. Am. Chem. Soc. 108(10):2625, 1986; Breslow, Acc. Chem. Res. 24(11): 317, 1991) with nucleic acid intercalators such as acridine (Lorente, et al. Tetrahedron Letters 37(25):4417, 1996). Ribozyme mimics carrying oligonucleotides complementary to the selected site can carry out site-directed RNA scission (Ciesiolka et al., Eur. J., Bioch. 204, 575-581, 1992).

Artificial nucleases can be designed as polypeptides comprising two domains: a nucleic acid-binding domain and a metal-binding domain. The nucleic acid-binding domain may be any amino acid sequence that specifically binds to a nucleic acid sequence, e.g. a sequence present in a viral dsDNA, ssDNA, dsRNA, ssRNA, RNA-DNA hybrid, B-DNA, A-DNA, or the like. The metal binding domain may be located within the nucleic acid-binding domain, and binds any metal such as Ca(II), Eu(II), Zn(II), Cr(IV), Cd(II), Ce(III), Fe(III), Co(III), Cu(II) and preferably binds a hydrolytic metal such as a lanthanide. The hydrolytic polypeptides may comprise the following amino acid sequences: TERRRQQLDKDGDGTIDEREIKIHFQNK-RAKIK (SEQ ID NO: 4), TERRRFDKDQNGYIGAADL-RHVKIWFQNKRAKIK (SEQ ID NO: 5), TERRRFRVFD-KDGNGYISAAEKIWFQNKEAKIK (SEQ ID NO: 6), TRRRRFSLFDKDGDGTITTKEEVWFQNRRMKWK (SEQ ID NO: 7), DEKRPRTAFSGEQLARLKREFNEN-RYLTERRRLRVFDKDGNGFISAAEKIWFQN
KR-AKIKKST (SEQ ID NO: 8), or a catalytically active portions of these polypeptides thereof (US patent application No. 2002/0.146788 to Franklin, incorporated here by reference in its entirety). A $Zn^{2+}$-binding peptide P1: Asp-Pro-Asp-Glu-Leu-Glu-His-Ala-Ala-Lys-His-Glu-Ala-Ala-Ala-Lys-CONH$_2$ (SEQ ID NO: 9), tethered to DNA-intercalating rhodium complex has been shown to hydrolytically digest plasmid DNA and oligonucleotide substrates (Copeland, et al., Biochemistry 41:343-356, 2002; Fitzsimmons and Barton, J. Am. Chem. Soc. 119: 3379-3380, 1997).

Chemical nucleases and other artificial nucleic acid cleaving agents based on metal complexes can be further divided in two main groups according to their mechanisms of action: free radical or oxidative cleavage or phosphodiester bond hydrolysis. Some free radical cleavage agents such as EDTA-Fe$^{2+}$, Cu(phen)$_2^+$ and other transition metal based compounds abstract hydrogen atoms with hydroxyl radicals generated through a Fenton reaction with hydrogen peroxide (Wan et al., Chin. Sci. Bull., 45:2017-2028 (2000). Some artificial nucleases possess specific hydrolytic activity towards a particular form of DNA and/or RNA. The free radical cleavage activity of Cu(phen)$_2^+$ has specificity towards right-handed double-stranded B-DNA, and is about 6-7-times less reactive towards a wider and flatter helix of double-stranded A-DNA, about 50-times less reactive towards left-handed double-stranded Z-DNA compared to B-DNA, and has little reactivity towards single-stranded DNA (Kuwabara, et al., Biochemistry, 25(23):7401 (1986). The compound is also active against single-stranded RNA, but has no reactivity on double-stranded RNA (Murakawa, et al. Nucleic Acid Res. 17(130):5361, 1989).

Just as with natural nucleases, artificial nucleic acid cleaving agents that catalyze phosphodiester bond hydrolysis rather than employ an oxidative mechanism are more desirable for clinical applications. Hydrolytic cleavage does not require redox-active co-reactants, and results in strand ends that cannot be relegated by enzymes. Furthermore, oxidative action produces highly-reactive and diffusible free radicals and metal oxenes (Sigman et al., Chem. Rev. 93:2295-2316, 1993). However, while chemical nucleases such as metal-ion complexes have potential cytotoxicity, these may have practical applications in treatment of viral infections in wild animals, birds, insects and plants.

Metal-ion promoted hydrolysis of RNA with lanthanides is known (Rordorf and Kearns, Biopolymers 15:1491-1504, 1976; Magda, et al., J. Am. Chem. Soc. 116:7439-7440, 1994; Hall, et al., Chem. Biol. 1:185-190, 1994), as is hydrolysis with transition metals (Hegg, et al., Inorg. Chem. 36:1715-1718, 1997; Chapman et al., J. Am. Chem. Soc. 117:5462-5469, 1995 and Morrow, et al., Inorg. Chem. 31:16-20, 1992). The 2'-hydroxyl ribose ring makes RNA nearly 100,000-fold times more reactive towards hydrolysis than DNA, and a complementary DNA oligonucleotide can be used to target site-specific cleavage of viral RNA (Thompson, et al. Biorg. Chem. 23: 471-481, 1995). Both oxidative (Zheng, et al., J. Am. Chem. Soc. 118:2320-2325, 1996) and hydrolytic (Brown et al., Nature 303: 543-546, 1983) cleavage agents are generally less reactive towards double-stranded RNA compared to single-stranded RNA. Without being limited by any particular mechanism or theory, these differences might arise from structural features of RNA duplexes. Duplex RNA adopts an A-type of double-helix which has much deeper and narrower major groove than B-DNA, and as a result many agents that bind to double-stranded DNA can not bind to dsRNA. Further, duplex RNA is less flexible that single-stranded RNA, hence hydrolysis of 2'-OH may be inhibited, due to orientation of the substrate (Kolasa, et al. Inorg. Chem. 32: 3983-84, 1993). However, some smaller size transition metal complexes such as Cu([9]aneN$_3$)Cl$_2$ are effective in cleaving both ssRNA and dsRNA (Hegg, et al., Inorg. Chem. 36:1715-1718, 1997). A complex of Cu([9]aneN$_3$)Cl$_2$ attached to a flexible bi-functional PEG equipped with viral nucleic acid targeting oligomers can be used for cleavage of viral double-stranded RNA. Oligonucleotide-bound Fe(III)/EDTA complexes can selectively hydrolyze RNA molecules (Brown et al., Nature, 303, 543-546, 1985).

Site-selective RNA hydrolysis has been shown with acridine-tethered oligonucleotides, which interact with the RNA and activate the target phosphodiester linkages (Ciesolka et al., Eur. J. Biochem 204, 583-589, 1992). Bulge sites in RNA, formed by acridine-bearing oligonucleotides, are then preferentially hydrolyzed by unbound lanthanide complexes (Kuzuya, et al. J. Am. Chem. Soc. 124:6887-6894, 2002; Husken, et al., Biochemistry 35:16591-16600, 1996; Michailovski et al., Biochemie, 78, 131-138, 1996).

Hydrolytic cleavage of DNA by metal ion complexes is more challenging, because of the comparative stability of the DNA phosphodiester bond under physiological conditions (Williams, et al. Acc. Chem. Res. 32:485-493, 1999; Westheimer, F. H. Science 235:1173-1178, 1987). Although many naturally occurring nucleases described in this invention can be successfully used for antiviral applications the design of small molecular agents that can bind DNA at specific sequence of interest and cleave DNA hydrolytically with the rates comparable to those of natural nucleases continues to be of great interest. So far only a handful of small molecules have been reported to cleave DNA hydrolytically all relying on transitional or lanthanide metals (Branum, J. Am. Chem. Soc., 123: 1898-1904, 2001; Sreedhara and Cowan, J. Biol. Inorg. Chem., 6: 337-347, 2001).

Small molecule lanthanide Ln(III)-ion complexes are particularly suitable as catalytic centers for hydrolytic digestion of DNA (Franklin, Curr. Opin. Chem. Biol. 5:201-208, 2001). Cerium Ce(IV)-ion is a lanthanide that can access a tetravalent oxidation state under aqueous conditions. The Ce(IV) is among the most effective metal ions for double-stranded DNA hydrolysis, providing DNA hydrolysis rates of 20-1000-times faster than Ln(III) ions (Komiayma, Che. Comm: 1443-1451, 1999). Site selective preferential hydrolysis of double-stranded DNA has been achieved due to substantially greater substrate specificity of Ce(IV)/EDTA complex for single-stranded DNA. A single-stranded structure having a bulge or gap at the target double-stranded DNA due to a modified oligonucleotide, is a suitable substrate for unbound Ce(IV)/EDTA complex is applied (Kitamura and Komiyama, Nucleic Acid Res. 30(19): 102-108, 2002). In summary, the native and/or modified nucleases of animal, insect, bacterial or plant origin, as well as artificial nucleases described herein have an antiviral activity due to hydrolytic digestion of nucleic acid, and can be directed towards a specific form of a virion nucleic acid or towards an intermediate viral nucleic acid appearing in the course of viral replication, for the animal, bacterial, insect and plant viruses described herein.

In one aspect, this invention provides antiviral nucleases that are chemically/genetically modified to contain non-natural amino acids. A semi-synthetic approach has been used to site-specifically incorporate non-natural amino acids into proteins. In this technique, segments of proteins are synthesized by solid phase peptide synthesis and the segments are either chemically (Dawson, et al. Science 266, 776-779, 1994) or enzymatically (Southworth, et al. Bio-Techniques 27:110-120, 1999) ligated. Semi-synthetic methodologies are generally limited to synthesis of proteins with a molecular mass less than 10 kDa (Merrifield, Science 232: 341, 1986); Jackson et al., Science 266, 243, 1994); Dawson and Kent, Annu. Rev. Biochem., 69: 923, 2000). Expressed protein ligation (EPL) allows chemical ligation of larger proteins containing genetically encoded non-natural amino acids with synthetic peptides or small proteins containing synthetic non-natural amino acids (Miur, et al. Proc. Nat. Ac. Sci., USA 95:6705-6710, 1998; Hoffman and Miur, Current Opinion in Biotech. 13: 297-303, 2002). EPL involves ligation of a thioester-modified C-terminal of a recombinant protein to an N-terminal cysteine of a synthetic peptide and therefore is limited to incorporation of non-natural amino acids into a C-terminus of the recombinant protein.

A biosynthetic in vitro method based on amber codon suppression has been developed allowing site-specific incorporation of non-natural amino acids into proteins (Noren, et al. Science 244:182-188, 1989; Bain, et al., J. Am. Chem. Soc. 11:8013-8014, 1989). This technique involves amber suppressor aminoacyl-tRNA that is chemically modified with a desired non-natural amino acid residue, wherein the resulting aa$^u$-tRNA is then added in vitro together with mRNA and DNA containing a gene of interest having an amber stop codon (UAG) at the desired site. Since only the amber codon can be used for suppression, this technique allows incorporation of only one kind of non-natural amino acid into the protein of interest. Using this technique, a ketone handle-containing amino acid has been site-specifically incorporated into proteins in vitro and subsequently modified with small molecule fluorophore and biotin derivative (Wang, et al., Proc. Nat. Ac. Sci. USA 100(1):56-61, 2003; Cornish, et al., J. Am. Chem. Soc. 118:8150-8151, 1996).

The reactive thiol group of cysteine has been used extensively for protein modification, including attachment of folic acid to RNase A (U.S. Pat. No. 6,280,991 to Raines, 2001), attachment of multi-charged moieties to proteases (US patent application 2002/0127695 to Davies, et al., 2002), and attachment of various biophysical probes (Gaietta, et al., Science 296:503-507, 2000). However, the site selective reaction with a cysteine residue is often complicated by presence of more than one reactive cysteine residue in a protein, as well as exchange reactions in the presence of free thiol when a disulfide linkage is formed. Therefore, the availability of a non-natural amino acid with orthogonal reactivity allows for site-selective modification of a protein, when a single cysteine can not be site-selectively modified or when two different site-specific modifications are required.

A technology that allows site-specific insertion of two different non-natural amino acids has been the use of an mRNA having a four base codon, in combination with a chemically aminoacylated mutant tRNA with a cognate four base anticodon (Moore, et al., J. Mol. Biol. 298:195-209, 2000). This approach allowed insertion of two different non-natural amino acids into a protein (Hohsaka, et al., J. Amer Chem Soc 121: 12194-12195, 1999; Hohsaka and Sisido, Curr. Opin Chem Biol 6:809-815, 2002).

A potentially general method for importing chemically aminoacylated suppressor tRNA into mammalian cells has been demonstrated, using two suppressors of amber and ochre codons derived from E. coli tRNA aminoacylated with tyrosine, which were imported into cells using a transfecting reagent Effectene. Active chloramphenicol acetyl transferase was expressed from co-transfected chloramphenicol acetyl transferase genes containing the amber or ochre codon at an internal site (Kohrer, et al., Proc Nat Acad. Sci. 98:14310-14315, 2001; Kowal, et al. Proc. Nat. Acad Sci 98: 2268-2273, 2001).

Biosynthetic methods in vivo can enable protein modification with non-natural amino acids. An expanded genetic code (EGC) technique allows insertion of genetically encoded non-natural amino acids both in eukaryotes such as Saccharomyces cerevisiae (Chin et al, Science, 301:964-967, 2003), and prokaryotes such as E. coli (Wang, et al. Science 292:498, 2001; Doring et al., Science 292:501-504, 2001). The EGC technique involves generation of a novel suppressor tRNA-codon pair and an aminoacyl-tRNA synthetase (aaRS) that incorporates a non-natural amino acid. The new tRNA and aaRS should be orthogonal to the endogenous tRNA and aaRS in the cell to avoid cross aminoacylation, and they should function efficiently with the translational apparatus (Wang and Shultz, Chem. Comm. 1, 2002).

Using this technique more than 13 non-natural amino acids with novel functionalities were encoded in E. coli (Wang, Ph. D. Thesis, UC Berkeley, 2002) including p-acetyl-L-phenylalanine with a versatile keto group serving as an unique chemical handle for subsequent chemical modification with any moiety containing a hydrazine group (Wang, et al., Proc. Nat. Ac Sci. USA 100:56, 2003). EGC methodology using genetically encoded aminoacyl-tRNA synthetase/tRNA pairs has been extended to eukaryotic cells such as Saccharomyces cerevisae. (Hughes, Funct. Integr. Genomics 2:199, 2002). The chosen orthogonal pair was the amber suppressor tyrosyl-tRNA Synthetase (Tyr-RS)/tRNA$_{CUA}$ pair from E. coli. E. coli Tyr-RS efficiently aminoacylates E. coli tRNA$_{CUA}$, when both are encoded in S. cerevisae, but this pair not aminoacylate S. cerevisae cytoplasmic tRNAs. In addition, E. coli tyrosyl tRNA$_{CUA}$ is a poor substrate for S. cerevisae aminoacyl-tRNA synthetases, and it functions efficiently in protein translation in S. cerevisae (Edwards, et al. Proc. Nat. Ac Sci. USA 88:1153, 1991). Moreover E. coli does not have an editing mechanism and therefore does not proofread an non-natural amino acid ligated to tRNA. In order to alter orthogonal E. coli Tyr-RS amino acid specificity so it aminoacylates E. coli tRNA$_{CUA}$ with a desired non-natural amino acid, for example, p-acetyl-L-phenylalanine with the keto handle and none of the endogenous amino acids Tyr-RS have been mutated and grown in the presence of 1 mM of p-acetyl-L-phenylalanine residue. As a result a mutant Tyr-RS was selected with higher activity for p-acetyl-L-phenylalanine than for natural amino acids. Five non-natural amino acids including p-acetyl-L-phenylalanine with the keto functional group were efficiently incorporated into proteins with high fidelity in response to the nonsense codon TAG (Chin, et al. Chem & Biol. 10:511-519, 2003); Chin, et al, Science 301:964-967, 2003).

Encoding of non-natural amino acids into the nucleases as described herein makes it possible to tailor changes in antiviral nucleases in live mammalian cells, and therefore antiviral properties of genetically modified nucleases such as their hydrolytic activity towards viral nucleic acids under the presence of nuclease inhibitors can function directly in vivo.

An important factor affecting catalytic activity of enzymes is distant or long-range electrostatic interactions between the enzyme and its substrate. Such interactions between the charged amino acid residues of the nuclease and its protein inhibitor, or between the nuclease and the charged backbone of its substrate, may take place before the physical contact is made or when the charged moieties that do not make physical contact due to some steric hindrance. Increased local electrostatic attraction of "cationized" human DNase I (having mutations that cause a charge change of +5) toward negatively charged phosphates on the viral DNA backbone makes the genetically modified enzyme effective in binding to viral DNA. Such binding occur even at low concentrations of viral DNA in blood or in infected cells. Indeed even in the case of the most aggressively replicating viruses, such as hepatitis B (HBV) having peak DNA level reaching $10^{10}$ copies/ml, the weight concentration of 6 kb HBV DNA is below 33 ng/mL. Peak concentration of HBV DNA is comparable with the lower limit of typical concentrations of endogenous cellular DNA in a human, ranging from 25 ng/ml to 250 ng/ml (Pan, et al., J. Biol. Chem. 273, No 29: 18374-381, 1998). In the case of human cytomegalovirus (CMV) having a large dsDNA genome (1,229 kbp), peak DNA level does not exceed $10^5$ copies/ml, resulting in the weight concentration of CMV DNA below 12 pg/mL.

Embodiments of the invention provide antiviral compositions having genetically enhanced nucleases produced by genetic encoding techniques in vivo, and/or semi-synthesis in vitro as described above. The modified nucleases contain non-natural amino acids, such as multi-charged lysine having a more positively charged and bulky side chain group than natural lysine (Bioorg. & Med. Chem. 7:2985-2990, 1999), and/or a non-natural p-acetyl-L-phenylalanine residue carrying the keto group, which is useful for subsequent chemical modification, and/or a selenocysteine, a homoarginine and/or one or more D-amino acids, etc.

The genetically enhanced nucleases of Group I dsDNA-specific nucleases are exemplified by hyper-active actin-resistant uncommon mutant variant of human DNase I obtained by the following substitutions Q11R/E13KU$^{(2+)}$/N74KU$^{(2+)}$/A114FU$^{(keto)(+5)}$ with additional five positive charges compared to native DNase I, wherein KU$^{(2+)}$ is non-natural lysine with two positively charged side-chain amine groups and FU$^{(keto)}$ is non-natural p-acetyl-L-phenylalanine residue carrying the keto group.

The genetically enhanced Group IV ssRNA-specific nucleases are exemplified by ribonuclease inhibitor (RI)-resistant and non-toxic uncommon mutants of human RNase I obtained by the following substitutions K1FU$^{(keto)}$/Q11A/N71A/E111A; and human RNase S consisting of truncated S-peptide (1-15 amino acid residues fragment) obtained by the following substitutions K1FU$^{(keto)}$/Q11A; and truncated S-protein (residues 21-124 amino acid residues fragment) obtained by the following substitutions N71A/G89FU$^{(keto)}$/E111A, wherein FU$^{(keto)}$ is non-natural p-acetyl-L-phenylalanine residue carrying the keto group.

In another embodiment of this invention the chemical/genetic modifications of antiviral nucleases comprise semi-synthetic nucleases obtained via either native chemical ligation wherein a chemically-synthesized peptide is ligated to another peptide or protein with use of C-terminal thioester and N-terminal cysteine residue (Dawson, et al., Science 266:776-779, 1994), or via intein-mediated protein ligation, which requires a cysteine residue at the ligation site (Evans, et al. Protein Sci. 7, 2256-2264, 1998), and wherein the C-terminal thioester is created by cleavage of a fusion protein consisting of the target protein and an intein in the presence of a thiol reagent (Arnold, et al., The Scientific World Journal 2: 1823-1827, 2002).

In yet another embodiment, this invention provides the synthesized hydrolytic oligopeptides such as dipeptides: Ser-His, His-Asp, Cys-His; tripeptides: Ser-His-Asp, Ser-His-Gly, Ser-His-His, His-Phe-Asp and His-Lys-His; tetrapeptide: Glu-His-Asp-His hexapeptides: Gly-Phe-Ser-Leu-His-Ala (SEQ ID NO: 10), Phe-Ser-Phe-Leu-His-Ala (SEQ ID NO: 11), and Ser-Ser-Phe-Leu-His-Ala (SEQ ID NO: 12); octapeptides: Arg-Arg-Trp-His-Arg-Leu-Lys-Glu (SEQ ID NO: 13) undecapeptides: Ser-Gly-Gly-His-Gly-Gly-Arg-Gly-Gly-His-Phe (SEQ ID NO: 14), Ser-Gly-Gly-Ser-Gly-Gly-Ser-Gly-Gly-His-Phe (SEQ ID NO: 15), Ser-Gly-Gly-Arg-Gly-Gly-His-Gly-Gly-His-Phe (SEQ ID NO: 16) having at least one natural amino acid residue replaced by a non-natural amino acid residue as D-Ser/L-Ser and D-methyl-Asp/L-Asp, Phe/FU$^{(keto)}$ and other substitutions resulting in oligopeptides with increased proteolytic resistance and enhanced oral bioavailability.

In yet another embodiment the invention provides multiple natural or modified di/tri peptides, hexapeptides and undecapeptides covalently attached to a large molecular mass polymeric carrier targeted to unprotected viral nucleic acids inside infected cells. Such antiviral complexes with enzymes (ACE) are characterized by enhanced therapeutic efficacy, strong proteolytic resistance, long half-life, low immunogenicity and high cellular uptake.

The conjugation of an antiviral nuclease to a polymeric carrier can be accomplished via one or more of multiple routes known in the art of protein chemistry. The polymeric carriers of this invention comprise a single or a plurality of molecular scaffolds upon which one or more antiviral nucleases and various targeting moieties may be attached. Exemplary polymeric carriers include poly(ethylene glycol) (PEG), HPMA (Poly-[N-2(2-hydroxypropyl)methacrylamide]); carboxymethylcellulose; dextran; polyvinyl alcohol; polyvinyl pyrrolidone; poly-1,3-dioxolane; poly-1,3,6-trioxane; polypropylene oxide; poly(ethylene/propylene glycol); an ethylene/maleic anhydride copolymer; a polypropylene oxide/ethylene oxide copolymer; a polyethylene glyco/thiomalic acid copolymer; derivatives of PEG such as PEG-[NH2]$_n$; copolymers such as [PEG-Lys]$_n$, PEG-PEI, PAMAM, PAMAM(EDA); and poly(Lysine) dendrimers, as well as polymers and copolymers of amino acid residues such as poly(Lys-Glu), poly(Lys-Ala-Glu-Tyr), etc., proteins such as human serum albumin, or any combination thereof.

The preferred polymeric carriers of compositions provided herein are PEG and PEG-derivatives, PAMAM dendrimers and their derivatives, and any combinations thereof having a total molecular weight below 200 kDa. Proteins conjugated to PEG and PEG-derivatives were found to have enhanced proteolytic resistance, markedly improved circulating half-life as a result of increased hydrodynamic radius of the protein-polymer conjugate, reduced antigenicity, immunogenicity and toxicity, improved solubility, thermal and mechanical stability (Chapman, Adv Drug Del Rev 54:531-545, 2002); Harris, Ed., Poly(Ethylene Glycol) Chemistry: Biotechnical and Biomedical Applications, Plenum Press, N Y, 1991).

A method of attaching a protein to a polymeric carrier is via the nonselective conversion of one or more of the ε-amino group of lysine, the ring amine group of histidine, or the α-amino group of N-terminus residues of the protein into amides with the subsequent loss of positive charges (Abuchovsky et al., J. Biol. Chem. 252: 3571-3581 & 3582-3586, 1977; Harris (Ed.), Poly(Ethylene Glycol) Chemistry: Biotechnical and Biomedical Applications, Plenum Press, N Y, 1991; Zalipsky, Bioconj. Chem. 6:150-165, 1995; Francis et al., Int. J. Hematol. 68:1-18, 1998).

However the multiplicity of potential attachment sites throughout any given protein may lead to variable degree of modification and significant decrease in bioactivity of protein in protein-polymer complexes. For example, non-selective conjugation of superoxide dismutase with PEG inactivated some fractions of the modified enzyme inactivated (McGoff et al., Chem. Pharm. Bull. 36: 3079-3091, 1988). Synthesized PEG$_2$-IFN conjugate via attachment of forked mPEG$_2$-NHS (ω-N-hydroxysuccinimidyl ester) to ε-amino groups of one of the four Lys$^{31}$, Lys$^{121}$, Lys$^{31}$ to Lys$^{134}$ of interferon α-2a (INF) at pH of about 9 maintained only 7% of the anti-viral activity of free interferon in vitro (Bailon, et al., Bioconj. Chem. 12:195-202, 2001).

As provided herein, site-specific attachment of polymer to protein, for example, by site-specific derivatization of cysteines, leads to more predictable and generally higher level of the biological activity of the protein in protein-polymer complexes. Cysteine occurs less frequently in proteins than lysine, about 1.7% versus 5.7% of all residues, and is mostly confined in unreactive double-sulfide bonds. A single cysteine introduced into protein by site-specific mutagenesis can be derivatized by thiol-specific maleimide-based or haloacetamide-based reagents (Goodson et al., Biotechnology 8, 343-346, 1990; Chikoti et al., Bioconjugate Chem. 5, 504-507, 1994; Messmore, at al. J. Am. Chem. Soc. 117 (31): 8057-8060, 1995).

An alternative strategy involves attaching polymers at N-terminal amino acid residues of protein. Examples include selective oxidation of N-terminal serine or threonine to the corresponding aldehyde and subsequent coupling with hydrazine, alkoxyamine or hydrazide derivatives (Geoghegan and Strogh, Bioconjugate Chem. 3, 138-146, 1992). More recently PEG carrying a single aldehyde group (mPEG-CHO) has been attached to recombinant human G-CSF, a protein used to treat hematopoietic disorders, and to human leukocyte interferon commonly referred to as consensus interferon IFN-con (US patent application 2003/0096400 to Kinstler May 22, 2003). The reaction included reducing alkylation conditions at acidic pH 4.0 to selectively activate the α-amino group at the protein amino-terminus. G-CSF with 6 kda PEG attached to its N-terminus retains 68% of activity in vitro, while the same protein having PEG non-selectively attached to both lysine and N-terminal amines retained only 21% of its activity. The benefits of N-terminal modification differ from protein to protein, thus IFN-con with 12 kDa PEG covalently attached to its N-terminus has been shown to retain only 20% of in vitro activity (US patent application 2003/0096400 to Kinstler May 22, 2003).

Hetero-bi-functional PEG derivatives such as ω-N-hydroxysuccinimidyl ester-PEG-propionaldehyde (NHS-PEG-CHO), as well as multivalent polymeric carriers can be used to link the antiviral nucleases of the present invention to various drug delivery enhancement ligands. For example the NHS groups can be conjugated to ε-amino groups of lysine-terminated ligand under mild alkaline conditions, at a pH of about 8.0, while CHO group can be conjugated to α-amino groups at nuclease N-termini at acidic pH of about 5.0.

Site-specific PEG-derivatization of C-terminal has heretofore been demonstrated using short synthetic peptides. Aβ-peptide, a 40-43 amino acid proteolytic fragment of the β-Amyloid precursor protein, has been coupled with 3 kDa PEG through its C-terminus using standard Fmoc protocols on PAP Tenta-Gel (Burkoth et al., J. Am. Chem. Soc. 120:7655-7656, 1998; Bayer and Rapp in Poly(Ethylene Glycol) Chemistry: Biotechnical and Biomedical Applications, M. Harris Rd, Plenum Press, NY pp. 325-345, 1992). Human growth hormone-releasing factor (hGRF) analogs were pegylated at the C-terminus, using each of a solid and solution-phase strategy. Each peptide was extended using $(Gly)_2$-Cys-$NH_2$ spacer, demonstrated not to alter intrinsic biological activity and was pegylated at the C-terminus using an X and dithiopyridyl-PEG reagent (Campbell, et al., J. Pept. Res. 49:527-537, 1997).

In an embodiment of this invention, C-terminal modification of genetically modified nuclease with $(Gly)_n$-Cys extension at its C-terminus was carried out using S-cyanocysteine (Cys-CN) conversion chemistry. The genetically modified human RNase I with added peptide $(Gly)_m$-Cys, with m of about 2-4 at its C-terminus was covalently attached to amino-group terminated PEG immobilized on a solid resin. The amino-group carrying polymers can include multi-armed branched R-$[PEG-NH_2]_n$, $[PEG-Lys]_n$, $NH_2$-terminated dendrimers, PEI-PEG copolymers and other polymers. The reaction involves cleavage at cysteine residue at the C-terminal. Conversion of free cysteine residues in proteins to residues of S-cyanocysteine (Cys-CN) can be accomplished under mild conditions using the reagent 2-nitro-5-thiocyanobenzoic acid (NTCB; Takenawa et al. J. Biochem. 123:1137-1144, 1998; Jacobson, et al., J. Biol. Chem. 248(19):6583-6591, 1973; Degani and Patchornik, J. Org. Chem. 36:2727, 1971).

In a related embodiment the invention provides antiviral nucleases that are genetically modified by having N or/and C-terminal of the nuclease, fused to human albumin (HA) to prepare a human albumin fusion antiviral nuclease, such that a human albumin fusion antiviral nuclease may be also produced by inserting an antiviral nuclease into an internal region of HA. Fusion of antiviral nucleases such as human DNase I, DNase-α, DNase-β, DNase-γ, human RNase I, human RNase III, etc. can be carried out using the method of US patent application No. 20030171267 of Sep. 11, 2003 to Rosen, et al., incorporated herein by reference in its entirety, in regards to various human albumin fusion proteins, and including therapeutic proteins listed in Table I of US patent application No. 20030171267, such as human interferon, growth hormone, interleukin-2, calcitonin, and others.

In yet other embodiments, antiviral compositions provided herein are native and/or chemically/genetically enhanced antiviral nucleases covalently associated with hetero-bi-functional polymers, the hetero-bi-functional polymers associated directly or through multivalent molecular scaffolds such as dendrimers or star polymers with multiple targeting ligands of various functions.

The invention in other embodiments provides "shell-core" complexes of multivalent molecular scaffolds, and a method of making such complexes. The terminal groups of the multivalent molecular "shell"-scaffolds exemplified by PAMAM dendrimers, are chemically modified to include sequence-specific oligonucleotides, which undergo Watson-Crick hybridization and subsequent covalent bond formation with complementary that are oligonucleotides that are associated with a similarly-modified "core" dendrimer.

The covalent binding of each complementary base-paired oligo- or polydeoxynucleotides can be carried out by the use of bifunctional reagents exemplified but not limited to heterofunctional polyalkylating agent N,N,N'-tri-(β-chloroethyl)-N'-(p-formylphenyl)propylene diamine-1,3. The reagent is attached to the oligo- or polydeoxynucleotide through a highly reactive aliphatic β-chloroethylamino group. The reactivity of the potentially active aromatic alkylating group is strongly inhibited by a neighboring formyl residue. This group is activated when needed after base-pairing of oligonucleotides, by activation through reduction of the formyl residue using sodium borohydride. The preferred oligonucleotides are nuclease resistant and non-toxic Locked Nucleic Acids (LNA), although any modified nuclease-resistant antisense oligonucleotides can be used for this purpose. LNA is a bicyclic RNA analog in which the ribose moiety in the sugar-phosphate backbone is constrained structurally by a methylene bridge between the 2'-oxygen and the 4'-carbon atoms (Koshkin, et al. Tetrahedron 54:3607-3630, 1998); Koshkin, et al. J. Am. Chem. Soc. 120: 13252-13253, 1998).

The targeting ligands may comprise modified oligomers that are sequence-specific for a viral nucleic acid target sequence, and may further comprise one or more of: peptide nucleic acids (PNA) including bis-PNA; locked or bridged nucleic acids (LNA/BNA) capable of forming stable duplexes with single-stranded and double-stranded DNA and RNA, phosphoroamidate oligonucleotides that are sequence-specific binding for viral double-stranded and single-stranded viral DNA and RNA; morpholino oligonucleotides with morpholino nucleosides; linked together by phosphorodiamidate groups which form stable sequence specific complexes with ssRNA, S-DNA (phosphorothioate); pyrrolidine-amide oligonucleotide mimic POM with very high affinity to complementary ssRNA and ssDNA while exhibiting kinetic binding specificity for RNA over DNA and other oligomers; hairpin polyamides; zinc-finger peptides with binding affinity to single-stranded and double-stranded viral nucleic acids (Koizumi et al., Nucleic Acids Res. 31, 3267-3273, 2003; Hickman, et al., Chem. Commun. 32:2251-2252, 2000); and novel classes of modified peptide nucleic acids such as hydroxyproline peptide nucleic acids (HypNA), serine peptide nucleic acid (SerNA) oligonucleotide analogs including their monomers, homodimers, heterodimers and homopolymers and heteropolymers of these and other oligonucleotide analogs shown for example in the US patent application 2003/0059789 Mar. 27, 2003 to Efimov, et. al.

Standard bases such as adenine, thymine, uracil, cytosine and guanine and rare natural and synthetic bases such as dihydrouracil, 4-thiouracil, pseudouracil, hypoxanthine, wybutosine, 5'-uracil, 5-methylcytosine, 5-methyladenine, 2'-O-methylcytosine, 1-N-methyladenosine, 2,2-N-dimethylguanine, 7-methylguanine, and like being attached to ribose or to deoxyribose or to 2'-4'-cyclic ribose, or to other derivatives of pentoses or like, can be used to form nucleosides are when phosphorylated to form nucleotides. Oligo- and polynucleotides composed from nucleotides containing pentose 2-O-4'-C-methylene bridge form locked or bridged nucleic acids (LNA/BNA; Petersen and Wengel, Trends in Biochem. 21, 74-81, 2003). The 2-O-4'-C-ethylene-bridged nucleic acids (ENA) are particularly strongly base paired to the complementary nucleotide sequences of RNA and DNA (Koizumi et al., Nucleic Acids Res. 31, 3267-3273, 2003). PNA, LNA/BNA, ENA, phosphorothioate and phosphoramidate oligo- and polynucleotides are resistant to nucleases. Targeting ligands comprising nuclease-resistant oligonucleotides that are complementary in nucleotide sequence to the selected nucleotide sequences of viral single-stranded or double-stranded DNA or RNA can function in compositions to target, i.e., can direct nucleases or nuclease-polymer complexes to viral nucleic acids inside virus infected cells.

In addition to serving as targeting ligands for hydrolytic digestion of targeted viral nucleic acids by nucleases, the sequence specific oligomers exhibit their own antiviral action via multiple pathways. This is exemplified by but not limited to antisense oligonucleotides that have a phosphorothioate/2'-O-methyl backbone. Methylation at a 2'-position of ribose results in significantly decreased toxic side effects, and increased antiviral efficacy as has been shown by inhibiting human immunodeficiency virus 1 (HIV-1) replication by blocking the interaction between gp120 and CD4 (Kuwasaki, et al., J. Antimicrob. Chemo. 51: 813-819, 2003); Stein, et al., J. AIDS 4: 686-93, 1991), and inducing degradation of the target nucleic acid sequence by endogenous RNase H (Mishra, et al., Biochem. Pharm. 61: 467-76, 2001).

In addition to interfering with the translation process via an RNA-DNA duplex formation, antisense phosphorothioate oligonucleotides were shown to block the proliferation of HIV-1 in acutely infected cells in a non-sequence-specific manner (Matsukura, et al., Proc. Nat. Ac. Sci., USA 84: 7706-10, 1987), most likely by the inhibition of the reverse transcriptase (RT) (Bioziau, et al., Proc. Nat. Ac. Sci., USA 89: 768-72, 1992; Majumdar et al, Biochem. 28: 1340-6, 1989). Phosphorothioate-containing oligonucleotides have been shown to inhibit avian myeloblastosis virus (AMV) RT, Pol I (Klenow fragment), human polymerases α, β, and γ (Marshall, et al., Proc. Nat. Ac. Sci., USA 89: 6265-6269, 1992; Gao, et al., J. Biol. Chem. 264: 11521-11526, 1989), and human DNA polymerases and RNase H (Gao, et al., Mol. Pharmac. 41: 223-229, 1992). Use of short G-rich oligonucleotides can interfere with the gp120/CD4 interaction or HIV integrase activity (Jing, Expert Opin. Investigate. Drugs 9: 1777-1785, 2000). These oligomers form tetramers stabilized by G-quartets, which leading to anti-HIV-1 activity (Jing, et al., J. Biol. Chem. 275, 3421-30, 2000).

The targeting ligands for antiviral nuclease-derived compositions provided herein include membrane permeating peptides (MPP) to facilitate intracellular delivery of the macromolecular nuclease and nuclease-polymer complexes. The poly(Arginine) based MPP has been proposed as a drug carrier enhancing delivery of various compounds across epithelial tissues, including the skin, gastrointestinal tract, pulmonary epithelium, and the like (US patent 2003/0083256 of May 2003 to Rothbard, et al.). MPPs have been used as carrier molecules for intracellular delivery of various exogenous molecules, such as from small bioactive molecules with low membrane permeability, such as cyclosporin A (Rothbard et al., Nat. Med. 6:1253-1257, 2000) and oligoDNAs (Astriab-Fisher et al., Biochem. Pharmacal. 60:83-90, 2000), and proteins having a molecular mass up to 120 KDa (Schwartz, et al., Science, 285:1569-1572, 1999), 45 nm diameter magnetic beads (Lewin, et al. Nat. Biotechnol. 18:410414, 2000), and 200 nm diameter liposomes (Torchilin, et al., Proc. Nat. Acad. Sci. USA 98:8786-8791, 2001). Examples of MPP include but not limited to poly (Arg/Lys) peptides, Arg-rich peptides derived from HIV-TAT, Antennapedia, ETA, nuclear localization/export signals (NLS/NES) such as: HIV TAT$_{47-57}$: YGRKKRPQRRR (SEQ ID NO: 17); Drosophila Antennapedia (ANTp 16): RQIKIWFQNRRMKWKK (SEQ ID NO: 18); W/R: RRWRRWWRRWWRRWRR (SEQ ID NO: 19), AlkCWK$_{18}$: CWK$_{18}$ (SEQ ID NO: 20); Di-CWK$_{18}$: K$_{18}$WCCWK$_{18}$ (SEQ ID NO: 21); Transportan: WTLNSAGYLLGKINLKALAALAKKIL (SEQ ID NO: 22); DipaLytic: GLFEALEELWEAK (SEQ ID NO: 23); K$_{16}$RGD: K$_{16}$GGCRGDMFGCAK$_{16}$RGD (SEQ ID NO: 24); P1: K$_{16}$GGCMFGCGG (SEQ ID NO: 25); P2: K$_{16}$ICRRARGDNPDDRCT (SEQ ID NO: 26); P3: KKWKMRRQFWVKVQRbAK(B)bA (SEQ ID NO: 27); P3a:VAYISRGGVSTYYSDTVKGRFTRQKYNKRA (SEQ ID NO: 28); P9.3: IGRIDPANGKTKYAPKFQDKATRSNYYGNSPS (SEQ ID NO: 29); Pep-1: KETWWETWWTEWSQPKKKRKV (SEQ ID NO: 30); Plae: PLAEIDGIELTY (SEQ ID NO: 31); Kplae: K$_{16}$GGPLAEIDGIELGA (SEQ ID NO: 32); cKplae: K$_{16}$GGPLAEIDGIELCA (SEQ ID NO: 33); MGP: GALFLGFLGGAAGSTMGAWSQPKSKRKV (SEQ ID NO: 34); HA2: WEAK(LAKA)$_2$.LAKH(LAKA)$_2$LKAC (SEQ ID NO: 35); LARL$_6$: (LARL)$_6$NHCH$_3$ (SEQ ID NO: 36); Hel-11-7: KLLKLLLKLWLLKLLL (SEQ ID NO: 37); KK: (KKKK)$_2$GGC (SEQ ID NO: 38); KWK: (KWKK)$_2$GCC (SEQ ID NO: 39); RWR: (RWRR)$_2$GGC (SEQ ID NO: 40); SV40 NLS7: PKKKRKV (SEQ ID NO: 41); NLS12: PEVKKKRKPEYP (SEQ ID NO: 42); NLS12a: TPPKKKRKVEDP (SEQ ID NO: 43); SV40 NLS13: GGGGPKKKRKVGG (SEQ ID NO: 44); AV NLS13: GGGFSTSLRARKA (SEQ ID NO: 45); AV RME NLS17: CKKKKKKSEDEYPYVPN (SEQ ID NO: 46); AV FP NLS28: CKKKKKKSEDEYPYVPNFSTSLRARKA (SEQ ID NO: 47); SV40 N1 NLS24: LVRKKRKTEEESPLKDKDAKKSKQE (SEQ ID NO: 48); and Loligomer: K$_9$K$_2$K$_4$K$_8$GGK$_5$ (SEQ ID NO: 49). For reviews of MPP properties see (Futaki et al, J. Mol. Recognit. 16:260-

264, 2003; Fischer, et al., J. Biol. Chem., 279(13): 12625-12635, 2004; Wadia and Dowdy, Curr. Protein Pept. Sci. 4: 97-104, 2003; and Prochiantz, Curr. Opin. Cell. Biol. 12:400-406, 2000; Schwartz and Zhang, Curr. Opin. Mol. Therap. 2(2): 162-167, 2000).

PNA-PEG-conjugates PNA-PEG-R8, PNA-PEG-$D_{SH}$ and PNA-PEG-DSPE are prepared and tested for uptake into human cells, by being added directly to the cell culture medium. HeLa cells grown on cover slips are incubated with 5 µM of each PNA-PEG-conjugate in serum-free medium overnight, and are then fixed and examined by fluorescence microscopy. All three compounds, PNA-PEG-$D_{SH}$, PNA-PEG-R8 and PNA-PEG-DSPE were shown to be distributed within the cytoplasm but not in the nucleus. These results indicate that cellular uptake of conjugates containing MPP such as R8 may still involve the endocytotic pathway. These data are consistent with data showing involvement of endocytosis in the cellular internalization of cell-penetrating peptides and their conjugates to peptide nucleic acids (Richard et al., J. Biol. Chem., 278(1):585-590, 2003; Console, et al., J. Biol. Chem., 278(37): 35109-35114, 2003; and Drin, et al., J. Biol. Chem., 278(33): 31192-31201, 2003).

The targeting ligands for antiviral nuclease-derived compositions herein may further comprise cell surface receptor recognizing ligands (T-CSR) exhibiting high-binding affinity to host cell surface receptors (CSR) expressed by a particular virus host cell. T-CSR are exemplified by an 8-amino acid T-peptide (ASTTTNYT; SEQ ID NO: 1) and other short synthetic peptides derived from envelope protein gp120 of HIV-I and from other viral proteins, having partial amino acid sequence homology with the HIV gp120 fragment (residues 414-434), targeting primary host T-cells containing CD4 receptor (Chersi et. al., Viral. Immunol. 13(4):547-554, 2000; Pert, et al., Proc. Nat. Acad. Sci., USA 83:9254-9258, 1986). Another example of a virus specific T-CSR is a peptide containing positively-charged sequences of human papillomavirus type 16 capsid proteins. Such peptides synthesized to contain heparin and DNA-binding sequences can serve as transfection agents for drug delivery into the cytoplasm of target cells via the heparan sulfate receptor, and once inside the cell nucleus can act as nuclear localization factors (NLS) (Bousarghin, et al. J. Gen. Virol. 84:157-164, 2003).

Yet another example of a useful T-CSR for the conjugates herein is mannose-6-phopshate (M-6-P) targeting to cation-independent mannose-phosphate receptors (MPR). The two M-6-P receptors the 46 kDa cation-dependent MPR(CD-MPR) and the 300 kDa cation-independent M-6-P/insulin-like growth factor-II (IGF-II) receptor (CI-MPR) are integral membrane glycoproteins. The CI-MPR extracytoplasmic domain contains two distinct M-6-P-binding sites and a single IGF-II-binding site, whereas the CD-MPR contains a single M-6-P-binding site and does not bind IGF-II (Ghosh, et al., Nature 4:202-212, 2003). Both receptors are present on cell membrane as non-covalent dimmers allowing for high-affinity binding of ligands that are multivalent for M-6-P residues (Byrd, et al., J. Biol. Chem. 275:18638-18656, 2000). Herpes simplex virus (HSV) contains glycoprotein D (gD) modified with mannose-6-phosphate, which actively binds to both CI-MPR and CD-MPR. HSV uses distinct cell surface receptors in a sequential fashion to enter cells. The virus initially adsorbs onto heparan and chondroitin sulfate glycosaminoglycans GAGs, which are numerous components of cell membrane (Shieh, et al., J. Cell. Biol. 116:1273-1281, 1992; Leduc, et al, Abstract C-90 of the 18th Intern. Herpes Workshop, 1993) and then interacts with other receptors such as MPR which facilitate HSV entry into the cells (Brunetti, et al., J. Virol. 69 (6): 3517-3528, 1995). MPRs found on the cell surface almost exclusively in the clathrin-coated pits have been also shown to bind extracellular lysosomal enzymes as well as human DNase I and direct them to endosomes and lysosomes (Oliveri, et al., Eur. J. Immunol. 34:273-279, 2004; Ghosh, et al., Nature 4:202-212, 2003).

Yet another example of T-CSR is folic acid targeting folate receptor-α (FR-α), which has been identified as a significant co-factor for cellular entry of ssRNA Filoviruses such as Marburg (MBG) and Ebola (EBO; Chan, et al., Cell 106:117-126, 2001). Yet another example occurs in influenza virus infection, which is initiated by interactions between viral hemagglutinin protein and sialic acid containing cell receptors (Mochalova, et al. Virology 313 (2):473-480, 2003). Synthetic peptides containing sialic-acid binding sequences may serve as targeting ligands, directing an antiviral nuclease to virus host cells. Carbohydrate-protein specificity of interaction are at least equivalent to or exceed that of many other ligand binding systems. See for example, reviews of carbohydrate ligands for targeted delivery of therapeutics (Davis et al., Curr. Opin. Drug. Disc. & Dev. 5(2):279-288, 2002; Rihova, Adv. Drug Deliv. Rev. 29: 273-289, 1998; and Yamazaki, et al., Adv. Drug Deliv Rev. 43:225-244, 2000). Such interactions include both proteins and polypeptides (Opanasopit, et al. Am J. Physiol Gastrointest Liver Physiol 280:G879-G889, 2001), and non-natural polymers such as HPMA bearing other small molecules (Julyan, et al., J. Control Release 57:281-290, 1999).

The targeting ligands carried by polymeric carriers may also comprise one or more of various cell surface receptors (CSR) themselves with specific binding affinity to viral glycoproteins expressed on the membrane of infected cells such as T4 cell receptor CD4, co-receptors CCR5 and CXCR4, having affinity to HIV glycoprotein gp120 CSR, and which are expressed on HIV infected cell membranes and on others (EBO). Folate receptor-α (FR-α) can be used for targeting a cell infected with Marburg (MBG) or Ebola (EBO) virus.

There are relatively few clinically useful antiviral drugs, and a small number of viruses, which are susceptible to these drugs. The development of effective antiviral drugs directed at specific aspects of the viral replication cycle is seriously hampered by the rapid evolvement of resistant strains of viruses. The viral resistance not only results in the frequent failure of antiviral therapy, but also limits the effectiveness of subsequent therapies. Moreover, attempts to counter drug resistance lead to complex, expensive and toxic drug regimens. The problem of resistance to antiviral therapy is not limited to HIV, but has been seen in all viruses against which antiviral therapy has been developed such as herpes viruses, hepatitis viruses B and C, influenza viruses, etc.

In vitro resistance can be observed in all viruses against all existing therapeutic agents by a straightforward procedure well known to the skilled artisan of growing the virus in medium with progressively increasing concentrations of the respective antiviral agent. Viruses resistant to antiviral therapeutics have also been isolated from both treated and newly infected patients. Mechanisms of viral resistance include point mutations, recombination and gene amplification. Mutations in viral RNA genomes occur with higher frequency than mutations in genomes of DNA viruses because RNA polymerase, unlike DNA polymerase, does not have a proof reading mechanism. For example, the reverse transcriptase of HIV-I makes on average 1 error per 10 000 bases copied resulting in daily production in a single infected individual of about 10 billion single-point mutants of viral RNA. Additional genetic variations are is produced by the recombining of the genomes of viruses of different strains. This may occur when two viruses of different strains simultaneously infect the same cell and segments of their transcribed genes are recombined into the progeny virus genome.

High level resistance to a single drug may be conferred by a single mutation. For example, mono-therapy of HIV-I infected individuals with lamivudine or nevirapine results in development of high-grade resistance within about one month of treatment. In the case of some other antiviral drugs the resistance development is more complex requiring the accumulation of three or more mutations. This is the case of anti-HIV drugs such as zidovudine and some protease inhibitors, when mono-therapy with these agents produces resistance after 6 or more months. In some cases, a mutation conferring resistance to one drug may even re-sensitize the virus to another antiviral drug. For example, a mutation at RT position 184 of HIV-I RNA confers high grade resistance to lamivudine, but at the same time re-sensitizes the virus to zidovudine providing basis for the combination therapy of zidovudine and lamivudine. Early studies of HIV demonstrated that zidovudine-resistant HIV have reduced replicative capacity and therefore reduced transmissibility compared with the wild-type viral strain in the absence of the drug. Since then, transmission of drug-resistant HIV has been observed via the sexual vertical and parenteral routes. Drug-resistant mutant viruses have also been detected in individuals soon after HIV seroconversion.

One of the most distinct properties of antiviral preparations based on nucleases is the fact that the mutations changing the order of nucleotides within viral DNA or RNA that are responsible for viral resistance to the applied drug do not affect the antiviral activity of nucleases. The nucleases kill viruses by impairing the unprotected viral nucleic acids at the expense of the cleavage of phosphodiester bonds between the nucleotides of viral DNA and RNA molecules. The substitution of phosphodiester bonds with nuclease-resistant bonds in viral nucleic acids requires major changes in the nature of dozens of both viral and cellular enzymes responsible for the synthesis of the viral nucleic acids is an incredible phenomenon. Inclusion of antiviral nucleases into conventional mono-therapy regimen may preclude occurrence of drug-resistant mutants or significantly reduce chances for their survival and/or transmission while resulting in lower toxicity compared to combination therapy by two or three conventional antiviral drugs.

A method is provided for treating viral diseases in human and nonhuman animals, insects and plants, the method comprising administering virus-group-specific-nuclease-derived antiviral compositions in combination with conventional mono-therapy regimen, wherein the method completely eliminates occurrence of drug-resistant mutants or significantly reduce chances for their survival and/or transmission while resulting in lower toxicity compared to conventional combination therapy by two or three antiviral drugs.

Also provided is a method for preventing and treating viral diseases in human and nonhuman animals, insects and plants, the method comprising administering virus-group-specific "cocktails", the cocktail having a mix of nuclease-derived antiviral compositions of this invention, wherein each antiviral cocktail includes nucleases having hydrolytic activity towards one or more of various intermediate replicating forms of viral nucleic acids that appear during replication, i.e., the life cycle of the targeted virus.

In one embodiment the invention provides a method for prevention and treatment of viral diseases caused by Group I dsDNA viruses, Group II ssDNA viruses, by administering an antiviral nuclease selected from group of nucleases comprising Group I dsDNA-specific nucleases, Group II ssDNA-specific nucleases, Group IV ssRNA-specific nucleases, Group VI non-specific nucleases and Group VII artificial nucleases the Group being defined, according to the classification of nucleases described herein.

In another embodiment the invention provides a method for preventing and treating a viral disease caused by Group III dsRNA or Group IV ss(+)RNA viruses, the method involving administering an antiviral nuclease selected from the group of nucleases comprising Group II ssDNA-specific nucleases, Group III dsRNA-specific nucleases, Group IV ssRNA-specific nucleases, Group VI non-specific nucleases and Group VII artificial nucleases, the Groups as defined, according to the classification of nucleases described herein.

In yet another embodiment the invention provides a method for preventing and treating a viral disease caused by Group V ss(−)RNA viruses, by administering an antiviral nuclease selected from the group of nucleases comprising Group III dsRNA-specific nuclease, Group IV ssRNA-specific nucleases, Group VI non-specific nucleases and Group VII artificial nucleases according to the classification of nucleases described herein.

In another embodiment the invention provides a method for prevention and treating of viral diseases caused by Group VI ss(−)RNA RT viruses, by administering an antiviral nuclease selected from the group of nucleases comprising Group I dsDNA-specific nucleases, Group II ssDNA-specific nucleases, Group IV ssRNA-specific nucleases, Group V hybrid-specific nucleases, Group VI non-specific nucleases and Group VII artificial nucleases according to the classification of nucleases described herein.

In yet another embodiment the invention provides a method for preventing and treating a viral disease caused by Group VII dsDNA RT viruses by administering an antiviral nuclease selected from the group of nucleases comprising Group I dsDNA-specific nucleases, Group II ssDNA-specific nucleases, Group III dsRNA-specific nucleases, Group IV ssRNA-specific nucleases, Group V hybrid-specific nucleases, Group VI non-specific nucleases and Group VII artificial nucleases according to the classification of nucleases described herein.

The described antiviral compositions are administered parenterally (subcutaneously, intramuscularly, intravenously), as aerosols for inhalation, intranasally, as eye drops, locally for applying on cutaneous viral lesions, for example, per anus, per vagina. For oral administration, the antiviral conjugates of this example could be modified by methods known in the art (see for example, U.S. Pat. No. 5,698,515 to Pate, et al., Dec. 16, 1997; US Patent Application 2003/0087808 to Soltero, et al, May 8, 2003).

Pharmaceutical Compositions

The present invention in various embodiments provides pharmaceutical compositions comprising a therapeutically effective amount of an antiviral nuclease-containing composition as described herein. All of the pharmaceutical compositions described herein can be formulated with or without an agent or device for sustained release, for delivery locally or systemically. A pharmaceutically acceptable carrier or excipient can be added. Such a carrier includes but is not limited to saline, buffered saline, dextrose, water, glycerol, ethanol, and combinations thereof. The formulation should suit the mode of administration. An "effective amount" as the term is used herein is an amount of a therapeutic agent or combination of agents sufficient to achieve a recognized medical endpoint, in this case, remediation of a symptom of a viral infection. The effective amount can be determined empirically by a skilled artisan according to established methods of measurement of relevant parameters, as described herein.

The compositions herein can further comprise wetting or emulsifying agents, or pH buffering agents. The composition can be a liquid solution, suspension, emulsion, tablet, pill, capsule, sustained release formulation, or powder. The compositions can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Various delivery systems are known and can be used to administer a composition of the invention, e.g., encapsulation in liposomes, microparticles, microcapsules and the like.

In an exemplary embodiment, a composition herein is formulated in accordance with routine procedures as a pharmaceutical composition adapted, for example, for subcutaneous administration to human beings. Typically, compositions for subcutaneous administration are solutions in sterile isotonic aqueous buffer. Where necessary, the composition may also include a solubilizing agent and a local anesthetic to ameliorate pain at the site of the injection. Generally, the ingredients are provided either separately or mixed together in unit dosage form, for example, as a dry, lyophilized powder or water-free concentrate in a hermetically sealed container such as an ampoule or sachette, for example, indicating the quantity of active agent. Where the composition is to be administered by infusion, it can be dispensed with an infusion bottle containing sterile pharmaceutical grade water, buffer, or saline. Where the composition is administered by injection, an ampoule of sterile water or saline for injection can be provided so that the ingredients may be mixed prior to administration. The compositions herein can in various components thereof be formulated as suppositories, which contain active ingredient in the range of about 0.5% to about 10% by weight; oral formulations preferably contain about 10% to about 95% active ingredient by weight. A daily dose is administered as a single dose, or is divided into a plurality of smaller fractional doses, to be administered several times during the day.

As used herein, a dosing schedule refers to a protocol for administering any of the compositions comprising for instance one or more of an in vivo proteasome inhibitor composition as described herein, in an effective dose, administered simultaneously or within a particular interval of each other, for example, within one day of each other, or as a combined preparation, or separately, and includes the amount of the composition delivered per unit time such as per day, and the duration or period of time over which each composition is administered.

In one aspect, the invention provides a method for preventing or treating a viral infection, the method comprising administering to a subject in need thereof composition of at least one nuclease-containing composition as described herein, each in an amount sufficient to decrease the number of infective units in the subject; and determining the amount of virus-specific nucleic acid or infective units or a viral specific protein content, thereby treating or preventing the infection. Determining the amount of effective antiviral activity is measuring a parameter selected from the group of cell fluorescence of a cell in a biopsy or culture sample; fluorescence of a protein band on an SDS gel of a tissue or cell sample; antibody binding of a protein on a gel sample; or a viral-encoded protein function as is known to one skilled in the art of virology. Administering the composition described herein reduces viral load in the subject, compared to viral load assayed prior to administering the composition, for example, administering the composition reduces viral load by about 50%, or by about 70%, compared to that assayed prior to administering the composition.

The compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular virus will depend on the nature of the virus, and can be determined by standard clinical techniques. The precise dose to be employed in the formulation will also depend on the route of administration, and the seriousness of the disease or disorder, and should be decided according to the judgment of the practitioner and each patient's circumstances. Routine determinations of sample levels of a proteasome activity are determined by one of ordinary skill in the art. Effective doses may be extrapolated from dose-response curves derived from in vitro or animals or animal model test systems, by one of ordinary skill in the art of pharmacology. Dosages of the compositions to be administered to a subject are adjusted for known variations from species to species using standard data encompassing criteria for absorption, distribution, half-life kinetics in circulation, metabolism, excretion, and toxicology of the compositions of the embodiments herein. Suitable dosage ranges for administration are generally about 0.01 micrograms to about 10,000 micrograms of each active compound per kilogram body weight per day, for example, about 0.01 micrograms to about 1 microgram/kg, about 0.1 micrograms/kg to about 10 micrograms/kg, about 1 microgram/kg to about 500 micrograms/kg, or about 10 micrograms/kg to about 10 mg/kg of body weight per day. Suitable dosage ranges for administration are thus generally about 0.01 micrograms/kg body weight/day to about 10 mg/kg body weight/day.

The invention in other embodiments provides a pharmaceutical pack or kit comprising one or more containers filled with one or more of the ingredients of the pharmaceutical compositions of the invention. In such a pack, or kit can be found a container having a unit dosage of the nuclease composition. Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration. As a preferred dosage for administration is intravenous, the unit dosage can be prepackaged in an infusion bottle or bag.

Unless otherwise defined, all technical and scientific terms herein have the same meaning as commonly understood by one of ordinary skill in the art to which this invention pertains. Methods and materials similar or equivalent to those described herein can be used in the practice of the present invention. The invention in various embodiments now having been fully described, additional embodiments are exemplified by the following Examples and claims, which are not intended to be construed as further limiting. The contents of all cited references are hereby incorporated by reference in their entirety herein.

Example 1

Antiviral Composition Comprising Hetero-Bi-Functional Polymer Carrying Antiviral Nuclease, Targeting Oligomer and Membrane Permeating Peptide This Example describes preparation of antiviral compositions Nuc-$P^f_n$-$(T^b)_r$, b, k=1, 2, r=1 wherein N is a nuclease selected from one of the groups described herein in the Classification of Nucleases, with preferential hydrolytic activity towards genomic or intermediate nucleic acid of the targeted virus. The nuclease is exemplified by a recombinant bovine DNase (TURBO DNase®; TDNase) supplied by Ambion, Inc., Cat. No 2239) genetically modified to enhance its affinity for and hydrolytic activity towards viral dsDNA, although any other natural or artificial nuclease with preferential hydrolytic activity towards dsDNA can be applied.

The nuclease is covalently attached to one terminus of a hetero-tri-functional forked (f=2) hydrophilic polymer $P^f_n$ with a number of monomers n=1-2000, while two targeting ligands $T^1$ and $T^2$ are covalently attached to the branches of the fork.

The hydrophilic polymeric carrier $P^f_n$ protects the nuclease from proteolytic degradation by endogenous proteases while increasing the solubility and half-life as well as cellular and nuclear uptake of the antiviral conjugate. Hydrophilic polymers capable of carrying out these functions include: polyethylene glycol (PEG), and other polyalkylene oxides; poly(NH-2-(hydroxypropyl)glutamine (PHEG); poly(n-2-hydroxypropyl)methacrylamide (HPMA) and others.

The polymer may also contain hydrolyzable linkages to enable its hydrolytic degradation within the cell to facilitate the release of active compounds. Suitable hydrolyzable linkages include, for example, carboxylate and phosphate esters, acetals, imines, orthoesters, enol ethers, diketane acetals, ketals, anhydrides, etc. Formation of such linkages within the polymer may be conducted using routine organic synthesis techniques known to, those skilled in the art. The hydrophilic hetero-tri-functional polymer $P_n$ is exemplified by a forked 2×20 kDa $PEG_2$ having an aldehyde group at the "trunk" end and succinylamide (NHS) and maleimide (MAL) groups at the fork ends: CHO-$PEG_2$-(NHS; MAL). Alternatively, a more stable vinylsulfone (VS) can be used instead of MAL. The hetero-tri-functional-forked-2×20 kDa-(Butyraldehyde)-$PEG_2$-(N-hydroxy-succinimidyl-ester; maleimide): CHO-$PEG_2$-(NHS; MAL) can be obtained custom synthesized from SunBio (Orinda, Calif.).

$T^1$ is selected from the group of membrane penetrating peptides (MPP) including but not limited to basic peptides containing D- or L-arginine residues or arginine-rich peptides derived from HIV-$TAT_{43-49}$, and $Antennapedia_{43-48}$, transportan, penetratin, etc. to provide for high cellular uptake of the antiviral conjugate. The membrane penetrating peptide $T^1$ is exemplified by lysine-terminated poly-Arg nanopeptide Lys-Arg8 (K-R8).

$T^2$ is selected from the group of oligomers with sequence-specific binding affinity towards targeted viral nucleic acid including but not limited to PNA, LNA, phosphorothio, morpholino, polyamides and other nuclease-resistant oligomers capable of providing targeted hydrolytic digestion of viral nucleic acid at a location inside the infected cell.

The sequence-specific oligomer $T^2$ is exemplified by the cationic bis-PNA, complementary to vaccinia virus dsDNA designed to direct the nuclease-containing conjugate to the viral dsDNA for ultimate hydrolytic digestion. The vaccinia virus (VV), harboring genomic viral dsDNA, exemplifies targeted virus although any other virus could be inactivated by a composition of this example carrying an appropriate nuclease and oligomer having a nucleotide sequence complementary to a region of targeted viral nucleic acid. The complementary oligomer bis-PNA is modified with J-pseudocytosine using standard techniques (Synthesis, Properties and Potential Applications, Bioorganic & Medicinal Chemistry, 1996, 4, 5-23; Kuhn et al., Nucl. Acids Res. 26: 582-587, 1998), and is purified by reverse phase HPLC, and characterized by MALDI-TOF mass spectrometry (Egholm et al., Nucl. Acid Res. 23: 217-222, 1995). The Cys-terminated modified cationic bis-PNA: f-Cys-$JT_2J_2T_5$-(Lys-aha)$_2$-Lys-$T_5C_2T_2$C-$LysNH_2$ (SEQ ID NO: 50) wherein J is pseudocytosine, is designed to form stable complexes with a region of a TK gene of dsDNA of vaccinia virus. The bis-PNA contains for example a sequence complementary to the 10-mer of homopurine strand $GA_2G_2A_5$ (SEQ ID NO: 51), according to the published sequences of the vaccinia virus TK gene: (GenBank No. J02425; Hruby, et al., Proc. Natl. Acad. Sci. USA 80:3411-3415, 1983). In the first strand of the bis-PNA the cytosine denoted as C is substituted by pseudo-cytosine denoted as J, to enhance binding affinity of bis-PNA to dsDNA at physiological pH (Kuhn, et al., J. Mol. Biol. 286:1337-1345, 1999). The positively-charged flexible linker containing two Lysine-6-aminohexanoic acid conjugates denoted as (Lys-aha)$_2$ is introduced to provide an enhanced binding affinity of cationic bis-PNA to viral DNA at physiological concentrations of salts (Kuhn, et al., Nucleic Acids Res. 26:582-587, 1998). The N-terminus of cationic bis-PNA also contains a fluorophore and a cysteine amino acid residue denoted as f-Cys. To follow penetration of the complex into a virus-infected cell, a fluorophore Cy3 (Amersham Pharmacia #PA23001) is conjugated to the amino group of the cysteine. To attach the fluorophore, 5 µg Cys-bis-PNA is diluted in 0.1M sodium carbonate pH 9.0 to a volume 35 µl; 1 mg of Cy3 fluorophore is dissolved in 30 µl $H_2O$, and 15 µl of the fluorophore is added to the Cys-bis-PNA solution and the mixture is incubated overnight in the dark at room temperature.

During a first conjugation step the NHS-group of the CHO-PEG-(NHS; MAL) reacts with the ε-amino group of the lysine-terminated octa-arginine membrane penetrating peptide K-R8 at slightly basic pH, about for example pH 7.5, resulting information of CHO-PEG-(R8, VS). Then the free MAL-group selectively reacts with the SH-group of Cys-terminated bis-PNA at neutral pH. The butyraldehyde CHO-group of CHO-PEG-(R8, bis-PNA) is reacted with the N-terminal α-amino group of TDNase at acidic pH for example, about 5.0, to yield the resulting TDNase-PEG-(R8, bis-PNA) conjugate. The acidic pH promotes the reaction of the butyraldehyde and the N-terminal amino group. Butyraldehyde is chosen because it is more selective under mild acidic conditions than propionaldehyde, and more stable in basic media than acetaldehyde (U.S. Pat. No. 5,932,462, to Harris, et al. issued Aug. 3, 1999)

Thereafter, the resulting 75 kDa conjugate TDNase(31 kDa)-PEG(40 KDa)-R8(1.5 kDa)-bis-PNA(2.5 KDa) is separated and fractionated, and enzymatic activity and other specific properties can be assayed. The concentration of the nuclease in collected fractions is assessed by absorbance at 280 nm using an extinction coefficient of 1.34. Conjugates are further analyzed by electrophoresis on for example, 7.5% SDS-PAGE, and stained with Coomassie blue to determine purity.

The 75 kDa anti-vaccinia-virus conjugate is taken up by cells and is localized to the cytoplasm, where replication of vaccinia virus occurs. Diffusion into the nucleus is inhibited or decreased by the large hydrodynamic radius of the 75 kDa antiviral conjugate. Nuclease-polymer conjugates of greater total molecular weight and therefore greater hydrodynamic radius can be similarly prepared and are within the scope of equivalents of these compositions. Large polymer conjugates are useful with RNase-like nucleases since almost all RNA containing viruses with exception of influenza virus replicate inside the cytoplasm. In addition, polymer conjugates are useful with DNase-like nucleases to allow penetration of the antiviral compound into the cell nucleus. To further promote intranuclear accumulation of DNase-containing compounds, a nuclear localization factor (NLS) instead of or in addition to an MPP, as a targeting moiety is used in a multivalent construct as described herein.

Example 2

Antiviral Composition Comprising a Hetero-Bi-Functional Polymer Carrying Multiple Nucleolytic Di/Tri Peptides, a Targeting Oligomer and a Membrane Permeating Peptide This Example describes preparation of antiviral compositions of the formula $(Nuc^a)_q$-$P_n$-$(T^b)_r$, a,b,q,r=1-8, wherein multiple nucleases N and membrane permeating peptide T are covalently attached to a hetero-bi-functional polymeric carrier $P_n$, n=1-2000. The nuclease, as exemplified by a non-natural homolog of tri-peptide Ser-His-Asp containing terminal D-amino acids D-Ser-His-D-Asp, possesses nucleolytic activities towards DNA and RNA (Li et al., Bioorg. Medic. Chem. 8:2675-2680, 2000). The targeting oligomer of the composition, "T" is, for example, a 15-mer Peptide Nucleic Acid ($PNA_{15}$): Cys-3'-TCCCAGGCTCAGATC-5' (SEQ ID NO: 52), having a nucleotide sequence designed to specifically hybridize with a TAR (trans-activation-responsive) hairpin element in the nucleotide sequence of HIV-I viral ssRNA. The $PNA_{15}$ has been designed to further have a single Cys amino acid residue at the end of the sequence that corresponds to the 3'-terminus. The $PNA_{15}$ has been shown to block interaction of TAT protein with TAR and to halt viral replication in vitro (Mayhood, et al. Biochemistry 39:11532-11539, 2000; Kashik et al., J. Virology 76: 3881-3891, 2002). In the $P_n$, n is for example, 684, and the conjugate is a hetero-bi-functional 30 kDa 8-arm-PEG: VS-PEG-[$NH_2$]$_8$-VS.

Chemical bonding of the nucleolytic tri-peptide D-Ser-His-D-Asp (SHD in the one letter amino acid code) to the amine groups of the polymeric carrier is carried out to ensure that the peptide is bound in a known active orientation via a carboxyl group of the D-Asp residue. Since di-peptide Ser-His and tri-peptide Ser-His-Asp exhibit similar nucleolytic activities, coupling the C-terminus of the Asp residue of the tri-peptide to the carrier is not expected to affect nucleolytic activity. N-terminal t-Boc-protected tri-peptide containing two D-amino acids: t-Boc-D-Ser-His-D-Asp, can be obtained by custom synthesis from was custom synthesized by Invitrogen Corporation (Carlsbad, Calif.). Hetero-bi-functional 8-arm 30 kDa VS-PEG-[$NH_2$]$_8$ is custom synthesized by Nektar Therapeutics (Birmingham, Ala.). The ratio of biotinylated tri-peptide to amine groups of the polymeric carrier VS-PEG-[NH2]$_8$ is chosen as 5:1. The coupling reagent is EDAC (1-Ethyl-3-(3-dimethyl-aminopropyl)carbodiimide hydrochloride obtained from Uptima (uptima@interchim.com). EDAC is the activating agent for two carboxyl groups of the D-Asp residue, to form an amide bond with primary amines of 8-arm PEG-[$NH_2$]s.

The resulting conjugate $PNA_{15}$-PEG-[SHD]$_8$-R8 contains eight tri-peptides, SHD, having hydrolytic nuclease activity with genomic ssRNA, intermediate RNA-DNA hybrid and dsDNA as substrates, and contains two targeting ligands, Cys-terminated $PNA_{15}$ with high-binding affinity towards TAR element of HIV RNA inside the host cell, and contains the membrane penetrating peptide Cys-R8 to enhance cellular uptake of the antiviral conjugate. An SH-group of terminal Cys residues in both targeting ligands is used to form a hydrolytically stable bond with two terminal VS groups of bi-functional 8-arm-PEG. The hydrophilic polymers such as PEG protect an antiviral nuclease from proteolytic degradation by endogenous proteases while increasing cellular and nuclear uptake, solubility, and half-life of the antiviral conjugates.

Example 3

Preparation of Hetero-Bi-Functional Targeted "Arm Constructs" for Further Use in Multi-Armed Complexes Containing Antiviral Nucleases This Example describes synthesis of "arm-constructs" $(Nuc^a)_q$-$P_n$-R and $(T^b)_r$-$P_n$-$L_{(+)}$, wherein in $P_n$, the term n is an integer from 1 to about 2000, and the polymer $P_n$ is a linear or branched hetero-bi-functional PEG (bi-PEG), wherein R is a sequence-specific chemically-modified oligonucleotide $L_{(+)}$, which undergoes Watson-Crick hybridization and subsequent covalent bond formation with a complementary oligonucleotide $L_{(-)}$ on a multivalent molecular scaffold, to form a covalent multi-armed antiviral complex using $(Nuc^a)_q$-$P_n$-$L_{(+)}$ and $(T^b)_r$-$P_n$-$L_{(+)}$ arm-constructs and modified dendrimer D-$L_{(-)}$ as described below in Example 7.

In a related embodiment, R is a reactive conjugating moiety, examples of which include but are not limited to aldehyde (CHO), maleimide (MAL), vinylsulfone (VS), hydrazine (HZ), succinate (NHS), and carboxylic acid (COOH) groups, to form a covalent multi-armed antiviral complex using N-P(n)-R and $T^i$-P(n)-R constructs and chemically-modified dendrimer D as described below in Example 6.

In yet another embodiment R is a hydrophobic entity H, such that a non-covalent multi-armed antiviral complex using $(Nuc^a)_q$-$P_n$-H and $(T^b)_r$-$P_n$-H constructs and hydrophobic core dendrimer $G0(C_{12})$ is formed as described in Example 5. The term $(T^b)_r$, in which b and r can be from 1 to about 8, represents a targeting moiety such as a modified oligonucleotide complementary to a specific nucleotide sequence of a target viral nucleic acid. The targeting moiety T can be prepared from such analogs as modified PNA, or other sequence specific oligomers, cell membrane penetrating peptides (MPP) such as basic Arginine- and Lysine-rich peptides, nuclear transport or export signal peptides (NLS or NES), targeting ligands T-CSR with specific affinity to host cell surface receptors (CSR), oligo- and poly-saccharides, phospholipids, etc. The targeted bi-PEG conjugates described in this example comprise the following types of targeting ligands:

Modified sequence-specific oligonucleotides are prepared, each having a nucleotide sequence that is complementary to a region of a targeted viral nucleic acid. The hetero-bi-functional PEG conjugate has one terminal covalently attached to a sequence-specific oligomer that targets viral DNA and RNA, and antiviral dendrimers covalently attached to the second terminal of said polymer.

This example features bis-PNA complementary to the TK-gene of vaccinia virus. However, any of the following types of modified nucleotides can be used in the scope of this invention. These include peptide nucleic acids (PNA), Locked/Bridged Nucleic Acids (LNA/BNA) forming stable duplexes with viral ssDNA and ssRNA, cationic homopyrimidine bis-PNAs forming stable complexes with purine strands of viral dsDNA or dsRNA, novel PNA analogs such as hydroxyproline-PNA (HypNA), serine-PNA (SerNA) including their monomers, dimers and polymers disclosed in the (US patent application 2003/0059789 from Mar. 27, 2003 to Efimov et al.), sequence-specific hairpin polyamides targeting minor-groove of viral dsDNA, morpholino oligos targeting viral ssRNA (Summerton and Weller, Anti-sense & Nucleic Acid Drug Development 7:187-195, 1997), phosphorothioate (PS) oligos, pyrrolidine-amide oligonucleotide mimic (POM) with kinetically selective binding of ssRNA over ssDNA, zinc fingers with DNA or RNA specificity (Friesen et al., Nature Structural Biology Vol. 5, No 7:543-546, 1998), and other modified oligomers capable of forming stable sequence-specific complexes with the viral nucleic acids.

PNA molecules have 50 to 100-fold greater affinity for complementary RNA and DNA than do conventional oligonucleotides with the same number of bases (Nilesen et al., Science 254: 1497-1500, 1991; Hanvey et al., Science: 258: 1481-1485, 1992). Modified cationic bis-PNAs have even higher binding efficiency in regards to binding of double-stranded nucleic acids at physiological conditions via a formation of a strand displacement complex composed of an internal bis-PNA-DNA helix and a virtually single-stranded (non-complementary) DNA strand (Egholm, et al. Nucleic Acid Res. 23: 217-222, 1995; Griffith et al. J. Am. Chem. Soc. 117:831-832, 1995). A cationic bis-PNA targeted towards TK-gene of vaccinia virus is prepared as described below.

Hetero-bi-functional PEG conjugates with membrane penetrating peptides (MPP) for delivery of large proteins into the cytoplasm and across/into epithelial tissues are synthesized. This example features MPP compositions comprising poly(D-Arg) octamer R8, Antennapedia$_{43-48}$ (AP$_{43-48}$) and HIV TAT$_{49-57}$. However other basic peptides containing arginine residues or analogs, arginine-rich peptides and proteins such as transportan, penetratin and the like are within the scope of this invention.

Cysteine-terminated membrane permeating peptides C-R8 consisting of one L-Cysteine and nine D-Arginine residues, Antennapedia$_{43-48}$, and TAT$_{49-57}$ peptides are synthesized by automated peptide synthesizer ABI433 using standard solid-phase Fmoc chemistry as described (US patent application 2002/012719810 to Rothbard, et al.). Terminal SH-groups of Cys-terminated delivery-enhancing peptides R8, TAT$_{43-49}$ and Antennapedia$_{43-48}$ are covalently attached to MAL group of 5 kDa MAL-PEG-DSPE at a pH of 7.0. The cell membrane permeating rates of resulting three delivery-enhancing transporters R8-PEG-DSPE, TAT$_{43-49}$-PEG-DSPE and Antennapedia$_{43-48}$-PEG-DSPE are compared by cellular assays using Jurkat cells (human T-cells) and marine B cells (CH27) as described (US patent application 2002/012719810 to Rothbard, et al.) R8-PEG-DSPE is shown to enter cells approximately 50-fold faster than Antennapedia$_{43-48}$-PEG-DSPE, and about 100-fold faster than TAT$_{43-49}$-PEG-DSPE.

Nuclear localization signals are naturally occurring peptide sequences found in some native viral proteins, which mediate delivery of large proteins from the cytoplasm into the cell nucleus. Typical peptide sequences of NLS contain several basic amino acids. The NLS featured in this example is 7-amino acid peptide PKKKRKV (SEQ ID NO: 41), which is a monopartite NLS from SV40 large T antigen. However, numerous other functional NLS sequences can be used and are within the scope of this invention including 12-amino acid peptide PEVKKKRKPEYP (SEQ ID NO: 42; U.S. Pat. No. 6,312,956 to Lane, incorporated here by reference), 13-amino acid peptide GGGGPKKKRKVGG (SEQ ID NO: 44) of SV40 large T antigen (Lanford, Cell 37:801-813, 1984), 13-amino acid peptide GGGFSTSLRARKA (SEQ ID NO: 45) of adenoviral NLS, 17-amino acid peptide CKKKKKKSEDEYPYVPN (SEQ ID NO: 46) of adenoviral receptor mediated endocytosis (RME) protein, 28-amino acid peptide CKKKKKKKSEDEYPYVPNFSTSLRARKA (SEQ ID NO: 47) of adenoviral fiber protein (Tkachenko, et al., J. Am. Chem. Soc. 125: 4700-4701 (2003), 24-amino acid peptide LVRKKRKTEEESPLKDKDAKKSKQE (SEQ ID NO: 48) bipartite NLS from SV40 N1 protein (Dingwall et al., Trends Biochem. Sci. 16(12): 478-81 (1991), nucleoplasmin, polyoma virus large T, histones, c-myc (U.S. Pat. No. 5,115,096 to Shoyab et al., incorporated here by reference), and MAX (U.S. Pat. No. 5,115,096 to Brent et al., incorporated here by reference).

To attach NLS to R8-PEG-NHS, an extra lysine is added to the N-terminal end (Chan and White, Fmoc solid phase peptide synthesis: A Practical Approach, Oxford University Press, 2000). The two conjugates R8-PEG-NLS and R8-PEG-DSPE are synthesized as described in Examples 1 and 2, and are tested both for cellular and nuclear uptake after addition to the cell culture. Hela cells grown on cover slips are incubated with 5 µM of each conjugate in serum-free medium overnight, then fixed and examined by fluorescence microscopy. R8-PEG-DSPE is found to be distributed within the cytoplasm and is absent from the nucleus, while R8-PEG-NLS is accumulated primarily in the nucleus.

T-CSR targeting ligands exhibiting high-binding affinity to host cell surface receptors (CSR) are prepared. A peptide T (ASTTNYT; SEQ ID NO: 1) having a sequence derived from envelope protein gp120 of HIV-I is synthesized as a T-CSR to target HIV primary host cells containing CD4 receptor. Peptide T can be attached to bi-PEG via an additional lysine or cysteine residue at the C-terminus, providing the necessary reaction groups, NH$_2$— amino group, ε-amino or SH-thiol groups. Another example of a virus specific T-CSR are synthetic peptides derived from positively-charged sequences of human papillomavirus type 16 capsid proteins L1 and L2 exhibiting high binding affinity to heparan sulfate receptors such as HPV 31 L1 Cta: GYRARPKFKAGKR SEQ ID NO: 53; HPV 45 L1 Ctb: RPAKRVRIRSKK: (SEQ ID NO: 54); hpv-16 11 Cta: SSTSTTAKRKKRKL (SEQ ID NO: 55); HPV-16 L2 Ct: MLRKRRKRL (SEQ ID NO: 56) HPV-16 L2 Nt: MRHKRSAKRTKRA (SEQ ID NO: 57) and others (Bousarghin, et al. J. Gen. Virol. 84:157-164, 2003).

Another example of T-CSR within the scope of this invention includes folic acid or pteroyl glutamic acid, a vitamin consisting of a pteridine ring linked by a methylene bridge to a para-aminobenzoic acid moiety, which is joined through an amide linkage to a glutamic acid residue Folates are required for the survival and growth of eukaryotic cells, and cellular folate uptake is mediated by at least two independent transport mechanisms (Weitman et al., Cancer Res. 52:3396-3401, 1992; Ross et al., Cancer, 1994, 73(9), 2432-2443, 1994. Reduced folates are internalized via a carrier-mediated low affinity ($K_m$ values are in 1-10 LM range) anion-transport system that is found in nearly all cells. Folic acid and 5-methyl tetrahydrofolate can also enter cells via a high affinity ($K_d$ values in 10-100 µM range) membrane-bound folate-binding proteins that are anchored to the cell membrane via a glycosyl-phosphatidyl-inositol moiety. The acquisition of folate in many cells is mediated primarily through a folate receptor (FR-α), a widely expressed 38-39 KDa glycosyl-phosphatidyl-inositol (GPI)-linked folate binding protein (FBP) protein that binds to physiological amounts of folates with high affinity in nanomolar range (Antony, Annu Rev Nutr 16:501-521, 1996).

The folate receptor-alpha (FR-α) has been shown to be a significant co-factor for cellular entry by filoviruses such as Marburg (MGB) and Ebola (EBO) viruses, which cause lethal hemorrhagic fever (Chan et al., J. Virol. 74:4933-4937, 2000). MGB and EBO viruses not only readily infect cells expressing FR-α receptors, but the FR-α receptors expressed in infected cells also facilitate MBG and EBO viral glycoprotein (GP)-induced cell-to-cell fusion or syncytia formation. Moreover, FR-α, soluble FBP, has been shown to bind infected cells expressing MBG or EBO GP on their membranes, while folic acid as well as bovine FBP have been able to inhibit entry by filovoruses in cells expressing FR-α (Chan, et al., Cell 106:117-126, 2001). The cellular uptake of exogenous molecules can be enhanced by conjugation of such molecules to folate (US Patent Application to Wedeking, et al., 2001; U.S. Pat. No. 6,280,991 to Raines, 2001).

Another useful T-CSR for the conjugates herein is mannose-6-phopshate (M-6-P) residues targeting to cation-independent mannose-phosphate receptors (MPR). The two M-6-P receptors cation-dependent CD-MPR and cation-independent CI-MPR present on cell membrane as non-covalent dimers allow for high-affinity binding of ligands that are multivalent for M-6-P residues (Byrd, et al., J. Biol. Chem. 275:18638-18656, 2000). Another example of T-CSR for the conjugates herein is mannose targeting to mannose-receptors expressed in macrophages, subsets of endothelial cells, smooth muscle cells, retinal pigment epithelium, kidney mesangial cells, myeloid cells, Kaposi sarcoma cells, etc. (reviewed in Stahl & Ezekovitz, Curr Opin Immunol. 10:50-55, 1998). Man-PEI-PEG and (M-6-P)-PEI-PEG conjugates are synthesized by a method similar to that described for mannose-polylysine conjugate (Erbacher, et al., Hum. Gene Ther 7:721-729, 1996), and mannose-PEI conjugate (Diebold, et al. J. Biol Chem 274(27):19087-19094, 1999). Synthesis of hetero-bi-functional diblock PEI-PEG-MAL copolymer having branched PEI terminated by $NH_2$-PEG-MAL has been carried out via macrostopper route as described in Petersen et al., J. Am. Chem. Soc., 277(44): 41613-41623, 2002). The conjugate has mannose or mannose-6-phosphate linked to free amino groups of the hetero-bi-functional copolymer branched PEI-PEG-MAL via a phenylisothiocyanate bridge (itc) using mannopyranosyl-phenyl isothiocyanate as coupling agent (Sigma), to obtain Man-itc-PEG or (Man-6-P)-its-PEG. Hetero-bi-functional branched $(NH_2)_k$-PEG-MAL, k is an integer of 8, with single terminal maleimide (MAL) or vinylsulfone (VS) group and multiple terminal free amino groups $NH_2$ can be obtained from Nektar Therapeutics, Inc. Coupling is performed by reacting 25 mg of $(NH_2)_8$PEG-MAL dissolved in 0.33 ml of water with 25 mg of mannopyranosylphenyl dissolved in 0.2 ml of dimethyl sulfoxide for 24 hours, followed by dilution with 4 ml of water and adjustment to 0.5 M sodium chloride, application of the sample to caption exchange chromatography (Bio-Rad Macroprep High S, salt gradient from 0.5 to 3 M NaCl) and dialysis against 150 mM NaCl. Conjugates are analyzed for content of PEG by using the ninhydrin assay (Cotton, et al., Current protocols in Human Genetics, pp. 12.3.1-12.3.33, John Wiley and Sons, N Y, 1996), and the content of mannose is assayed by using the resorcinol sulfuric acid method (Diesla, et al., Anal. Biochem. 175: 525-530, 1988).

Cell surface receptors (CSR) designed to target ligands that are conjugated to carried by polymeric carriers may also comprise various cell surface receptors (CSR) themselves with specific binding affinity to viral glycoproteins expressed on the membrane of infected cells, such as T4 cell receptor CD4, co-receptors CCR5 and CXCR4 with affinity to HIV glycoprotein gp120/CSX expressed on the membranes of HIV infected cells and many other host cell receptors. Other examples of CSRs include peptide derivatives of folate receptor-α (FR-α) capable of targeting a cell infected with a Marburg (MBG) or an Ebola (EBO) virus, and some peptide derivatives of CI-MPR with high affinity to viral glycoproteins.

The bi-PEG conjugates with covalently attached targeting moieties $(T^b)_r$, are used to direct multivalent complexes containing one or more antiviral nuclease to virus infected cells.

Example 4

Preparation of Covalent Conjugates of Antiviral Nuclease and Targeting Ligands with Hetero-Bi-Functional Polymers Carrying a Hydrophobic Moiety The Example describes preparation of compositions Nuc-$P_n$-H and $(T^b)_n$-$P_n$-H, wherein Nuc is an antiviral nuclease, $T^b$ are targeting ligands described in Example 3, wherein $P_n$ is a hetero-bi-functional hydrophilic polymer, and H is a hydrophobic moiety associated with a hydrophobic core dendrimer D as described in Example 5. Antiviral activity of nucleases is enhanced by conjugation with polymers that act to protect antiviral nuclease from proteolytic degradation by endogenous proteases, and to increase solubility, cellular uptake and half-life. A number of hydrophilic polymers are capable of carrying out these functions, including polyethylene glycol(PEG) and other polyalkylene oxides, poly(NH-2-(hydroxypropyl)glutamine (PHEG), poly(n-2-hydroxypropyl)methacrylamide (HPMA), and others.

The polymer may contain hydrolyzable linkages to enable hydrolytic degradation within the cell to facilitate release of an active compound. Suitable hydrolyzable linkages include, for example, carboxylate and phosphate esters, acetals, imines, orthoesters, amines, enol ethers, diketane acetals, ketals, anhydrides, etc. Formation of such linkages within the polymer may be conducted using routine organic synthesis techniques known to those skilled in the art. Although this Example describes preparation of the covalent constructs of a nuclease with hetero-bi-functional PEG, the same method is applied for preparation of covalent conjugates of bi-PEG with specially modified sequence-specific oligomers targeting viral nucleic acid, membrane permeating peptides and other targeting moieties.

Nuclease exemplified by wild-type bovine pancreatic RNase A is obtained for Ambion, Austin, Tex. RNase preferentially degrades single-stranded viral RNA. Other nucleases that could be conjugated with polymers in a similar manner include wild-type, recombinant, or chemically modified nucleases of human, animal, bacterial, plant or artificial origin. The selected polymer is a two-arm branched 2×10 kDa hetero-bi-functional PEG with 1,2-dipalmitoyl-sn-glycero 3-phosphatidyl ethanolamine (DSPE) on one arm, and propionylaldehyde's CHO-group on another arm, the resulting polymer abbreviated as DSPE-PEG-CHO, obtained from Nektar Corp. Among the different fatty acid types the lauryl, myristoyl, palmitoyl, stearoyl, oleoyl, and lineoyl analogs of DSPE can be also used.

The CHO reagent reacts with the N-terminal amino group of Lys(K) 1 of RNase A at an acidic pH of 5.0-6.0. The reaction is carried out at pH 5.0 at a 1:1 ratio of the DSPE-PEG-CHO reagent to RNase A. These conditions are optimal for obtaining the recovery of the protein with a single PEG per protein, rather than higher molecular weight adducts. The unmodified protein can be recycled. Conjugates are fractionated and fractions are assayed for enzymatic activity and other properties. The concentration of the final product is assessed by near-UV absorbance using an extinction coefficient of 1.34. Conjugates are also analyzed by electrophoresis on a 7.5% SDS-PAGE and stained with Coomassie blue to determine purity. The $T^i$-P(n)-H conjugates are obtained in a similar manner. Both N-P(n)-H and $T^i$-P(n)-H conjugates are used in non-covalent complexes with extended hydrophobic core dendrimers described below in Example 5.

Example 5

Antiviral Composition Comprising Multiple Hetero-Bi-Functional Constructs Non-Covalently Associated with a Multivalent Hydrophobic "Core" Dendrimer The Example describes preparation of multi-armed/multivalent antiviral complexes $[(Nuc^a)_q\text{-}P^f\text{-}H]_i\text{-}D\text{-}[H\text{-}P^f_m\text{-}(T^b)_r]_k$, wherein i and k are integers from 1 to 8. The complexes are formed through a non-covalent association of the "arm constructs" Nuc-$P_n$-H and T-$P_n$-H with a "core" multivalent molecular scaffold D. The "arm constructs" comprise hetero-bi-functional hydrophilic polymers $P^f_n$ and $P^f_m$ represented by PEG as described in Example 1, wherein n and m are integers from 1 to 2000, with one terminal of the polymers $P^f_n$ and $P^f_m$ being covalently attached to either a nuclease Nuc or to a targeting ligand T such as PNA, MPP, NLS, T-CSR or CSR described in Example 4, while the other polymer terminal is covalently attached to a hydrophobic "connective" moiety H exemplified by phospholipids such as dipalmitoyl-sn-glycero 3-phosphatidyl ethanolamine (DSPE), with lauryl, myristoyl, palmitoyl, stearoyl, oleoyl, and lineoyl analogs of DSPE containing "sticky" hydrophobic fatty acids. The presence of a hydrophobic moiety H mediates formation of multi-armed/multivalent antiviral compositions, where each arm construct Nuc-$P_n$-H or T-$P_n$-H is associated through a hydrophobic interaction with a hydrophobic molecular scaffold D represented in this example by an extended hydrophobic core PAMAM dendrimer $G_0(C_{12})$ (Watkins, et al., Langmuir 13: 3136-3141, 1997).

The "arm constructs" containing hydrophobic group H are amphiphilic since they are composed of two parts which differ substantially with respect to solubility in water: the hydrophilic parts A-PEG represent the polar "heads" while the hydrophobic "tails" (DSPE) are formed by non-polar chains of fatty acids that are lipophiles. Amphiphilic conjugates may differ significantly in the relative contribution by mass of the hydrophilic A-PEG and hydrophobic DSPE portions of the conjugate. A parameter identified as hydrophile-lipophile balance (HLB) provides a convenient means to rank these contributions in terms of their surfactant action (Adamson, Physical Chemistry of Surfaces: 505-507, 1976, 3rd Ed., John Wiley and Sons, New York).

The amphiphilicity of various conjugates may affect their immunogenic properties. The HLB of the amphiphilic compounds can affect immunological response of a subject that has been administered the compound. Amphiphilic conjugates with high HBL>20 have been shown to elicit a very low immunologic response (Waltrous-Peltier, et al. Pharm. Res. 9: 1177-1183, 1992), while conjugates with a low HBL<2 cause the accumulation of inflammatory cells, most notably macrophages (Hunter, et al. AIDS Res. Hum. Retrovir. 10, S95-S98, 1994). In aqueous solution the non-polar alkyl groups of DSPE molecules stick together (Finney, "Hydration Processes in Biology", ed. M. C. Bellissent-Funel, IOS Press, 115-124, 1999).

Conjugation with hydrophilic polymers $P_n$ as described in Example 3 results in protecting antiviral nuclease from proteolytic degradation by endogenous proteases, and increasing its solubility, cellular uptake and half-life. The amphiphilic nature of $(Nuc^a)_q\text{-}P^f_n\text{-}H$ and $H\text{-}P^f_m\text{-}(T^b)_r$ constructs also modulates penetration of the antiviral composition through cell membrane and provides additional protection against proteases. The nuclease is exemplified by the bovine pancreatic RNase A with preferential hydrolytic activity towards single-stranded viral RNA, although any wild-type, recombinant or chemically modified nuclease of human, animal, bacterial, plant or artificial origin could be conjugated with polymers in a similar manner. The preferred polymer is a hetero-bi-functional PEG with 1,2-dipalmitoyl-sn-glycero 3-phosphatidyl ethanolamine (DSPE) on one arm, and propionylaldehyde CHO-group, MAL-group or NHS-group on another arm, further abbreviated as DSPE-PEG-CHO, DSPE-PEG-MAL, DSPE-PEG-NHS supplied by Nektar Corporation, Inc. The CHO group selectively reacts with the N-terminal of the nuclease-cell targeting peptide at acidic pH; the NHS group reacts with ε-amino group of lysine of K-R8; and MAL reacts with the SH-group of PNA or cell targeting ligand (T-CSF) at neutral or slightly-basic pH as described in Example 1.

A mixture of a plurality of $(Nuc^a)_q$-PEG-DSPE and $(T^b)_r$-PEG-DSPE constructs with active moieties such as a nuclease $Nuc^a$ or a targeting ligand $T^b$, wherein q and r are integers from about 1 to about 8, is simultaneously introduced into aqueous solution with the DSPE "tails" to form hydrophobic associations with the hydrophobic core dendrimer. The result is a mixture of multivalent arm-core constructs with a random distribution of composition as well as a random quantity of heads groups. This example describes a sequential attachment procedure, which involves solid phase matrix and results in a multivalent composition comprising four different active moieties: a single nuclease-bovine DNase I, and 3 targeting ligands-PNA, R8 and folic acid (FA) in hydrophobic association with D represented by an extended hydrophobic core poly(amidoamine) dendrimer $G_0(C_{12})$ (Watkins et al., Langmuir 13:3136-3141, 1997). The 656 Da dendrimer $G_0(C_{12})$ containing four active surface groups $NH_2$ and 12 $CH_2$ groups comprising the internal methylene-based hydrophobic core is obtained from Dendritech, Inc. (Midland, Mich.).

The 5 kDa DSPE-PEG-CHO and DSPE-PEG-NHS conjugates are each covalently attached to an A active moiety, resulting in $(Nuc^a)_q$-PEG-DSPE and $(T^b)_r$ PEG-DSPE conjugates, wherein $Nuc^1$ is DNase I or other nuclease, $T^1$ is K-PNA, $T^2$ is K-R8, and $T^3$ is K-folic acid (FA). The NHS terminal of DSPE-PEG-NHS reacts with terminal lysine residues of lysine modified active moieties. The $G_0(C_{12})$ hydrophobic core dendrimer is then covalently bound via 2 kDa PEG linker to a solid phase "seed" matrix comprising chemically inert PEG-based hydrophilic resin (Grøtli, et al., J. Combin. Chem. 2000, 108-119, 2000; Buchardt and Meldal, Chemically Inert Hydrophilic Resin for Solid Phase Organic Synthesis. Tetrahedron Lett. 39: 8695-8698, 1998). Thereafter, $A''$-PEG-DSPE conjugates are added to allow non-covalent association of hydrophobic DSPE "tails" with the hydrophobic core of the G0(C12) dendrimer, which is covalently bound to the hydrophilic solid phase matrix. Each of the $(Nuc^a)_q$-PEG-DSPE and $(T^b)_r$-PEG-DSPE conjugates is introduced at the concentration ratio of 1:1 relative to the concentration of immobilized dendrimers. When one of the conjugates is hydrophobically attached in the average amount of one per each immobilized dendrimer, the conjugates remaining unbound are washed out. The procedure is repeated to sequentially attach by hydrophobic interactions conjugates of different or similar function. Finally the covalent link between "seed" dendrimers and the PEG-based matrix is cleaved by a standard technique. The technique described above is recommended for use when the amount of active moieties attached to a hydrophobic core dendrimer does not exceed 4-6, otherwise the reaction times may become prohibitively long.

Example 6

Antiviral Composition Comprising Multiple Hetero-Bi-Functional Constructs Covalently Associated with the Multivalent Dendrimer The Example describes multiple constructs $(Nuc^a)_q$-PEG-R and $(T^b)_r$-PEG-R, wherein a=2, q=1, r=1 and b is an integer of about 3 covalently attached to chemically modified dendrimer $D_{SH}$, wherein $Nuc^1$ is recombinant human DNase I, $Nuc^2$ is either synthetic S-peptide (Sp) or recombinant S-protein (21-124) derivative of human RNase I (SP), $T^1$ is bis-PNA targeted to the REV-gene of HIV-I, $T^2$ is an R8 membrane penetrating peptide, and $T^3$ is a T-CSR described in Example 3 such as Man-6-P, wherein R is a vinylsulfone group (VS), and dendrimer $D_{SH}$ is G-2 PAMAM dendrimer chemically modified to contain reactive terminal SH-groups. The Sp-DNase-PEG-VS, SP-PEG-VS, bis-PNA-PEG-VS and R8-PEG-VS constructs are prepared as described in Examples 1-3. To obtain thiol-modified $D_{SH}$ the $NH_2$-terminated PAMAM G-2 dendrimer was treated with nitrogen-purged 5 mM iminothiolane HCl, and 1 mM EDTA in PBS to convert the dendrimer surface amines to sulfhydryls. After incubation for 60 minutes with constant nitrogen purging, the reaction mixture is dialysed against PBS.

The SH-modified dendrimer $D_{SH}$ is then immobilized via a 2 kDa PEG linker to a solid phase "seed" matrix comprising chemically inert PEG-based hydrophilic resin as described in Example 4. The $(Nuc^1, T^b)$-PEG-VS conjugates are added sequentially one after another to allow for covalent association of a VS group with an SH-terminal group of the dendrimer immobilized on the hydrophilic solid phase matrix. Each of the $(Nuc^a, T^b)$-PEG-VS conjugates is introduced at a concentration ratio of 1:1 relative to the concentration of immobilized dendrimers. When one of the $(Nuc^a, T^b)$-PEG-VS conjugates is covalently attached in the average amount of one per each immobilized dendrimer, the unbound conjugates are washed out. The procedure is repeated to covalently attach all three conjugates in sequential manner. Finally, the covalent link between the immobilized dendrimers and PEG-based matrix is cleaved by a standard technique. The technique described above is recommended for use when the amount of active moieties to be attached to a dendrimer does not exceed about 4 or 5, otherwise the reaction times may become prohibitively long.

In addition to PAMAM dendrimers supplied by Dow Chemical and Dendritech, Inc. other antiviral dendrimers that are within the scope of and are useful for this invention or its equivalent include polyamidoamine or polylysine dendrimers bonded with sulfonic acid-containing or trimethylammonium-containing moieties (U.S. Pat. No. 6,190,650 to Matthews and Holan, 2003); poly(Lysine) Starburst™ dendrimers by Starpharma Ltd. such as SPL-2999 with the chemical formula BHAlys15lys16 (NHC-SNHNaphth-3,6-diSO3Na)32 (BHA: benzhydrylamine) and molecular weight of 16,615 Da shown to be active against herpes simplex virus HSV (Gong et al, Antiviral Research 55:319-329, 2002), SPL-7013 shown to be active against HIV; and dendrimer-like star polymers (Trollsas et al., Polymer Preprints 41(1): 258-259, 2000) and others. The PAMAM, PAMAM(EDA) and poly(Lysine) dendrimers have demonstrated activities in vitro against a variety of viruses, including herpes simplex virus (Bourne, et al., Antimicrobial Agents and Chemotherapy, 44(9): 2471-2474, 2000), influenza virus, measles virus, respiratory syncytial virus (RSV; Barnard, et al, Antivir. Res. 34:A88, 1997), human immunodeficiency virus (HIV; Witrouw, et al., Antiviral Research 41: A25, 1999), etc. The antiviral compositions of this example comprising S-peptide: Sp-DNase-PEG-D-PEG-$(T^b)$, and S-protein: SP-PEG-D-PEG-$(T^b)_r$ may form a noncovalent complex possessing both RNase and DNase nucleolytic activities: $(T^b)_r$-PEG-D-PEG-(RNase S)-DNase-PEG-D-PEG-$(T^b)_r$, which makes them attractive for targeting both genomic ssRNA and intermediate dsDNA of HIV, genomic dsDNA and intermediate ssRNA of HBV, and some other RT dependent viruses.

Example 7

Preparation of "Core" Dendrimer Carrying Multiple Oligonucleotides

The Example describes preparation of chemically modified "core" dendrimer containing multiple sequence-specific oligonucleotides $L_{(-)}$. Such $L_{(-)}$-modified dendrimers are further used for Watson-Crick hybridization and subsequent covalent bond formation with either multiple $(Nuc^a, T^b)$-$P_n$-$L_{(+)}$, k=1-8 linear constructs or with mono-functional "shell" dendrimers $(Nuc^a, T^b)$-$P_n$-$D_s$-$L_{(+)}$ each bearing oligonucleotide $L_{(+)}$ complementary to one of the $L_{(-)}$ oligonucleotides of said "core" dendrimer.

A 0.1 M aqueous solution of G-4 PAMAM dendrimers obtained from Dendritech, Inc. (Midland, Mich.) was treated with nitrogen-purged 5 mM 2-iminothiolane HCl (MW=138 Da) or Traut's Reagent (TR) obtained from Pierce (Rockford Ill.), and 1 mM EDTA in PBS at pH=8.0 to introduce sulfhydryl groups at dendrimer amine terminals. Alternatively, SPDP (MW=312 Da; N-succinimidyl 3-[2-pyridyldithio]propionate) can be used for the same purpose (US Patent application 2002/0187198 to Lee) resulting in an SH-modified "core" dendrimer $D_{SH}=D_c$-NH—C—$(CH_2)_3$—SH. The dendrimer $D_{SH}$ is immobilized via 2 kDa PEG linker to a solid phase "seed" matrix comprising chemically inert PEG-based hydrophilic resin as described in Example 4. The $L_{(-)}$-PEG-VS conjugates are added sequentially one after another to allow for covalent association of the VS group with the SH-terminal group of the dendrimer immobilized on the hydrophilic solid phase matrix. Each of the $L_{(-)}$-PEG-VS conjugates is introduced at the concentration ratio of 1:1 relative to the concentration of immobilized dendrimers. When one of the $L_{(-)}$-PEG-VS conjugates is covalently attached in an average amount of one per each immobilized dendrimer, the unbound conjugates are washed out. The procedure is repeated to covalently attach all three conjugates in a sequential manner.

Finally, the covalent link between the immobilized dendrimers and PEG-based matrix is cleaved by a standard technique.

Example 8

Preparation of Mono-Functional Multi-Arm "Shell" Dendrimers

Preparation of mono-functional multi-arm "shell" dendrimers was carried out by attachment of multiple mono-functional $(Nuc^a)_q$-PEG-$L_{(+)}$ or $(T^b)_r$-PEG-$L_{(+)}$ arm constructs to PAMAM G-2 dendrimer. Each of the attached arm constructs bears sequence-specific oligonucleotide $L_{(+)}$ represented by Locked Nucleic Acid oligonucleotide $LNA_{(+)}$ complementary to one of the multiple sequence-specific oligonucleotide $LNA_{(-)}$ covalently attached to the G-2 dendrimer. The G-2 PAMAM dendrimers obtained from Dendritech, Inc. (Midland, Mich.) were modified to contain terminal $L^a_{(-)}$ and $L^x_{(+)}$ oligonucleotide as described in Example 7. Each mono-functional G-2 "shell" dendrimer $D_s$ bears at least one $L^x_{(+)}$, which is complementary to one of the multiple $L^x_{(-)}$ oligonucleotides covalently attached to the G-3 "core" dendrimer as described in Example 7. Then multiple $(Nuc^a)_q$-PEG-$L^a_{(+)}$ and $(T^b)_r$-PEG-$L^b_{(+)}$ constructs undergo Watson-Crick hybridization with the corresponding complementary $L^{a,b}_{(-)}$ resulting in mono-functional $[(Nuc^a)_q$-PEG-$L^a_{(+)}$-$L_{(-)}]_z$-$D_s$-$L^x_{(+)}$.

Five types of mono-functional "shell" G2-dendrimers were synthesized: $[(N^a)_q$-PEG-$L^a_{(-)}]_4$-$L^a_{(+)}$-$D_s$-$L^x_{(+)}$, a=1, q=8, and $[(T^b)_r$-PEG-$L^b_{(+)}]_4$-$L^b_{(-)}$-$D_s$-$L^x_{(+)}$, b=1-4 each bearing a unique $L^x_{(+)}$, x=1-5 are synthesized: 1) the "nucleolytic" dendrimer $[(SHD)_g$-PEG$)]_4$-$D^1$-$LNA_{(3'-5')}$ carrying 4 "polymeric arms" each carrying 8 nucleolytic tri-peptides Ser-His-Asp; 2) the viral nucleic acid targeting dendrimer $(PNA$-$PEG)_4$-$D_s$-$L_{(3'-5')}$ carrying 4 "polymeric arms" each carrying a PNA complementary to a nucleotide sequence of the targeted viral nucleic acid; 3) the membrane permeating dendrimer $(R8)_4$-$D^4$-$LNA_{(3'-5')}$ carrying 4 "polymeric arms" each carrying a single membrane permeating peptide R8; 4) the nuclear localization dendrimer carrying 8 "polymeric arms" each carrying a nuclear localization signal (NLS); and 5) the host cell targeting dendrimer $(T$-$CSR)_4$-$D^5$-$LNA_{(3'-5')}$ carrying 4 "polymeric arms" each carrying a single mannose-6-phosphate residue.

In the preferred embodiment described in the Example 5 each mono-functional "shell" dendrimer is equipped with its own unique $LNA_{(3'-5')}$ which is complementary to one of the multiple $LNA_{(5'-3')}{}^k$, attached to the "core" G-3 dendrimer, wherein K is an integer from one to about 5. The complementary pair $LNA_{(3'-5')}$ and $LNA_{(5'-3')}$ undergo Watson-Crick hybridization, and covalent bond formation occurs when the "dormant" group attached to $LNA_{(5'-3')}$ is activated as described in the next Example 9.

Example 9

Subsequent Covalent Attachment of Two Complementary Oligomers after their Hybridization The Example describes a method for covalent attachment of two complementary oligo- or polynucleotides or oligo-like or polynucleotide-like molecules following Watson-Crick hybridization, to provide a covalent association between multiple multi-armed "shell" dendrimers carrying active antiviral moieties and a "core" dendrimer. Each dendrimer is equipped with one or more chemically modified oligomers comprising LNA (Locked Nucleic Acid), BNA (Bridged Nucleic Acid), PNA (Peptide Nucleic Acid), etc. which are complementary to one of the multiple oligomers covalently attached to the core dendrimer. The complementary oligomers at the core dendrimer are chemically modified with a poly-functional reagent to allow for covalent bond formation between two complementary oligomers subsequent to hybridization.

The polyfunctional reagent includes two or more highly reactive chemical groups, one of which remains inactive or dormant until activated, others of which groups are permanently active. The active groups are used to bind the reagent to the complementary oligomers attached to the core dendrimer. After Watson-Crick hybridization between the core and complementary shell oligomer takes place, the dormant reactive group on the core oligomer is activated, resulting in a covalent between the two complementary oligomers. In this Example a polyfunctional reagent N,N,N'-tri-(β-chloroethyl)-N-(p-formylphenyl) propylene diamine-1,3 (TFP) is used to illustrate the proposed technique. Two highly reactive aliphatic (β-chloroethyl)amino groups are used to attach the reagent to one of the complementary oligomers of the core dendrimer. The reactivity of the third dormant or potentially active aromatic (β-chloroethyl)amino group is strongly inhibited by the neighboring formyl residue. After hybridization between the modified core oligomer and its complementary shell oligomer takes place, the dormant reactive group on the core oligomer is activated by the reduction with sodium borohydride resulting in a covalent bridge between complementary core and shell oligomers.

Attachment of the polyfunctional reagent to the core oligomer using two aliphatic groups is carried out in 50% methanol/5 mM Tris-HCl, pH 7.5, at room temperature for 10-15 min. The reaction mixture contains 0.8 mM TFP and 50-100 μg of oligo/polynucleotide per ml. The modified oligo/polynucleotide is precipitated with ethanol (2 h at 20° C.) and is centrifuged; the pellet is dissolved in 10 mM Tris-HCl (pH 7.5). To remove unbound reagent, the oligo/polynucleotide solution from the reaction is applied to an equilibrated Sepharose G-50 column and eluted is with 10 mM Tris-HCl (pH 7.5). To estimate the percentage of the modified nucleotides in TFP-treated oligo/polynucleotide, the latter is sample hydrolyzed (1 M NaOH, 18 h, 37° C.), and the modified and non-modified nucleotides are analyzed by paper chromatography. Both the modified and unmodified complementary oligomers are then covalently attached to their respective core and shell dendrimers as described in Example 5. After hybridization of modified core oligomer and unmodified complementary shell oligomer the dormant chlorethyl group is activated by addition of sodium borohydride to the solution to a final concentration of 10 mM, and the mixture is incubated for 4 h at 40° C. The covalently bound shell-core dendrimer complexes obtained by this procedure are used as a multivalent platform for delivery of antiviral nucleases and ligands of this invention.

Example 10

Preparation of Core and Shell Dendrimers Carrying Self-Complementary Modified LNA to Form Multivalent Core-Shell Covalent Complexes The Example describes a covalent complex between multiple shell dendrimers $D_s$, and a single core dendrimer $D_c$ modified to include complementary oligonucleotides at each of their terminal groups.

Each shell dendrimer caries a single sequence of a specific oligonucleotide $D_s$-$L^{a,b}_{(+)}$ which is complementary to one of the multiple oligonucleotides $L^{a,b}_{(-)}$-$D_c$, attached to the core dendrimer $D_c$, the n being about 5. The complementary oligonucleotide $L_{(+)}$ of each shell dendrimer undergoes Watson-Crick hybridization with its corresponding complementary oligonucleotide $L_{(-)}$ of the core dendrimer. The complementary oligonucleotide $L_{(-)}$ of the core dendrimer is chemically modified to contain an additional dormant group, which can be chemically activated to allow for the formation of a covalent bond between the two hybridized oligonucleotides.

The chemical compositions of the complementary oligonucleotides $L_{(+)}$ and $L_{(-)}$ are exemplified by Locked Nucleic Acid (LNA). LNA is a novel class of nucleic acid analogs structurally similar to RNA nucleosides. The term "locked nucleic acid" has been coined to emphasize the conformational restriction of the furanose ring due to the presence of a methylene linker which connects 2'-O position to the 4"-C position structurally mimicking the standard RNA monomers. LNA oligomers conform to Watson-Crick base pairing rules and hybridize to complementary LNA as well as to complementary DNA and to RNA, with substantial thermal stability and selectivity. A duplex of complementary LNA/LNA displays greater stability than other nucleic acid duplexes (Koshkin, et al. J. Am. Chem. Soc., 120: 13252-13260, 1998). The self-complementary cysteine-terminated LNA 12-mers are synthesized by Proligo, LLC (Boulder, Colo.) having structures as follows: $LNA_{(+)}$: 5'-Cys-TAATACGACTCA-3' (SEQ ID NO: 58) and $LNA_{(-)}$: 3'-AT-TATGCTGAGTCys-5' (SEQ ID NO: 59). Five pairs of self-complementary cysteine-terminated LNA 12-mers with different nucleotide sequences are synthesized, to be attached to core and shell dendrimers.

Dendrimers are macromolecular nanoscale covalent core-shell assemblies composed of regularly placed atoms, repeat branching units (monomers) and terminal functional groups surrounding their the functional group of the focal points or cores (Tomalia et al, Pure Appl. Chem., 72(12): 2343-2358, 2000). Because of this structure, dendrimers serve as functional modules or building blocks for precisely designed therapeutics. The third generation polyamidoamine (PAMAM) G-3 dendrimer containing 32 surface primary amine groups is chosen as the core dendrimer, and five first generation PAMAM G-1 dendrimers each containing 8 surface primary amine groups are used as shell dendrimers (Tomalia et al., Pure and Applied Chemistry 72, 2343-2358, 2000). The core dendrimer is tethered to solid hydrophilic resin (Grøtli, et al. J. Combi. Chem. 2000, 108-119, 2000); Buchardt, et al. Tetrahedron Lett. 39: 8695-8698, 1998). Surface primary amines of $NH_2$-terminated G3-dendrimer are modified with Traut's reagent as described in Example 7, resulting in a $D_{SH}$ containing 32 SH-groups. Then 2 kDa PEG-derivatives $LNA^k$-PEG-MAL, each bearing a unique $LNA^k$, the k having a value of 5, are attached to the free SH-groups of the tethered core dendrimer $D_{MAL}$ in a sequential manner. Attachment of the first $LNA^1_{(+)}$ added at a 1:1 concentration ratio, occurs within the first 15 minutes at a temperature of 18 C, while attachment of all five LNAs occurs within 2 hours at T of 18 C. However the addition of subsequent LNA oligomers becomes progressively slower, with formation of a mixture of hepta-/octa-dendrimer conjugates after 60-64 hours.

Hybridization and subsequent covalent bond formation between multiple shell dendrimers and a single core dendrimer is carried out using five mono-functional PAMAM G-2 shell dendrimers $D_s^k$, each shell dendrimer carrying a single copy of $LNA^k_{(-)}$ having a nucleotide sequence that is complementary to one of the five $LNA^k_{(+)}$, k having a value of 1-5, that is covalently attached to the core PAMAM G-3 dendrimer $D_c$.

Example 11

Antiviral Complex mPEG-RNase I that Provides Controlled Release of RNase

Attachment of soluble degradable methoxy-polyethylene glycol succinyl succinate (mPEG-SS) to human RNase I providing controllable release of bound nuclease into solution, and increased proteolytic resistance and cellular uptake of the RNase.

Degradable PEG derivative bearing hydrolytically unstable group is exemplified by succinimidyl succinate (mPEG-SS). The mPEG-SS active ester reacts rapidly with amino group of proteins and forms an amide linkage (—CO—NH—). The linkage is subject to rapid hydrolysis and detachment of mPEG from the nuclease. To avoid hydrolysis that is too rapid, mPEG succinimidyl carbonate is used (see J. M. Harris, U.S. Pat. Application. No. 2001/0021763 A1).

Wild-type recombinant human RNase I is dissolved to a concentration of 25 mg/ml in distilled water and is applied to a Sephadex G-25 column (1.6×14.0 cm) in 10 mM $CaCl_2$. During elution, fractions of 2.0-2.2 ml are collected and optical density measured at 280 nm. The fractions with high optical density at 280 nm are combined. The protein concentration in the solution is about 6.5 mg/ml. To 8 mg of RNase I in 1.4 ml of 10 mM $CaCl_2$ purified by gel filtration, a mixture of 136.8 ml of 0.25 M phosphate potassium buffer (PPB), pH 8.0 and 127.4 ml of protease inhibitor PMSF (0.8 mg/ml) in 0.6 ml of distilled water is added, to give a final volume 2 ml. The solution is clarified by centrifugation.

To the clarified RNase I, 64 mg of mPEG-SS (in two portions) is added. The mixture is vortexed for 5 min and is then shaken moderately for 15 min at room temperature. Thereafter the solution is applied to a Sephadex G-75 column (1.6×3.0 cm), and the sample is eluted with 5 mM $CaCl_2$, and fractions of 2.0-2.4 ml collected. The protein content is detected spectrophotometrically at 280 nm.

The collected fractions are placed in an ice bath and aliquots of the sample having pegylated RNase I (5-15 mg) are diluted in a mixture of 1.5 ml PPB and 0.5 ml of fluorescamine in acetone (0.3 mg/ml) and the fluorescence of the mixture is measured at an excitation wavelength of 475 nm. Amount of primary amino groups in the protein is proportional to the tangent of the angle. The measurement by fluorescence of the rate of RNase I pegylation demonstrates that only 1-2 lysine residues are pegylated, and that spatial hindrances are created by the protein structure for the remaining lysine residues. Pegylation of human RNase I enhances its antiviral efficacy against ssRNA corona virus.

Example 12

Enhanced Hydrolytic Activity of Multiple-Charged (Mc) Recombinant Variants of Human DNase I Towards dsDNA The Example shows digestion of high-molecular weight salmon DNA (Sigma Corp., St. Louis, Mo.) with each of the following recombinant versions of multi-charged (mc) mcDNase I, having amino acid substitutions: (1) mcDNase (+2) with substitutions E13R/N74K that contribute two additional charges; (2) mcDNase (+3) with substitutions E13R/N74K/T205K that contribute three additional charges; (3) mcDNase (+5) with five substitutions E13R/T14K/H44R/N74K/T205K that contribute five additional charges; (4) actin-resistant version of DNase I [termed herein "arDNase" (+1)] with a substitution that contributes one additional charge A114R and providing resistance to an inhibitory effect of actin; and (5) hyperactive/actin-resistant version of mc/arDNase (+6) with substitutions E13R/T14K/H44R/N74K/T205K/A114R that contribute six additional charges.

Target dsDNA in phosphate buffer, pH 7.5, at a DNA concentration 5 ng/ml, approximates in vivo peak concentrations of viral DNA within an infected cell. This concentration is orders of magnitude lower than typical concentration of endogenous host DNA in serum (about 25-250 ng/ml; Pan, et al., J. Biol. Chem. 273, No 29: 18374-18381, 1998). Standard assay of DNase activity is based on conversion of acid-insoluble DNA polymer, precipitable by cold 2.25 mol/l perchloric acid, into non-precipitable acid soluble fragments that are 20 bp or less long determined spectrophotometrically at $\lambda=260$ nm (Dewez, et al., Eur. J. Clin. Chem. Clin. Biochem. 31, 793-797, 1993). The results performed in triplicate represent time required for 50% solubilization of 5 kbp dsDNA (500 µg/ml) by each of the mc and mc/ar-DNases (+1 to +6) positively charged variants, compared with the 50%-solubilization time of the same 5 kbp dsDNA samples digested by wild-type human DNase I.

The data presented in Table 2 show that versions of multi-charged recombinant human mcDNase I having substitutions of neutral amino acids by positively charged amino acids have greater hydrolytic activity against dsDNA in the presence of human serum, than wild type DNase I. Further, substitution A114R providing DNase I with actin-resistance contributes increased DNase I hydrolytic activity, presumably due to the presence of G-actin in human serum.

TABLE 2

Hydrolysis of dsDNA in human serum by native, multi-charged (mc) and actin-resistant (ar) variants of DNase I

| DNase I variants | Time $T_{50}$ (min) 50% DNA hydrolysis | Average $T_{50}$ (min) 50% DNA hrolysis |
|---|---|---|
| DNase I | 26; 28; 30 | 28 |
| mcDNase (+3) | 10; 11; 12 | 11 |
| mcDNase (+5) | 5; 6; 7 | 6 |
| arDNase (+1) | 2; 3; 4 | 3 |
| mc/arDNase (+6) | 0.5; 1; 1.5 | 1 |

Example 13

Chemical Nucleases Targeted to DNA and RNA Cleave Nucleic Acids Through the Fenton-Like Reaction A number of transition metal complexes are capable of incurring oxidative damage and thus can cleave DNA and RNA through a Fenton-like reaction. Chemical nuclease Fe (III)-BABE in the presence of $H_2O_2$ and an electron donor such as ascorbic acid generates massive quantities of hydroxyl radicals leading to the oxidative hydrolysis of viral DNA and RNA. Similar effects on DNA and RNA have been observed for Fe (II)-EDTA and Cu(II)-glutathione or glycine-glycine-lysine complexes. Some of these complexes, if targeted to viral nucleic acids, may serve as efficient antiviral agents.

The digestion of DNA and RNA by reactive oxygen species generated through Fenton-like reaction induced by interaction of Fe (II)-EDTA, hydrogen peroxide and ascorbic acid (Fe-HP-AA) as electron donor is shown in Table 2A. Hydrolysis of RNA and DNA is determined in Tris-HCl buffer pH 7.2, 0.1 mM Fe (II)-EDTA, 0.25 mM and 0.1 mM ascorbic acid for 30 mM at 37° C. as described (Dewez, et al., Eur. J. Clin. Chem. Clin. Biochem. 31, 793-797, 1993). The antiviral activity of the Fe(II)-complex is shown in Table 2B. Virus replication expressed in $TCD_{50}$/ml is assayed as described in Example 14.

TABLE 2A

| Substrate | Hydrolysis (%) Control | Hydrolysis (%) Fe-HP-AA |
|---|---|---|
| Yeast RNA | 3 | 64 |
| Salmon DNA | 2 | 72 |
| Virus | Control | Fe-HP-AA |
| Herpes simplex virus | 6.2; 6.4; 6.0 | 4.3; 4.2; 4.1 |
| Influenza virus | 7.4; 7.2; 7.5 | 5.2; 5.3; 5.4 |

Example 14

Enhanced Antiviral Activity of DNase-PEG-PNA Compared to DNase-PEG

The development of nuclease- and protease-resistant PNA molecules, capable of forming hydrogen bonds with complementary nucleotide sequences, provides a mechanism for addressing various ligands to targeted viral DNA and RNA molecules. PNA complementary to genomic DNA and forms of intermediate RNA of replicating pathogenic viruses are used herein to deliver nucleases to the target viral DNA and RNA molecules for hydrolysis of these nucleic acids and inhibition of replication of pathogenic viruses. Molecules with N-terminal lysine residues of 18-mer bis-PNA complementary to four different nucleotide sequences of vaccinia virus (VV) DNA sterically available for interaction, are conjugated with forked 2×20 kDa PEG and human DNase I (DNase) as described in Example 1.

The antiviral efficacy of these constructs targeted against VV are compared with that of non-modified wild-type human DNase I and DNase I conjugated with PEG. The efficacy of PNA targeting is illustrated by the data presented in Table 3. To assay the effect of the modified DNase I on the VV replication, host cells are grown in 199/Eagle's medium (45%+45%) with 10% inactivated fetal bovine serum (FBS). Growth medium 199 is used to maintain cells. Antiviral activity of enzymes on the virus replication rate is determined by the effect of the enzymes administered in cell culture inoculated with 100 $TCD_{50}$/0.1 ml of cytomegalovirus (CMV). DNases are administered in amounts of 500 KuU/ml. CMV-inoculated cells treated with mcDNase and nbDNase are incubated for 48 h at 37° C. Thereafter, the cells are frozen and the titer is determined and expressed in log TCD/0.1 ml.

TABLE 3

Antiviral activity of modified DNase I against cytomegalovirus

| Nuclease [500 UA/ml] | Virus Titer [$logTCD_{50}$/0.1 ml] | Average Titer [$logTCD_{50}$/0.1 ml] |
|---|---|---|
| Control [0] | 7.3, 7.6, 7.4 | 7.4 |
| DNase | 6.3, 6.4, 6.5 | 6.5 |
| PEG-DNase | 3.2, 3.4, 3.5 | 3.4 |
| $(PNA)_2$-PEG-DNase | 0.2, 0.3, 0.4 | 0.3 |

The data show that while DNase is effective, PEG-DNase is more effective, and $(PNA)_2$-PEG DNase is even more effective than unmodified DNase.

Example 15

R8-PEG-DNase Exhibits Enhanced Antiviral Activity Against Vaccinia Virus (VV)

The cellular uptake of bovine DNase I (DNase), DNase-PEG and DNase-PEG-R8 complex is evaluated using the HepG2 cell line (human hepatocarcinoma cells ATCC, No-HB-8065). HepG2 cells were grown at 37° C. in 199/Eagle's medium (45%+45%) with 10% fetal bovine serum (FBS) heat-inactivated at 56° C. for 30 min. DNase I is labeled with fluorescent rodamine (*) according to the manufacturer's instruction (Pierce, Inc., Rockford, Ill.). Penetration of *DNase-PEG-K-R8 into HepG2 cells is compared to that of *DNase and *DNase-PEG after 30 min of incubation with HepG2 cells in DMEM at 37° C.

Scanning of cell preparations with a fluorimeter shows that uptake of DNase-PEG-R8 into HepG2 cells is significantly greater than that of DNase-PEG and DNase alone (Table 4A). To study the effect of the modified DNase on VV replication, cells are grown in 199/Eagle's medium (45%+45%) with 10% of inactivated fetus bovine serum (FBS). To maintain the cells the growth medium 199 is used.

Antiviral activity of DNase-derived compositions is determined by analyzing the effect of the enzymes administered in cell culture on the virus replication rate cells inoculated with 100 TCD$_{50}$/0.1 ml of VV. DNases are administered in amounts of 500 KuU/ml. VV inoculated cells treated with DNase and DNase complexes are incubated for 48 h at 37° C. Thereafter, the cells were frozen and the VV titer is determined and expressed in log TCD/0.1 ml. The antiviral effect of the DNase-complexes is shown in Table 4B.

Cellular Uptake of Rhodamine-Labeled *DNase, PEG-*DNase and PEG-*DNase-R8 Complexes into Intact and Vaccinia Virus VV-Infected HepG2 Cells

| Labeled *DNase | Modified | OD (430 nm) | Labeled *DNase | Modified | OD (430 nm) |
|---|---|---|---|---|---|
| HepG2 intact cells | | | HepG2 VV-infected cells | | |
| *DNase | | 37 | *DNase | | 48 |
| *DNase-PEG | | 45 | *DNase-PEG | | 55 |
| *DNase-R8 | | 87 | *DNase-R8 | | 95 |
| *DNase-PEG-R8 | | 105 | *DNase-PEG-R8 | | 130 |

Antiviral Activity of DNase, PEG-DNase and PEG-DNase-R8 Complexes on Replication of Vaccinia Virus in HepG2 Cells

| Modified DNase HepG2 intact cells | log TCD50 | Average log TCD50 |
|---|---|---|
| Control | 6.8; 6.6; 6.6 | 6.6 |
| DNase | 4.6; 4.8; 4.8 | 4.7 |
| DNase-PEG | 4.0; 4.0; 3.8 | 3.9 |
| DNase-R8 | 3.0; 3.2; 3.2 | 3.1 |
| DNase-PEG-R8 | 2.3; 2.4; 2.2 | 2.3 |

Example 16

Synergistic Inhibitory Effect of Combined Application of R8-PNA-PEG-DNase and R8-PNA-PEG-RNase on Replication of Vaccinia Virus (VV)

Since intermediate forms of viral RNA appear during replication of VV DNA, the combined effect of MPP-PEG-PNA-DNase and MPP-PEG-PNA-RNase should result in a stronger inhibitory effect on replication of VV than each of these preparations separately. The MPP-PEG-PNA-RNase and MPP-PNA-PEG-DNase complexes are prepared as described in Example 1. Vaccinia virus (VV) during replication forms intermediate mRNA molecules that encode viral proteins. A combination of modified DNase I, to digest viral genomic DNA, and modified RNase, to digest intermediate viral RNA, significantly enhances antiviral effects of DNase against VV, as shown in Table 5. Antiviral effect of combined application of DNase-PEG-PNA-R8 and RNase-PEG-PNA-R8 on replication of vaccinia virus (vv).

| Nuclease | Titer of VV, log TCD/0.1 ml | Average Titer of VV |
|---|---|---|
| Control | 7.4; 7.0; 7.2 | 7.2 |
| DNase-PEG-PNA-R8 | 4.7; 5.0; 5.2 | 4.9 |
| RNase-PEG-PNA-R8 | 6.5; 6.7; 6.5 | 6.56 |
| DNase-PEG-PNA-R8 + RNase-PEG-PNA + R8 | 2.4; 2.2; 2.0 | 2.2 |

Example 17

Synergistic Inhibitory Effect of Combined Human DNase I, RNase I and RNase H on HIV Replication Replication of HIV is initiated by reverse transcription of viral genomic RNA, to form hybrid RNA-DNA, the RNA susceptible to digestion by RNase H. A single-stranded DNA is replicated and dsDNA is integrated into the host genome, to be transcribed by DNA-dependent RNA polymerase. The newly appearing mRNA is translated to form reverse transcriptase (RT) and capsid proteins. Therefore, a combination of an RNase H for digesting RNA within the hybrid RNA-DNA molecule, a ssDNase such as Ser-His-Asp (SHD) for digesting ssDNA that remains after hydrolysis of RNA within RNA-DNA hybrid, a DNase I that can digest dsDNA, and an RNase I for digesting RNA, can act together to create a strong anti-HIV complex.

The experiment described herein demonstrates efficacy of such an anti-HIV complex. MT-4 cells are cultured in 96-well microplates in Eagle's medium supplemented by 10% heat-inactivated FBS, 300 μg/ml L-glutamine and 100 μg/ml streptomycin, and are infected by mixing the cell suspension (2×10$^6$ cells per ml) with the virus suspension. The multiplicity of infection (MOI) is 0.2. The mixture is incubated for 1 h at 37° C. for virus adsorption. The infected cells are then diluted to a concentration of 5×10$^5$ cells per ml by adding fresh complete medium, and are cultured at 37° C. in a 5% CO$_2$ atmosphere in the presence or absence of various combinations of nucleases in 96-well microplates, in triplicate for each concentration. The control cells are cultured under the same conditions.

Anti-HIV Activity of the Combination of Modified Nucleases

| Nucleases [UA/ml] | Mean RT Activity [%] | p24 [%] |
|---|---|---|
| Non-infected MT-4 cells: | | |
| DNase-PEG [0; 10; 100; 500] | n.d. | n.d |
| HIV-infected MT-4 cells | | |
| DNase-PEG [0; 10; 100; 500] | [100; 47; 27; 15] | [100; 27; 19; 11] |
| RNase-PEG [0; 10; 100; 500] | [100; 54; 41; 21] | [100; 37; 22; 15] |
| RNaseH-PEG [0; 10; 100; 500] | [100; 41; 23; 12] | [100; 31; 22; 18] |
| (DNase + RNase)-PEG [0; 10; 100; 500] | [100; 26; 15; 10] | [100; 12; 8; 5] |
| (DNase + RNase + RNaseH)-PEG [0; 10; 100; 500] | [100; 12; 5; 2] | [100; 7; 4; 1] |

Example 18

HIV does not Develop Resistance to Treatment by Nucleases

Emergence of HIV isolates that acquire resistance to the drugs used to treat AIDS patients is one of the pivotal problems in AIDS therapy. The nucleoside analogues, starting from AZT, non-nucleoside reverse transcriptase inhibitors (NNRT) and HIV protease inhibitors eventually induce HIV resistance and loose their therapeutic activity. As a rule, drug-resistance is developed due to the mutations altering the nucleotide sequences of genes encoding the HIV structures such as reverse transcriptase (RT) or HIV protease targeted by anti-HIV drugs.

Nucleases in contrast to inhibitory drugs digest viral nucleic acids, splitting phosphodiester bonds between nucleotides regardless of the mutational alterations in the nucleotide sequences of viral genome. The change in the chemical nature of inter-nucleotide bonds required for making such bonds resistant to nucleases are not mutationally possible. In order to replicate, viral nucleic acids dissociate themselves from protecting proteins and, therefore, become susceptible to hydrolytic action of nucleases, leaving little chance of survival of mutants with altered sequences. The experiments in this example are designed to demonstrate this conception.

MT-4 cells are infected with wild-type HIV-1 (HXB2). Infected MT-4 cells are then exposed to low concentrations of AZT or the nucleolytic composition RDP of the present invention, a formulation consisting of human RNase-PEG-PNA-R8+human DNase-PEG-PNA-R8+synthetic nucleolytic tri-peptide D-Ser-His-D-Asp (P). The nucleases are covalently attached to PEG, R8 and PNA as described in Example 1. Progeny virus was recovered and serially passaged in MT-cells in the presence of increasing concentrations of either AZT or RDP. The sensitivity of virus recovered after each passage to AZT or RDP is assessed by a plaque reduction assay performed in CD4+ HeLa cells.

Emergence of resistant virus is observed in AZT treated cells, as is shown by the progressive virus growth during each subsequent passage. By the fourth passage of HIV-1 in AZT-treated MT-4 cells $IC_{50}$ values exceed 50 μM. When tested at higher concentrations of AZT, the $IC_{50}$ values of sixth passage of virus is in excess of 250 μM, representing a >1000-fold shift in sensitivity. In contrast, a rise of resistance to RDP is not observed even by the $10^{th}$ passage. The presented data support the concept that resistance to nucleases does not develop even after very long-term treatment.

To study inhibition of HIV-1 by the applied drugs, cells are inoculated at a multiplicity of infection (MOI) of 0.1 $TCID_{50}$ per cell and distributed into triplicate wells of 96 well plates ($10^4$ cells per well) containing serial twofold dilutions of drug. Complete killing of cells that are not drug-treated occurs on day 7, as determined by the MTT-dye reduction method. Table 7 shows that virus susceptibility to AZT significantly decreases with each passage, while virus remains susceptible to RDP after each consecutive passage.

HeLa cells expressing CD4+ used in a plaque reduction assay are as described in (Larder et al., Lancet 243, 1731-1734, 1989). Briefly, 24-well culture plates containing cell monolayers are inoculated with virus in various concentrations of antiviral drug in medium. Duplicate wells are prepared for each dilution, and the percentage plaque reduction is determined based on the value of the control without the drug. The $IC_{50}$ is calculated with the median effect plot. As shown in Table 7, HIV-1 infected cell culture is serially passaged with increasing the AZT and RDP concentrations. Drug concentration is guided by the degree of viral replication of the previous passage. The Table shows that culture with AZT results in appearance of AZT-resistant HIV-1, however, culture with RDP does not cause the appearance of resistant viruses.

Progressive Increase of HIV-1 In Vitro Resistance to AZT but not to RDP

| Number of Passages | HIV-1 infectivity [$\log_{10} TCID_{50}$/ml] | | | |
|---|---|---|---|---|
| No | −AZT | +AZT | −RDP | +RDP |
| 0 | 6.5 | 2.8 | 6.7 | 2.3 |
| 1 | 6.1 | 2.6 | 6.5 | 2.4 |
| 2 | 6.3 | 3.8 | 6.6 | 2.3 |
| 5 | 6.4 | 4.7 | 6.4 | 2.2 |
| 15 | 6.2 | 5.9 | 6.3 | 2.1 |

Example 19

Improving PEG-DNase Complex Antiviral Activity Against HIV by Attaching CD4 Surface Receptor that Interacts with HIV Protein gp120

Many host cells targeted by enveloped viruses display cell surface receptors (CSR) with high binding affinity to certain viral envelope lipoproteins responsible for viral fusion and that are expressed on the cell membrane of infected cells. The CD4 surface receptor of T4 lymphocytes has high affinity for HIV protein gp120. In this example it is shown that Bovine DNase-PEG-CD4 complex exhibits a higher concentration of the compound inside HIV-infected cells, and has a greater anti-HIV activity compared to DNase-PEG. The data in Table 8 show that DNase-PEG-CD4 treatment results in decreased amounts of two HIV products, RT and p24, compared to DNase-PEG treatment.

Attachment of CD4 CSR to DNase-PEG Complex Increases Anti-HIV Activity

| Nucleases [UA/ml] | Mean RT Activity [%] | p24 [%] |
|---|---|---|
| Non-infected MT-4 cells: | | |
| DNase-PEG [0, 100; 500] | n.d | n.d. |
| DNase-PEG-CD4 [0; 100; 500] | n.d. | n.d |

| Nucleases [UA/ml] | Mean RT Activity [%] | p24 [%] |
|---|---|---|
| HIV-infected MT-4 cells | | |
| DNase-PEG [0; 100; 500] | [100; 27; 15] | [100; 19; 11] |
| DNase-PEG-CD4 [0; 100; 500] | [100; 11; 4] | [100; 6.5; 2.3] |

Example 20

Prevention of AIDS and Other Viral Diseases by Intranasal, Per Oral or Other Non-Parenteral Administration of Nucleases Antiviral nucleases are modified to be resistant to gastrointestinal proteases for application by per oral, intranasal or other non-parenteral routes. Resistance of nucleases to endogenous proteases is achieved by attachment of PEG and hydrophobic entities such as DSPE and/or protease inhibitors. We demonstrate that inhalation of aerosol of pegylated Benzonase, the enzyme having DNase and RNase activities, prevents or reduces extent of infection in calves by each of RNA parainfluenza virus and DNA adenovirus. It is shown also that the composition of human DNase-PEG-DSPE+ human RNase-PEG-DSPE protects volunteers against respiratory diseases caused by infection with DNA adenovirus and RNA influenza virus. Compositions of other enzymes digesting both RNA and DNA such as (D-Ser-His-D-Asp)-PEG-DSPE, modified to be resistant to gastrointestinal proteases by attachment of PEG and a hydrophobic entity such as DSPE and/or protease inhibitors, can be used for prevention of AIDS by peroral application administered, for example, as pills. An alternative route of delivery is inhalation of aerosols of the nucleases formulated for resistance to endogenous proteases as described above.

Example 21

Antiviral Activity of Modified RNase A in Mice Infected with Influenza Virus

Influenza virus A/Aichi/2/68/H3N2 adapted to replication in mouse lungs is used in the experiments of this Example. The titer of virus is 5.0 log $LD_{50}$. Mice (body weight 15-17 g) are inoculated by intranasal administration of virus in a dose of 10 $LD_{50}$ in 0.05 ml, 20 mice in each group. After infection mice are treated by intraperitoneal or intranasal administration of bovine RNase A (RNase), RNase-PEG or RNase-PEG-R8 in a dose of 2000 UA/g of body weight. Preparations of RNase are administered on the first, third and fifth days after the infection, and animals are observed for 15 days. Control animals are administered Hanks solution by the same route. Survival of animals and the influenza virus titer in their lungs are determined as described in Example 13.

Survival of animals and the influenza virus titer in the animal lungs are used as criteria of efficacy of the treatment shown in Table 9. RNase-PEG and RNase-PEG-R8 were efficacious in reducing viral titer and increasing survival, with the most efficacious agent being RNase-PEG-R8.

Antiviral Activity of Modified RNase in Mice Inoculated by Influenza Virus Administered by Intraperitoneal (i.p.) or Intranasal (i.n.) Routes

| | Survival of Animals | Titer in lungs [log $TCD_{50}$] |
|---|---|---|
| Treatment i.p.: | | |
| Control | 20/1 | 6.6; 6.4; 6.7 |
| RNase | 20/11 | 4.7; 5.0; 4.5 |
| RNase-PEG | 20/16 | 3.2; 3.4; 3.1 |
| RNase-PEG-R8 | 20/20 | 1.8; 2.0; 1.9 |
| Treatment i.n.: | | |
| RNase | 20/13 | 4.5; 4.0; 4.3 |
| RNase-PEG | 20/19 | 3.0; 3.1; 3.1 |
| RNase-PEG-R8 | 20/20 | 1.4; 1.0; 1.4 |

Example 22

Attachment of PEG, PNA and R8 to Genetically-Engineered Protease-Resistant (Pr) Human RNase I Enhances Nuclease Antiviral Activity Against West Nile Virus (WNV)

Comparative antiviral activity of each of recombinant human RNase I (RNase), genetically-engineered protease-resistant prRNase, prRNase-PEG, prRNase-PEG-R8 and prRNase-PEG-PNA-R8 against ssRNA West Nile virus is studied. R8 and PNA were each prepared synthetically, having a sequence complementary to the nucleotide sequence of a selected site of ssRNA West Nile virus genome, and were attached to PEG as described in Example 1.

Antiviral activity of RNase, prRNase, PEG-prRNase, MPP-PEG-rRNase and MPP-PEG-rRNase-PNA against ssRNA WNV is studied. WNV and monolayer culture of newborn rabbit kidney cells (RKC) were obtained from ATCC. Cell medium consists of 0.5 lactalbumin hydrolysate and Hanks medium (45%+45%) and 10% FBS. The maintenance medium does not contain FBS. Antiviral effect of RNase, prRNase, PEG-prRNase, MPP-PEG-rRNase and PNA-prRNase-PEG-PEG-rRNase-PNA against ssRNA WNV is compared. The experimental data in Table 1 demonstrate that prRNase-PEG-PNA-R8 complex has the highest antiviral activity against West Nile virus. The doses of the antiviral complexes are expressed in the units of RNase activity (UA). All values are the average of four replicate determinations.

Antiviral Effect of Modified RNase I Against West Nile Virus

| RNase I [UA/ml] | $logTCD_{50}$/ml |
|---|---|
| RNase [0; 100; 250] | [8.7; 7.77.0] |
| prRNase [0; 100; 250] | [8.5; 6.3; 6.1] |
| prRNase-PEG [0; 100; 250] | [8.4; 5.8; 5.0] |
| prRNase-PEG-R8 [0; 100; 250] | [8.5; 4.1; 3.3] |
| prRNase-PEG-PNA-R8 [0; 100; 250] | [8.4; 2.0; 1.3] |

Example 23

The Antiviral Effect of Combination of Nucleases Against FMD Virus

Foot-and-mouth disease (FMD) is a cause of epizootics in many countries, leading to death or sacrifice of thousands of animals and significant economic losses. FMD is caused by a ssRNA virus (FMDV). During its replication, viral genomic ssRNA is transformed into dsRNA form, which is translated to provide viral proteins and transcribed to synthesize progeny viral ssRNAs, which are assembled into FMD virions.

Table 1 shows that a combination of bovine RNase A, digesting ssRNA, and bovine RNase III or Benzonase®, for the purpose of digesting dsRNA, exhibits a greater antiviral effect than each of the enzymes applied separately. Attachment of the enzymes to PEG further increases the antiviral effect of the combined treatment.

Synergistic Effect of Combined RNase a and RNase III Treatment on Replication of FMD virus in vitro

| Nucleases [UA/ml] | Titer [logTCD50/ml] |
|---|---|
| Control | 9.3; 9.0; 9.0 |
| RNase [100] | 7.3; 7.1; 6.8 |
| RNase III [100] | 7.4; 7.3; 7.3 |
| RNase [50] + RNase III [50] | 4.6; 4.3; 4.3 |

Example 24

Prevention of FMD in Animals in Contact with the FMD Virus Infected Cattle

Prevention of epizootics of foot-and-mouth disease (FMD) is generally achieved by isolating and killing the infected animals and animals in contact with infected animals. We demonstrate that preventive treatment of animals in contact with sick rabbits but not showing symptoms of FMD, by administering both bovine RNase A (RNase) and RNase-PEG conjugate, effectively prevents the development of the disease in rabbits. The example also shows enhanced preventive effect of RNase-PEG compared with that of RNase A.

FMDV of O-type is diluted in 0.5% lactalbumin hydrolysate in Earl's medium, and is injected s.c. (500 UA of RNase A within 3 hours after s.c. inoculation of 1000 $LD_{50}$ of FMDV). Table 12 shows that a single dose is sufficient to prevent the development of FMD in guinea pigs. The preventive effect of RNase lasts for at least 4 hours after a single injection of the enzyme, while a preventive effect of RNase-PEG lasts for at least about 100 hours after the injection. Out of 40 guinea pigs pretreated with a single s.c. injection of 500 UA of RNase-PEG and subsequently infected with FMD virus, only 2 developed FMD compared with 8 animals developing FMD after single injection of RNase. In the control group all 40 animals manifest general symptoms FMD after inoculation with virus. Most importantly, all infected and RNase-treated animals are resistant to FMD following subsequent repeated infection.

Preventive Effect of RNase and RNase-PEG in Animals Infected by FMD Virus

| Nuclease [UA/ml] | FMDV [$LD_{50}$] | Guinea Pigs | Survived |
|---|---|---|---|
| Control: RNase [0] | 1000 | 40 | 3 |
| Control: RNase [500] | 0 | 40 | 40 |
| RNase [500] | 1000 | 40 | 32 |
| RNase-PEG [500] | 1000 | 40 | 38 |

Example 25

Multiply-Charged (mc) Human DNase I Exhibits Enhanced Antiviral Activity Against dsDNA Herpes Simplex Virus In Vitro The example shows that significantly higher antiviral activity is obtained by treatment with multiply-charged recombinant human pancreatic DNase I (mcDNase) against herpes virus, compared with that obtained with the wild-type recombinant human DNase I (DNase). The mcDNase I is characterized by an increased hydrolytic activity towards its preferred dsDNA substrate, and significantly decreased binding affinity to G-actin, a potent inhibitor of DNase I. The recombinant mcDNase I harbors substitutions $E13CR^{2+}$/$T14K/H44R/N74K/T205K/A114CR^{2+}$ of amino acids at six positions, providing 8 additional positive charges in the amino acid sequence: where T14, H44, N74 and T205 amino acids are replaced by singly-charged positive lysine, and E13 and A114 amino acids are substituted with Cys (C) residues with subsequent chemical modified by positively doubly-charged chemical reagent 2-bis(trimethyl ammonium)ethyl thiol ($CR^{2+}$).

Herpes simplex virus, type I (HSV-1), infectious titer 5.5 log $TCD_{50}$/0.1 ml, and cell culture HEP-2 were obtained from ATCC. Cells are grown in 199/Eagle's medium (45%+45%) with 10% of inactivated fetal bovine serum (FBS). To maintain the cells the growth medium 199 is used. Antiviral activity of enzymes was determined by the effect on the virus replication rate of different doses of enzymes added to a cell culture inoculated with 100 $TCD_{50}$/0.1 ml of HVS-1 on the virus replication rate. Each of DNase and mcDNase are administered in amounts of 10, 100, 500 and 1000 UA/ml. HEP-2 cells pre-treated with mcDNase and DNase are inoculated with HSV-1 and incubated for 48 h at 37° C. Thereafter, the cells are frozen and the HVS-1 titer is determined and expressed as log TCD/0.1 ml.

The antiviral effect of DNase and mcDNase (+8) against HSV-1 is shown in Table 13. The data show that mcDNase and DNase are effective in reducing the HSV titer, both as a function of concentration. Further, mcDNase was more effective than DNase, at each concentration.

Anti-HSV-1 Activity of Human mcDNase (+8) and DNase I

| Nuclease [UA/ml] | HSV Titer [logTCD$_{50}$/ml] | Average Titer |
|---|---|---|
| Control [0] | 5.5; 5.6; 5.7 | 5.6 |
| DNase [10] | 5.4; 5.5; 5.3 | 5.4 |
| DNase [50] | 5.1; 5.0; 5.1 | 5.1 |
| DNase [100] | 4.6; 4.5; 4.7 | 4.5 |
| DNase [500] | 3.8; 3.9; 3.7 | 3.8 |
| mcDNase [10] | 4.0; 3.9; 3.9 | 3.9 |
| mcDNase [50] | 3.5; 3.4; 3.3 | 3.4 |
| mcDNase [100] | 3.0; 3.2; 3.1 | 3.1 |
| mcDNase [500] | 2.7; 2.8; 2.9 | 2.8 |

Example 26

Enhanced Antiviral Activity of Actin-Resistant Variant of Human DNase I Against dsDNA Cytomegalovirus The Example shows that actin-resistant and multi-charged variant of recombinant human DNase I (+2) (arDNase) with a single substitution Ala114/$CR^{2+}$ (see Example 25), which decreases the interaction of enzyme with the inhibitory actin, possesses enhanced antiviral activity against dsDNA cytomegalovirus (CMV) compared with wild-type recombinant human DNase (DNase). CMV (infectious titer 5.5 log $TCD_{50}/0.1$ ml) and cell culture HEP-2 are obtained from ATCC. Cells are grown in 199/Eagle's medium (45%+45%) with 10% of inactivated fetal bovine serum (FBS). To maintain cells the growth medium 199 is used. Antiviral activity of enzymes is determined by extent of effect of the nucleases on virus replication rates. DNase and arDNase are added to the cell culture inoculated with 100 $TCD_{50}/0.1$ ml of CMV in the amounts of 10, 50, 100 and 500 UA/ml. The CMV inoculated HEP-2 cells are treated with DNase and arDNase and incubated for 48 hours at 37° C. Thereafter, the cells are frozen and the CMV titer is determined and expressed as log TCD/0.1 ml as shown in Table 14.

The data show that both DNase and arDNase are effective in reducing CMV titer, with arDNase more effective than DNase at each concentration used.

Anti CMV Activity of Human arDNase I and DNase

| Nuclease [UA/ml] | CMV Titer [logTCD$_{50}$/ml] | Average Titer |
| --- | --- | --- |
| Control [0] | 5.6; 6;0; 5.8 | 5.8 |
| DNase [0] | 5.4; 5.6; 5.5 | 5.5 |
| DNase [50] | 5.1; 5.0; 5.1 | 5.1 |
| DNase [100] | 4.6; 4.5; 4.7 | 4.5 |
| DNase [500] | 3.8; 3.9; 3.7 | 3.8 |
| arDNase [10] | 4.0; 3.9; 3.9 | 3.9 |
| arDNase [50] | 3.5; 3.4; 3.3 | 3.4 |
| arDNase [100] | 3.0; 3.2; 3.1 | 3.1 |
| arDNase [500] | 2.7; 2.8; 2.9 | 2.8 |

Example 27

Inhibitory Effect of D-Ser-his-D-Asp-PEG-R8 and D-Ser-his-D-Asp on Replication of Herpes Virus Simplex I (HSV-I)

The data in Table 15 show antiviral activity of the nucleolytic tri-peptide carrying non-natural D-amino acids D-Ser-His-D-Asp, and significantly enhanced antiviral activity of $P_3$ covalently associated with PEG and membrane penetrating peptide R8: P-PEG-R8 against herpes virus simplex I (HSV-I) in vitro.

Antiviral Effect of Tri-Peptide $P_3$ and P-PEG-R8 on Replication of HSV-1

| Nuclease [UA/ml] | HSV Titer [logTCD$_{50}$/ml] | Average Titer |
| --- | --- | --- |
| Control [0] | 5.6; 6;0; 5.8 | 5.8 |
| $P_3$ [10] | 5.8; 5.6; 5.7 | 5.7 |
| $P_3$ [50] | 5.5; 5.4; 5.3 | 5.4 |
| $P_3$ [100] | 5.2; 5.3; 5.1 | 5.1 |
| $P_3$ [500] | 4.8; 4.9; 4.7 | 4.8 |
| $P_3$-PEG-R8 [10] | 5.1; 5.3; 5.2 | 5.2 |
| $P_3$-PEG-R8 [50] | 4.8; 4.9; 4.9 | 4.9 |
| $P_3$-PEG-R8 [100] | 4.1; 4.0; 4.1 | 4.1 |
| $P_3$-PEG-R8 [500] | 3.7; 3.8; 3.9 | 3.8 |

Example 28

Bovine RNase a with Preferred Hydrolytic Activity Towards ssRNA is More Efficacious in Inhibition of the Replication of ssRNA Coronavirus than that of dsRNA Reovirus The Example shows that bovine RNase A, which exhibits preferential hydrolytic activity towards an ssRNA substrate, inhibits replication of ssRNA coronavirus more efficaciously than it inhibits replication of dsRNA reovirus. A similar effect is observed comparing resistance to proteases (prRNase) of recombinant bovine RNase A, and its derivatives having a substitution of A20P. RNase A (200 UA) reduces coronavirus titer from 5.8 to 1.5 log TCD/0.1 ml, while titer of reovirus is reduced from 5.0 to 4.0 log $TCD_{50}/0.1$ ml. Both viruses are grown in HEP-2 cells in a medium consisting of lactalbumin and 199 medium in equal amounts supplemented with 10% of FBS. HEP-2 monolayers in 10 cm plastic dishes are inoculated with 100 $TCD_{50}/0.1$ ml of coronavirus or reovirus. Nucleases are added to the medium after 60 min of virus adsorption.

RNase a Exhibits Greater Antiviral Activity Against ssRNA Coronavirus Compared to Activity Against dsRNA Reovirus

| Nuclease [UA/ml]/virus | Titer [logTCD$_{50}$/0.1 ml] | Average Titer |
| --- | --- | --- |
| RNase A [0]/Coronavirus | 5.6; 6.3; 6.0 | 5.8 |
| RNase A [200]/Coronavirus | 1.4; 1.6; 1.5 | 1.5 |
| RNase A [0]/Reovirus | 5.0; 5.2; 4.8 | 5.0 |
| RNase A [200]/Reovirus | 4.0; 4.1; 3.9 | 4.0 |

Example 29

Human RNase III Inhibits Replication of dsRNA Reovirus to a Greater Extent than that of ssRNA Coronavirus The Example demonstrates that human RNase III, having preferential hydrolytic activity towards dsRNA compared to ssRNA, inhibits replication of dsRNA reovirus to a greater extent than that of ssRNA coronavirus (see Table 17). RNase III inhibits efficiently replication of dsRNA Reovirus but not ssRNA Coronavirus

| Nuclease [UA/ml]/virus | Titer [logTCD$_{50}$/0.1 ml] | Average Titer |
| --- | --- | --- |
| RNase III [0]/Coronavirus | 5.6; 6.3; 6.0 | 5.83 |
| RNase III [200]/Coronavirus | 4.5; 4.7; 4.6 | 4.5 |
| RNase III [0]/Reovirus | 5.0; 5.1; 4.8 | 4.9 |
| RNase III [200]/Reovirus | 2.5; 2.6; 2.4 | 2.5 |

Example 30

Synergistic Antiviral Activity of Human RNase I and RNase III Against dsRNA

During replication of dsRNA viruses, exemplified by reovirus, the viral genomic dsRNA is unprotected and is susceptible to RNase III, and intermediate ssRNAs that are susceptible to RNase A are synthesized.

The example demonstrates that administration of a therapeutic composition having combined human RNase III and human RNase I results in greater antiviral activity against replication of dsRNA reovirus than administration of each of these enzymes separately, in equivalent amounts of enzymatic units of activity (UA/ml) (see Table 18). The reovirus stock preparation used in this example has a titer of 5.5 log $CPD_{50}/0.1$ ml. Virus is grown in HEP-2 cells in a medium consisting of lactalbumin: 199 medium in equal amounts supplemented with 10% of FBS. HEP-2 monolayers in 10 cm plastic dishes are inoculated with 100 $CPD_{50}/0.1$ ml of reovirus. The nucleases are added to the medium after 60 min of virus adsorption.

TABLE 18

Synergistic antiviral activity of combination of human RNase I and human RNase III against dsRNA reovirus

| Nuclease [UA/ml] | Titer [logTCD$_{50}$/0.1 ml] | Average Titer |
|---|---|---|
| Control [0] | 5.6; 6.3; 6.0 | 5.8 |
| RNase I [200] | 3.9; 4.0; 4.1 | 4.0 |
| RNase III [200] | 2.6; 2.7; 2.8 | 2.7 |
| RNase I (100) + RNase III [100] | 1.7; 1.9; 1.7 | 1.8 |

Example 31

The RI-Resistant and Protease-Resistant Variant of Human RNase I (iprRNase) is More Active Against ssRNA Coronavirus a than Wild-Type RNase I The example shows that the genetically engineered RI- and protease-resistant variant of human RNase I having amino acid substitutions Q11A/A20P/N71A/E111A exhibits significantly higher antiviral activity against ssRNA coronavirus compared to that of wild-type (wt) human RNase I (see Table 19). Conditions of the experiment are as described in previous examples.

Recombinant RI- and protease-resistant iprRNase A more efficiently inhibit replication of ssRNA coronavirus than wild-type (wt) RNase A.

| Nuclease [UA/ml] | Titer [logTCD$_{50}$/0.1 ml] | Average Titer |
|---|---|---|
| Control [0] | 5.6; 6.3; 6.0 | 5.8 |
| RNase I [200] | 3.9; 4.0; 4.1 | 4.0 |
| iprRNase I (200) | 1.9; 2.0; 2.1 | 1.9 |

Example 32

Benzonase, a Nuclease with Hydrolytic Activity Against DNA and RNA, Inhibits Replication of ssDNA, dsDNA, ssRNA and dsRNA Viruses The example demonstrates that bacterial nuclease Benzonase®, a nuclease having high hydrolytic activity with each of single-stranded and double stranded DNA and RNA substrates, effectively inhibits replication of dsDNA vaccinia virus, ssDNA parvovirus, dsRNA reovirus and ssRNA coronavirus (see Table 20). Conditions of cell culture experiments are given in previous examples.

Benzonase Inhibits Replication of Single-Stranded and Double Stranded DNA and RNA Viruses

| Benzonase [µg/ml]/virus | Average Titer [log TCD$_{50}$/0.1 ml] |
|---|---|
| [0; 10; 25]/dsDNA-Vaccinia virus | 5.6; 4.6; 3.7 |
| [0; 10; 25]/ssDNA-Parvovirus | 4.8; 4.0; 2.9 |
| [0; 10; 25]/dsRNA-Reovirus | 6.8; 5.9; 4.2 |
| [0; 10; 25]/ssRNA-Coronavirus | 6.2; 4.5; 3.8 |

Example 33

Enhanced Antiviral Activity of iprRNase-PEG-R8 Compared to that of iprRNase Against ssRNA Corona Viruses The genetically-engineered RI- and protease-resistant variant of human RNase I (riprRNase I) having substitutions Q11A/A20P/N71A/E111A and covalently attached to PEG-R8 exhibits much greater antiviral activity against ssRNA corona virus than native RNase I. Attachment of 2×10 kDa CHO-PEG-R8 to the N-terminal amine of riprRNase I is carried out at pH of 5.0 following the procedure described in Example 1. The modified iprRNase (25 mg) dissolved in 1 ml of distilled water is applied to a Sephadex G-25 column (1.6×14.0 cm) in 10 mM CaCl$_2$. Fractions of 2.0-2.2 ml are collected and their optical density is measured at 280 nm. The fractions with a high optical density at 280 nm are combined. This solution has a protein concentration of about 6.5 mg/ml. To iprRNase I (8 mg in 1.4 ml of 10 mM CaCl$_2$), purified by gel-filtration, a mixture of 136.8 ml of 0.25 M phosphate potassium buffer (PPB), pH 8.0 and 127.4 ml of protease inhibitor PMSF (0.8 mg/ml) in 0.6 ml of distilled water is added (final volume 2 ml).

The suspension is centrifuged to clarify, the supernatant solution is applied to a Sephadex G-75 column (1.6×3.0 cm), and the product is eluted with 5 mM CaCl$_2$ (2.0-2.4 ml fractions). The protein content is detected spectrophotometrically at 280 nm6, and the product is stored at 4° C.

Aliquots of RNase I (5-15 mg) pegylated as above are diluted in 1.5 ml phosphate buffer pH 7.5, and 0.5 ml of fluorescamine (*) in acetone (0.3 mg/ml) is added, and the fluorescence of the mixture is measured using an excitation wavelength of 475 nm. Graphics of dependence of fluorescence on the amount of protein are prepared and angles of slopes are compared, with tangent of the angle proportional to the amount of primary amino groups in the protein. Measurements of the rate of rhodamine-labeled iprRNase I pegylation by fluorescence demonstrates that a single 2×10 kda PEG is attached to iprRNase I. The labeled ipeRNase-PEG-R8 (the asterisk indicating fluorescence) exhibits stronger antiviral efficacy against ssRNA corona virus compared with ipr*RNase I and *RNase I (see Table 21).

Enhanced Antiviral Activity of Human iprRNase I-pEG-R8 Against ssRNA Corona Virus Compared with iprRNase I and RNase I.

| Nuclease [UA/ml] | Cellular Uptake [OD$_{430}$ nm] | Average Titer |
|---|---|---|
| Control [0] | 0 | 6.4 |
| *RNase I | 110 | 5.4 |
| Irp*RNase* I | 130 | 3.4 |
| Irp*RNase I-PEG-R8 | 230 | 1.8 |

*indicates fluorescamine label.

Example 34

Antiviral Treatment of Plants by Modified Antiviral Nucleases

Viral infections are a cause of significant economic losses in agriculture, and most known plant viruses have RNA genomes. RNase A-like and RNase III-like nucleases exhibit preferential hydrolytic activity towards ssRNA and dsRNA respectively, and non-specific nucleases such as Benzonaze digest both RNA and DNA. The nucleases can be chemically and genetically modified as described herein to obtain compositions enhanced hydrolytic activity and protection from endogenous proteases and nuclease inhibitors.

The example demonstrates that treatment of potato apical meristem with Benzonase (BNase) increases the yield of virus-free plants. PEG and R8 are attached to Benzonase to obtain BNase-PEG-R8 conjugate, which exhibits enhanced antiviral activity towards a number of plant viruses. Application of BNase-PEG-R8 to potatoes infected by plant viruses is found to yield virus-free potatoes. Dry components of the Murashigo-Scooga medium (MSM), necessary to prepare 100 ml of the medium, are dissolved in 90 ml of distilled water and sterilized by autoclaving. Benzonase is added in amount 100,000 Kunitz units/10 ml of medium. The sterile lyophilized Benzonase in effective amounts is dissolved in 10 ml of sterile distilled water. When the medium is cooled to about 45° C., the solution of benzonase (10 ml) was added. To 100 ml of nutritive medium 0.5 ml of 20% sterile solution of $MgSO_4$ is added. Polyethylene glycol (mPEG-NHS, MW 10 kDa) and K-R8 are covalently attached to Benzonase following the procedure described in Example 1.

Treatment of Potato Apical Meristem with Native and Modified Benzonase Increases the Number of Virus-Free Plants.

|  | Infected Plants [No] | Regenerated Plants [No] | Virus-Free Plants [No] |
| --- | --- | --- | --- |
| Nuclease Treatment |  |  |  |
| Control | 50 | 6 | 1 |
| BNase | 50 | 15 | 9 |
| BNase-PEG | 50 | 28 | 18 |
| BNase-PEG-R8 | 50 | 39 | 32 |

Example 35

Treatment of Viral Diseases in Livestock by Modified Antiviral Nucleases

Numerous DNA and RNA viruses cause diseases in livestock. A significant economic loss results from viral diseases such as bovine adenovirus, swine influenza virus, bovine herpes virus, swine pox virus, infectious bovine rhino-tracheitis and others. There are currently no drugs for treatment or prevention of these diseases. Our data demonstrate the potential antiviral efficacy of polymer modified DNase-like and RNase-like nucleases against livestock viruses in cell culture.

Example 36

Administration of Modified Nucleases to Inhibit Replication of DNA and RNA Poultry Viruses to Prevent and Treat Viral Disease in Poultry RNA and DNA avian viruses such as avian influenza A, avian adenovirus, fowl pox and other poultry viruses are responsible for highly contagious viral diseases causing epizootics which cannot be effectively prevented or treated. Both DNase-like and RNase-like native and modified nucleases of this invention, including Benzonase, oligopeptides such as Ser-His and Ser-His-Asp, and chemical nucleases such as transition metal compounds with nucleolytic properties, are applied for treatment of viruses in chicken, turkey and other birds. A group of 20 chickens is treated with aerosol of di-peptide D-Ser-His or tri-peptide D-Ser-His-FD-Asp dissolved in saline, twice per day for 3 days, while 20 control chickens are treated with saline. All chickens are infected with avian adenovirus. All control chickens develop bronchitis and succumb while 18 and 19 chickens out of 20 treated with D-Ser-His and D-Ser-His-D-Asp, respectively, survive.

Example 37

Application of Modified Nucleases for Protecting Honeybees from Virus Causing Epizootics of Honeybee Viral Paralysis A number of economically important insects such as honey bees, silkworms and some insects grown as biological pesticides are killed by epizootics caused by insect viruses. There are currently no means of protection against these epizootics. Our data demonstrate a protective effect of modified nucleases against disease caused by honeybee paralysis virus (HPV), which results in devastating effects on honeybee farms. Since HBVP is ssRNA containing virus (Bailey, J. Inverteb. Pathol. 7: 132-135 1965), nucleases with RNase activity are applied to protect honeybees from HBVP-induced deadly disease. The protective effects of native and modified Benzonase and bovine RNase A against HBVP viral paralysis are demonstrated.

Infectious titer of HBVP is $10^{-8}$ per ml. The honeybees are infected by feeding the viral emulsion. Insects are sprayed by an aerosol of enzyme diluted in physiological solution 3 hours before the inoculation of virus. Table 23 shows that the enzymes penetrate the body fluids and cells through respiratory pores. Treatment of insects 6 hours after inoculation of virus still protected them from development of disease.

Treatment with BNase, RNase A, BNase-PEG and RNase A-PEG Protects Honeybees from Viral Paralysis

| Nuclease [UA/ml] | Infected Honeybees | Surviving Honeybees |
| --- | --- | --- |
| Control [0] | 100 | [0] |
| RNase A [200, 500, 1000, 1500] | 100 | [4, 11, 67, 100] |
| RNase A-PEG [200, 500, 1000, 1500] | 100 | [28, 46, 100, 100] |
| BNase [200, 500, 1000, 1500] | 100 | [12, 21, 72, 100] |
| BNase-PEG [200, 500, 1000, 1500] | 100 | [32, 78, 100, 100] |

Example 38

Treatment of Silkworms with Wild-Type or Modified BNase Protects Insects from the Development of Viral Nuclear Polyhedrosis Nuclear polyhedrosis is a viral disease with a devastating effect on this field of agriculture. Selection for resistance as well as radiation treatment are not used widely in view of low efficacy of these methods of protection against this disease. Spraying silkworms with 500 UA/ml Benzonase (BNase) is herein found to be non-toxic and protective from the development of the nuclear polyhedrosis. BNase-PEG complex exhibits enhanced antiviral efficacy compared with that of wild-type BNase (see Table 24).

Protection of Silkworms Against Infectious Viral Polyhedrosis by BNase and BNase-PEG

| Nuclease [UA/ml] | Infected Silkworms | Surviving |
| --- | --- | --- |
| Control [0, 0, 0] | 50 | [7, 7, 8] |
| BNase A [500, 500, 500] | 50 | [25, 28, 27] |
| BNase A-PEG [500, 500, 500] | 50 | [45, 46, 48] |

Example 39

DNase Inhibits Development of Lymphatic Leukemia Promoted in AKR Mice by Mouse Leukemia Virus Leukemia in AKR mice is known to be promoted by mouse leukemia virus. The lymphoid tissues of AKR mice contain mouse leukemia virus, and spontaneously develop leukemia, at the age of 6-8 months. Administration of bovine DNase I and bovine TDNase to AKR mice s.c. in amounts of 5,000 KuU/g body weight every second day for a month is found herein to preclude the development of leukemia.

To study the treatment effect of DNase and TDNase, the experiment is carried out on 9-10 month old AKR mice with manifestations of lymphoid leukemia. A significant increase in the size of lymph nodes, thymus, liver and spleen and high mitotic index in lymphoid tissues is observed in these animals. The treated groups include 24 mice in each while the control group includes 19 mice. Administration of DNase I and TDNase every four days s.c., in a dose of 5,000 KuU/g body weight, results in a decrease of lymphatic tissues and mitotic index to normal levels, and in an increase in longevity of animals. However, a more profound effect is obtained in animals receiving TDNase than DNase, and receiving TDNase-PEG than TDNase, as is shown in Table 25.

Antiviral Effect of DNase and TDNase on Viral Lymphatic Leukemia in AKR Mice

| Nuclease Control [0] | Liver (g) | Mitotic Index | Longevity (weeks) |
|---|---|---|---|
| DNase [5 kUA/g] | 941 ± 33 | 0.18 ± 0.02 | 16 ± 1.0 |
| TDNase [5 kUA/g] | 670 ± 23 | 0.14 ± 0.01 | 21 ± 1.2 |
| DNasePEG [5 kUA/g] | 643 ± 21 | 0.12 ± 0.01 | 23 ± 1.2 |
| TDNasePEG [5 kUA/g] | 500 ± 18 | 0.08 ± 0.01 | 26 ± 1.2 |

Example 40

Combined RNase A and DNase I Treatment of ssRNA Equine Encephalitis Virus

The example demonstrates enhanced efficacy of combined RNase and DNase for treatment of ssRNA equine encephalitis virus. To further increase efficacy of the combined treatment, the enzymes are pegylated, and RNase-PEG and DNase-PEG are applied. Complementary viral ssDNA production may involve endogenous reverse transcriptase (RT) in cells infected by RNA viruses such as lymphocytic choriomeningitis virus (LCMV; Klenerman, et al., Letters to Nature, 390: 298-301, 1997), polio, and measles viruses (Zhdanov, Nature 256: 471-473, 1975). Without being limited by any particular theory or mechanism, endogenous RT may reverse-transcribe RNA derived from other infectious viruses (Zhdanov, Nature 256: 471-473, 1975). The source of the endogenous RT could be an endogenous retrovirus or another interspersed element (Wiener et al., A. Rev. Biochem. 55, 631-661, 1986), wherein reverse transcripts from such endogenous sources may account for 10-20% of the mammalian genome (Coffin, in Reverse Transcriptase, pp. 445-479, 1993, Eds. Skalka and Gough, Cold Spring Harbor Lab Press, NY). Low levels of RT activity due to presence of endogenous avian leukosis viruses (ALV-E) and endogenous avian viruses (EAV) was also detected in chicken embryonic fibroblast substrates used in production of measles, mumps and yellow fever vaccines (Hussain et al., Journal of Virology, January 77(2): 1105-1111, 2003; Johnson and Heneine, J. Virol. 75(8): 3605-3612, 2001).

Enhancement of the antiviral effect of RNase A against ssRNA viruses is shown herein by combining RNase A with DNase I. Surprisingly, treatment with a combination of DNase I and RNase A produces a synergistic inhibitory effect on the replication of equine encephalitis virus (see Table 26). These combinations may be relevant to other RNA viruses. The combined application treatment with both DNase-like and RNase-like enzymes has potential for treating of other RNA viruses as well as co-infections of RNA viruses with RNA RT or DNA RT viruses.

Synergistic Effect of Combined DNase and RNase Treatment of ssRNA Equine Encephalitis Virus

| Nuclease [UA/ml] | Titer [log$TCD_{50}$/0.1 ml] | Average Titer |
|---|---|---|
| Control [0] | 7.0; 7.3; 7.1 | 7.1 |
| RNase A [500] | 5.2; 5.2; 5.4 | 5.26 |
| DNase I [500] | 6.5; 6.2; 6.6 | 6.56 |
| RNase + DNase [500] | 4.8; 4.3; 4.6 | 4.5 |
| RNase-PEG [500] | 4.1; 4.2; 4.3 | 4.2 |
| DNase-PEG [500] | 4.8; 5.2; 5.3 | 5.1 |
| RNase-PEG [250] + DNase-PEG [250] | 2.8; 3.1; 3.0 | 2.9 |

What is claimed is:

1. A method for treating a viral disease in a subject, the method comprising:
    administering to the subject a composition for destruction of targeted nucleic acids inside biological cells, the composition comprising:
        a core carrier comprising a plurality of first multivalent molecular scaffolds and a plurality of second multivalent molecular scaffolds, each of the first and second multivalent molecular scaffolds being covalently bound to the core carrier, each first and second multivalent molecular scaffold comprising a polymer,
        at least one of the first multivalent molecular scaffolds further comprising a plurality of cell membrane permeating peptides covalently bound to the first multivalent molecular scaffold for effective internalization of the composition into cytoplasm of the biological cells, wherein the first multivalent molecular scaffolds are nuclease-free,
        at least one of the second multivalent molecular scaffolds comprising a plurality of nucleic acid targeting ligands covalently bound to the second multivalent molecular scaffold that is capable of binding specific sequences on targeted nucleic acids inside the biological cells, at least one nuclease covalently bound to the second multivalent molecular scaffold that is capable of destruction of the targeted nucleic acids that are bound to the nucleic acid targeting ligands inside the biological cells.

2. The method as recited in claim 1, wherein the first multivalent molecular scaffold further comprises at least one cell-surface receptor-recognizing ligand exhibiting binding affinity to cell surface receptors (CSR) of a primary host cell.

3. The method as recited in claim 1, wherein the second multivalent molecular scaffold further comprises at least one cell-surface receptor-recognizing ligand exhibiting binding affinity to cell surface receptors (CSR) of a primary host cell.

4. The method as recited in claim 1, wherein the second multivalent molecular scaffold further comprises at least one cell membrane permeating peptide.

5. The method as recited in claim 1, wherein the at least one nuclease comprises at least one non-natural amino acid.

6. The method as recited in claim 1, wherein at least one cell membrane permeating peptide of the plurality of cell membrane permeating peptides is selected from the group consisting of basic peptides containing at least one Arg(R) or a non-natural analog of arginine residue, or containing at least one Lys(K) or a non-natural analog of lysine residue; octa-arginine peptide R8; Lysine-terminated octa-arginine peptide K-R8 containing at least one D-Arginine residue; and Cysteine (C)-terminated octa-arginine peptide C-R8 containing at least one D-Arginine residue.

7. The method as recited in claim 1, wherein at least one cell membrane permeating peptide of the plurality of cell membrane permeating peptides is selected from the group consisting of: HIV TAT$_{47-57}$; ANTp16; W/R; CWK$_{18}$; AlkCWK$_{18}$, Di-CWK$_{18}$, Transportan; DipaLytic; K$_{16}$RGD; P1; P2; P3; P3a; P9.3; Pep-1; Plae; Kplae; cKplae; MGP; HA2; LARL$_6$; Hel-11-7; KK; KWK; RWR; SV40 NLS7; NLS 12; NLS12a; SV40 NLS13; AV NLS13; AV RME NLS 17; AV FP NLS28; SV40 N1 NLS24; Loligomer; HSV-1 VP22; HSV-1 VP22r; E. coli H57S, Penetratin and detoxified exotoxin A (ETA).

8. The method as recited in claim 1, wherein the first multivalent molecular scaffold comprises a dendrimer, a branch of dendrimer, a linear polymer, a branched polymer, a forked polymer, a star polymer or a block copolymer.

9. The method as recited in claim 1, wherein the second multivalent molecular scaffold comprises a dendrimer, a branch of dendrimer, a linear polymer, a branched polymer, a forked polymer, a star polymer or a block copolymer.

10. The method as recited in claim 1, wherein the second multivalent molecular scaffold comprise a polymeric material selected from the group consisting of polyethylene glycol (PEG), poly(2-hydroxy-ethyl-L-glutamine) (PHEG), N-(2-Hydroxypropyl) methacrylamide (HPMA), poly-lactic acid (PEG-PLA), poly-lactic-glycolic acid (PEG-PLGA) and poly-L-lactic acid (PEG-PLLA).

11. The method as recited in claim 1, wherein the first multivalent molecular scaffold comprises a polymeric material selected from the group consisting of polyethylene glycol (PEG), poly(2-hydroxy-ethyl-L-glutamine) (PHEG), N-(2-Hydroxypropyl) methacrylamide (HPMA), poly-lactic acid (PEG-PLA), poly-lactic-glycolic acid (PEG-PLGA) and poly-L-lactic acid (PEG-PLLA).

12. The method as recited in claim 11, wherein the polymeric material comprises at least one hydrolyzable linkage selected from the group consisting of a carboxylate, a phosphate ester, an acetal, an imine, an orthoester, an enol ether, a diketane acetal, a ketal, and an anhydride.

13. The method as recited in claim 1, wherein the plurality of nucleic acid targeting ligands comprises an oligomer selected from the group consisting of a peptide nucleic acid (PNA), a locked nucleic acid (LNA), a bridged nucleic acids (BNA), a morpholino or pyrrolidine-amide oligonucleotide mimic (POM) oligonucleotide, a hairpin polyamide and an oligopeptide having a sequence of a zinc finger.

14. The method as recited in claim 1, wherein the second multivalent molecular scaffolds are attached to the core carrier by Watson-Crick hybridization between first and second complementary oligonucleotides, the first oligonucleotide bound to the multivalent molecular scaffold and the second oligonucleotide bound to the core carrier.

15. The method as recited in claim 14, wherein the first and second complementary oligonucleotides are locked nucleic acids (LNA) or bridged nucleic acids (BNA).

16. The method as recited in claim 1, wherein the core carrier is a dendrimer core carrier.

17. The method as recited in claim 1, wherein the core carrier is a branched polymer core carrier.

* * * * *